US007342011B2

(12) United States Patent
van Duzer et al.

(10) Patent No.: US 7,342,011 B2
(45) Date of Patent: *Mar. 11, 2008

(54) RIFAMYCIN ANALOGS AND USES THEREOF

(75) Inventors: John H. van Duzer, Georgetown, MA (US); Arthur F. Michaelis, Devon, PA (US); William B. Geiss, Athens, NY (US); Douglas G. Stafford, Niskayuna, NY (US); Joseph Raker, Delmar, NY (US)

(73) Assignee: ActivBiotics, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/915,919

(22) Filed: Aug. 11, 2004

(65) Prior Publication Data
US 2005/0043298 A1  Feb. 24, 2005

Related U.S. Application Data

(60) Provisional application No. 60/497,058, filed on Aug. 22, 2003.

(51) Int. Cl.
C07D 498/18 (2006.01)
A61K 31/535 (2006.01)
A61P 31/54 (2006.01)

(52) U.S. Cl. .............................. 514/224.5; 514/229.5; 514/252.1; 540/458

(58) Field of Classification Search ................ 540/458; 514/224.5, 229.5, 252.1
See application file for complete search history.

(56) References Cited

U.S. PATENT DOCUMENTS

| | | | |
|---|---|---|---|
| 3,338,888 | A | 8/1967 | Bickel et al. |
| 4,690,919 | A | 9/1987 | Yamane et al. |
| 4,859,661 | A | 8/1989 | Kano et al. |
| 4,965,261 | A | 10/1990 | Kanoo et al. |
| 4,983,602 | A | 1/1991 | Yamane et al. |
| 5,547,683 | A | 8/1996 | Yano et al. |
| 5,786,349 | A | 7/1998 | Yamashita et al. |
| 5,981,522 | A | 11/1999 | Yamashita et al. |
| 6,316,433 | B1 | 11/2001 | Rose et al. |
| 6,486,161 | B1 | 11/2002 | Fujii et al. |
| 6,566,354 | B1 | 5/2003 | Rose et al. |
| 6,900,204 | B2 | 5/2005 | Michaelis et al. |
| 7,078,399 | B2 | 7/2006 | Michaelis et al. |
| 2003/0203903 | A1 | 10/2003 | Rose et al. |
| 2003/0236265 | A1 | 12/2003 | Sayada |
| 2004/0014750 | A1 | 1/2004 | Michaelis et al. |
| 2004/0034021 | A1 | 2/2004 | Michaelis et al. |
| 2004/0063718 | A1 | 4/2004 | Michaelis et al. |
| 2004/0077533 | A1 | 4/2004 | Sayada |
| 2004/0106590 | A1 | 6/2004 | Eisenstein |
| 2005/0043298 | A1 | 2/2005 | Van Duzer et al. |
| 2005/0137189 | A1 | 6/2005 | Van Duzer et al. |
| 2005/0197333 | A1 | 9/2005 | Van Duzer et al. |

FOREIGN PATENT DOCUMENTS

| | | |
|---|---|---|
| JP | S58-225093 | 12/1983 |
| JP | S59-231092 | 12/1984 |
| JP | S61-022090 | 1/1986 |
| JP | S62-240688 | 10/1987 |
| JP | S62-242687 | 10/1987 |
| JP | S63-035578 | 2/1988 |
| JP | S63-035579 | 2/1988 |
| JP | S63-233987 | 9/1988 |
| WO | WO97/09047 | * 3/1997 |
| WO | WO 2005/058231 | 6/2005 |
| WO | WO 2005/062882 | 7/2005 |

OTHER PUBLICATIONS

Bermudez et al., "Activity of KRM 1648 Alone or in Combination with Ethambutol or Clarithromycin Against Mycobacterium Avium in Beige Mouse Model of Disseminated Infection," *Antimicrobial Agents and Chemotherapy* 38(8):1844-1848 (1994).

Dhople, "In Vivo Susceptibility of Mycobacterium Ulcerans to KRM-1648, A New Benzoxazinorifamycin, in Comparison with Rifampicin," *Arzneimittelforschung* 51(6):501-505 (2001).

Dietze et al., "Safety and Bactericidal Activity of Rifalazil in Patients with Pulmonary Tuberculosis," *Antimicrobial Agents and Chemotherapy* 45(7):1972-1976 (2001).

Emori et al., "Evaluation of in Vivo Therapeutic Efficacy of a New Benzoxazinorifamycin, KRM-1648, in SCID Mouse Model for Disseminated Mycobacterium Avium Complex Infection," *International Journal of Antimicrobial Agents* 10(1):59-65 (1998).

Fujii et al., "In Vitro and In Vivo Antibacterial Activities of KRM-1648 and KRM-1657, New Rifamycin Derivatives," *Antimicrobial Agents and Chemotherapy* 38:1118-1122 (1994).

Gidoh et al., "Bactericidal Action at Low Doses of a New Rifamycin Derivative, 3'-Hydroxy-5'-(4-isobutyl-1-piperazinyl) Benzoxazinorifamycin (KRM-1648) on Mycobacterium Leprae Inoculated into Footpads of Nude Mice," *Leprosy Review* 63(4):319-328 (1992).

Heep et al., "Detection of Rifabutin Resistance and Association of rpoB Mutations with Resistance to Four Rifamycin Derivatives in Helicobacter Pylori," *European Journal of Clinical Microbiology & Infectious Diseases* 21:143-145 (2002).

Hirata et al., "In Vitro and In Vivo Activities of the Benzoxazinorifamycin KRM-1648 Against Mycobacterium Tuberculosis," *Antimocrobial Agents and Chemotherapy* 39(10):2295-2303 (1995).

(Continued)

*Primary Examiner*—Bruck Kifle
(74) *Attorney, Agent, or Firm*—Clark & Elbing LLP

(57) ABSTRACT

The present invention features rifamycin analogs that can be used as therapeutics for treating or preventing a variety of microbial infections. In one form, the analogs are acetylated at the 25-position, as is rifamycin. In another form, the analogs are deacetylated at the 25-position. In yet other forms, benzoxazinorifamycin, benzthiazinorifamycin, and benzdiazinorifamycin analogs are derivatized at various positions of the benzene ring, including 3'-hydroxy analogs, 4'- and/or 6' halo and/or alkoxy analogs, and various 5' substituents that incorporate a cyclic amine moiety.

12 Claims, No Drawings

OTHER PUBLICATIONS

Hosoe et al., "Identification and Antimicrobial Activity of Urinary Metabolites of a Rifamycin Derivative in Dog," *Xenobiotica* 26(3):321-332 (1995).

Hosoe et al., "Pharmacokinetics of KRM-1648, A New Benzoxazinorifamycin, in Rats and Dogs," *Antimicrobial Agents and Chemotherapy* 40(12):2749-2755 (1996).

Ji et al., "How Effective is KRM-1648 in Treatment of Disseminated Mycobacterium Avium Complex Infections in Beige Mice?," *Antimicrobial Agents and Chemotherapy* 40(2):437-442 (1996).

Kelly et al., "Low-Dose Aerosol Infection Model for Testing Drugs for Efficacy Against Mycobacterium Tuberculosis," *Antimicrobial Agents and Chemotherapy* 40(12):2809-2812 (1996).

Klemens et al., "Activity of KRM-1648 in Combination with Isoniazld Against Mycobacterium Tuberculosis in a Murine Model," *Antimicrobial Agents and Chemotherapy* 40(2):298-301 (1996).

Kump et al., "244. Zur Kenntnis von Rifamycin-S. Reaktionen des chinoiden Nucleus. Modifikationen von Antibiotica, 9. Mitteilung [1] (244. Understanding of Rifamycin-S. Reactions of the Quinoid Nucleus. Modifications of Antibiotics. 9)" *Helvetica Chimica Acta* 56(7):2348-2377 (1973). [*Article in German with English Abstract*].

Kuo et al., "A Comparison of the In-Vitro Sensitivity of Chlamydia Pneumoniae to Macrolides and a New Benzoxazinorifamycin, KRM-1648," *Infectious Disease and Therapy*, 21:317-321 (1997).

Lenaerts et al., "Evaluation of Rifalazil in a Combination Treatment Regimen as an Alternative to Isoniazid-Rifampin Therapy in a Mouse Tuberculosis Model," *Antimicrobial Agents and Chemotherapy* 44(11):3167-3168 (2000).

Mae et al., "Effect of a New Rifamycin Derivative, Rifalazil, on Liver Microsomal Enzyme Induction in Rat and Dog," *Xenobiotica* 28(8):759-766 (1998).

Mae et al., "Isolation and Identification of Major Metabolites of Rifalazil in Mouse and Human," *Xenobiotica* 29:1073-1087 (1999).

Roblin et al., "In Vitro Activities of Rifamycin Derivatives ABI-1648 (Rifazil, KRM-1648), ABI-1657, and ABI-1131 Against Chlamydia Trachomatis and Recent Clinical Isolates of Chlamydia Pneumoniae," *Antimicrobial Agents and Chemotherapy* 47:1135-1136 (2003).

Saito et al., "Therapuetic Efficacy of Benzoxazinorifamycin, KRM-1648, Against Disseminated Mycobacterium Avium Infection Induced in Rabbits," *Abstracts of the General Meeting of the American Society for Microbiology* 93:174 (1993). [*Abstract U31*].

Sano et al., "Therapeutic Effects of Benzoxazinorifamycin KRM-1648 Administered Alone or in Combination with a Half-Sized Secretory Leukocyte Protease Inhibitor or the Nonsteroldal Anti-inflammatory Drug Diclofenac Sodium Against Mycobaterium Avium Complex Infection in Mice," *Antimicrobial Agents and Chemotherapy* 43(2):360-364 (1999).

Sato et al., "Antimicrobial Activities of Benzoxazinorifamycin KRM-1648, Clarithromycin and Levofloxacin Against Intracellular Mycobacterium Avium Complex Phagocytosed by Murine Peritoneal Macrophages," *Journal of Antimicrobial Chemotherapy* 41(1):77-83 (1998).

Seligson et al., "A New Prodrug of Paclitaxel: Synthesis of Protaxel." *Anti-Cancer Drugs* 12(4):305-313 (2001).

Shimizu et al., "Effects of the Chinese Traditional Medicine Mao-Bushi-Saishin-To on Therapeutic Efficacy of a New Benzoxazinorifamycin, KRM-1648, Against Mycobacterium Avium Infection in Mice," *Antimicrobial Agents and Chemotherapy* 43(3):514-519 (1999).

Shoen et al., "Evalution of Rifalazil in Long-term Treatment Regimens for Tuberculosis in Mice," *Antimicrobial Agents and Chemotherapy* 44(6):1458-1462 (2000).

Tomioka et al., "Effects of Benzoxazinorifamycin KRM-1648 on Cytokine Production at Sites of Mycobaterium Avium Complex Infection Induced in Mice," *Antimicrobial Agents and Chemotherapy* 41(2):357-362 (1997).

Tomioka et al., "In Vivo Antileprosy Activity of the Newly Synthesized Benzoxazinorifamycin, KRM-1648," *International Journal of Leprosy* 61(2):255-258 (1993).

Tomioka et al., "Intramacrophage Passage of Mycobacterium Tuberculosis and M. Avium Complex Alters the Drug Susceptibilities of the Organisms as Determined by Intracellular Susceptibility Testing using Macrophages and Type II Alveolar Epithelial Cells," *Antimicrobial Agents and Chemotherapy* 46(2):519-521 (2002).

Tomioka et al., "Therapeutic Efficacy of KRM-1648 in Combination with Other Antimicrobials Against M. Leprae Infection Induced in Nude Mice," *International Journal of Leprosy and Other Mycobacterial Diseases* 61:77A (1993). [*Abstract EX9*].

Wallis et al., "Inhibition of Isoniazid-induced Expression of Mycobacterium Tuberculosis Antigen 85 in Sputum: Potential Surrogate Marker in Tuberculosis Chemotherapy Trials," *Antimicrobial Agents and Chemotherapy* 45(4):1302-1304 (2001).

Yamamoto et al., "Activity of KRM-1648 Alone or in Combination with Both Ethambutol and Kanamycin or Clarithromycin Against Mycobacterium Intracellulare Infections in Beige Mice," *Antimicrobial Agents and Chemotherapy* 40(2):429-432 (1996).

Yamamoto et al., "In Vitro Bactericidal and In Vivo Therapeutic Activities of a New Rifamycin Derivative, KRM-1648, Against Mycobacterium Tuberculosis," *Antimicrobial Agents and Chemotherapy* 40(2):426-428 (1996).

Yamane T. et al., "Synthesis and Biological Activity of 3'-Hydroxy-5'-Aminobenzoxazinorifamycin Derivatives." *Chemical and Pharmaceutical Bulletin* 41(1):148-155 (1993).

* cited by examiner

RIFAMYCIN ANALOGS AND USES THEREOF

CROSS REFERENCE TO RELATED APPLICATIONS

Applicants claim the priority benefit under 35 U.S.C. 119(e) of prior provisional application serial no. 60/497,058 filed Aug. 22, 2003, the disclosure of which is incorporated herein by reference.

BACKGROUND OF THE INVENTION

The present invention relates to the field of antimicrobial agents.

The use of antibiotics by humans can be seen as an evolutionary experiment of enormous magnitude, a window from which to view not-quite-natural selection operating in real time. Within 50 years, the number of species and strains of pathogenic and commensal bacteria resistant to antibiotics and the number of antibiotics to which they are resistant has increased virtually monotonically world-wide. As a result, infections that had been readily treatable by chemotherapy may no longer be so. It is clear that the evolution and spread of resistance can be attributed to the use and overuse of antibiotics. Increased resistance of bacterial infections to antibiotic treatment has been extensively documented and has now become a generally recognized medical problem, particularly with nosocomial infections. See, for example, Jones et al., *Diagn. Microbiol. Infect. Dis.* 31:379-388, 1998; Murray, *Adv. Intern. Med.* 42:339-367, 1997; and Nakae, *Microbiologia* 13:273-284, 1997.

Throughout the developed world there is public and governmental concern about the increasing prevalence of antimicrobial resistance to chemotherapy in bacteria that cause diseases in humans. Many pathogens exist for which there are few effective treatments, and the number of strains resistant to available drugs is continually increasing. New antimicrobial agents and improved methods are thus needed for the treatment and prevention of infections by such pathogens.

SUMMARY OF THE INVENTION

The present invention features rifamycin analogs that can be used as therapeutics for treating or preventing a variety of microbial infections.

Accordingly in a first aspect, the invention features a compound of formula (I):

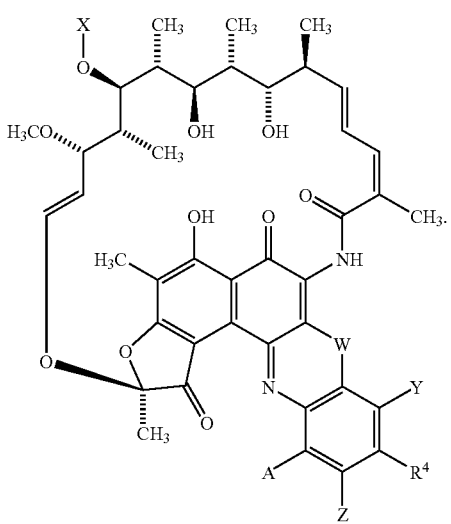

(I)

In formula (I), A is H, OH, O—($C_1$-$C_6$ alkyl), or O—($C_1$-$C_4$ alkaryl); W is O, S, or $NR^1$, where $R^1$ is H or $C_1$-$C_6$ alkyl; X is H or $COR^2$, where $R^2$ is $C_1$-$C_6$ alkyl, which can be substituted with from 1 to 5 hydroxyl groups, or O—($C_3$-$C_7$ alkyl, can be substituted with from 1 to 4 hydroxyl groups; each of Y and Z is independently H, $C_1$-$C_6$ alkoxy, or Hal; and $R^4$ has the following formula:

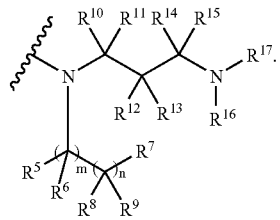

For the formula that represents $R^4$, when each of m and n is 1, each of $R^5$ and $R^6$ is H, or $R^5$ and $R^6$ together are =O; $R^7$ and $R^{10}$ together form a single bond or a $C_1$-$C_3$ linkage, $R^7$ and $R^{12}$ together form a single bond or a $C_1$-$C_2$ linkage, or $R^7$ and $R^{14}$ together form a single bond or a $C_1$ linkage; $R^8$ is H, $C_1$-$C_6$ alkyl, or $C_1$-$C_4$ alkaryl, or $R^8$ and $R^{12}$ together form a single bond, or $R^8$ and $R^9$ together are =N—$OR^8$, where $R^{18}$ is H, $C_1$-$C_6$ alkyl, or $C_1$-$C_4$ alkaryl; $R^9$ is H, $C_1$-$C_6$ alkyl, or $C_1$-$C_4$ alkaryl, or $R^9$ and $R^8$ together are =N—$OR^{18}$; $R^{10}$ is H, $C_1$-$C_6$ alkyl, or $C_1$-$C_4$ alkaryl, or $R^{10}$ and $R^{17}$ together form a $C_1$-$C_3$ alkyl linkage, or $R^{10}$ and $R^{11}$ together are =O; $R^{11}$ is H, $R^{12}$ is H, $C_1$-$C_6$ alkyl, or $C_1$-$C_4$ alkaryl; each of $R^{13}$ and $R^{15}$ is H, $C_1$-$C_6$ alkyl, or $C_1$-$C_4$ alkaryl; $R^{14}$ is H, $C_1$-$C_6$ alkyl, or $C_1$-$C_4$ alkaryl; $R^{16}$ is H, $C_1$-$C_6$ alkyl, $C_1$-$C_6$ alkoxy, $C_6$-$C_{12}$ aryl, heteroaryl, $C_1$-$C_4$ alkaryl, or $C_1$-$C_4$ alkheteroaryl, or $R^{16}$ and $R^{12}$ together form a $C_2$-$C_4$ alkyl linkage, or $R^{16}$ and $R^{10}$ together form a $C_1$-$C_2$ alkyl linkage; and $R^{17}$ is H, $C_1$-$C_6$ alkyl, $COR^{19}$, $CO_2R^{19}$, or $CONHR^{19}$, $CSR^{19}$, $COSR^{19}$, $CSOR^{19}$, $CSNHR^{19}$, $SO_2R^{19}$, or $SO_2NHR^{19}$, where $R^{19}$ is $C_1$-$C_6$ alkyl, $C_6$-$C_{12}$ aryl, $C_1$-$C_4$ alkaryl, heteroaryl, or $C_1$-$C_4$ alkheteroaryl, and where each alkyl linkage of 2 carbons or more may contain a non-vicinal O, S, or $N(R^{23})$ where $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R_{24}$, or $SO_2NHR^{24}$, where $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl.

When m is 0 and n is 1, $R^7$ and $R^{10}$ together form a single bond or a $C_1$-$C_4$ linkage, $R^7$ and $R^{12}$ together form a single bond or a $C_1$-$C_3$ linkage, or $R^7$ and $R^{14}$ together form a single bond or a $C_1$-$C_2$ linkage; each of $R^8$, $R^9$, and $R^{11}$ is H; $R^{15}$ is H, $C_1$-$C_6$ alkyl, or $C_1$-$C_4$ alkaryl; $R^{10}$ is H; $R^{12}$ is H, $C_1$-$C_6$ alkyl, or $C_1$-$C_4$ alkaryl, $R^{12}$ and $R^{13}$ together form a —$CH_2CH_2$—linkage, or $R^{12}$ and $R^{16}$ together form a $C_2$-$C_4$ alkyl linkage; $R^{13}$ is H, $C_1$-$C_6$ alkyl, $C_1$-$C_4$ alkaryl; $R^{14}$ is H, $C_1$-$C_6$ alkyl, or $C_1$-$C_4$ alkaryl; $R^{16}$ is H, $C_1$-$C_6$ alkyl, $C_1$-$C_6$ alkoxy, $C_6$-$C_{12}$ aryl, heteroaryl, $C_1$-$C_4$ alkaryl, or $C_1$-$C_4$ alkheteroaryl, or $R^{16}$ and $R^{12}$ together form a $C_2$-$C_4$ alkyl linkage; and $R^{17}$is H, $C_1$-$C_6$ alkyl, $COR^{19}$, $CO_2R^{19}$, or $CONHR^{19}$, $CSR^{19}$, $COSR^{19}$, $CSOR^{19}$, $CSNHR^{19}$, $SO_2R^{19}$, or $SO_2NHR^{19}$, where $R^{19}$ is $C_1$-$C_6$ alkyl, $C_6$-$C_{12}$ aryl, $C_1$-$C_4$ alkaryl, heteroaryl, or $C_1$-$C_4$ alkheteroaryl, and where each alkyl linkage of 2 carbons or more may contain a non-vicinal O, S, or $N(R^{23})$ where $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, where $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl.

Alternatively, for a compound of formula (I), A is OH; X is H; W, Y, and Z are as described above; and $R^4$ is selected from the following groups:

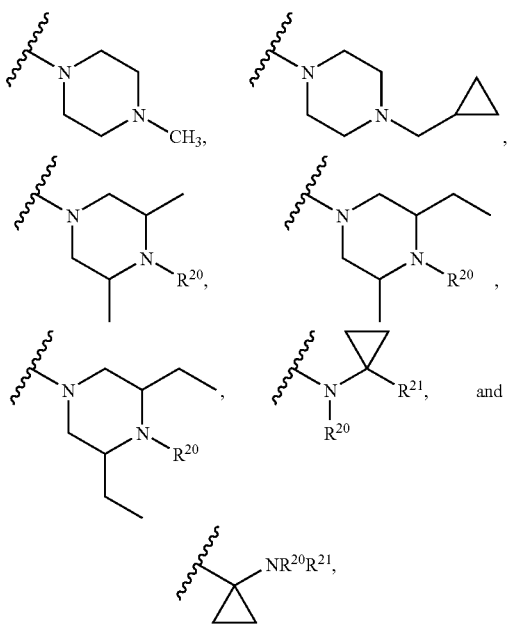

where $R^{21}$ is H, $C_1$-$C_6$ alkyl, $C_6$-$C_{12}$ aryl, heteroaryl, $C_1$-$C_4$ alkaryl, or $C_1$-$C_4$ alkheteroaryl, $R^{20}$ is H, $C_1$-$C_6$ alkyl, $COR^{19}$, $CO_2R^{19}$, or $CONHR^{19}$, $CSR^{19}$, $COSR^{19}$, $CSOR^{19}$, $CSNHR^{19}$, $SO_2R^{19}$, or $SO_2NHR_{19}$, where $R^{19}$ is $C_1$-$C_6$ alkyl, $C_6$-$C_{12}$ aryl, $C_1$-$C_4$ alkaryl, heteroaryl, or $C_1$-$C_4$ alkheteroaryl.

Alternatively, A is OH; X is $COCH_3$; W, Y, and Z are as described above; and $R^4$ is selected from the groups consisting of:

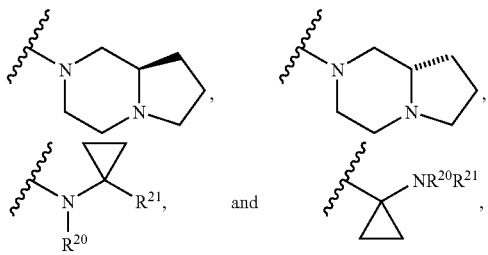

where $R^{21}$ is H, $C_1$-$C_6$ alkyl, $C_6$-$C_{12}$ aryl, heteroaryl, $C_1$-$C_4$ alkaryl, or $C_1$-$C_4$ alkheteroaryl, $R^{20}$ is H, $C_1$-$C_6$ alkyl, $COR^{19}$, $CO_2R^{19}$, or $CONHR^{19}$, $CSR_{19}$, $COSR^{19}$, $CSOR^{19}$, $CSNHR^{19}$, $SO_2R^{19}$, $SO_2NHR^{19}$, where $R^{19}$ is $C_1$-$C_6$ alkyl, $C_6$-$C_{12}$ aryl, $C_1$-$C_4$ alkaryl, heteroaryl, or $C_1$-$C_4$ alkheteroaryl.

Alternatively, A is H or OH; X is H or $COCH_3$; W, Y, and Z are as described above; and $R^4$ is

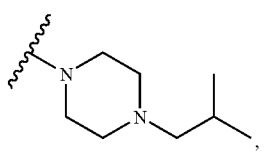

with the proviso that one or both of Y and Z are halogen.

Alternatively, A is H or OH; X is H or $COCH_3$; W, Y, and Z are as described above; and $R^4$ is

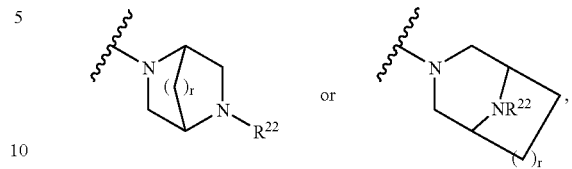

where $R^{22}$ is H, $C_1$-$C_6$ alkyl, $C_6$-$C_{12}$ aryl, heteroaryl, $C_1$-$C_4$ alkaryl, $C_1$-$C_4$ alkheteroaryl, $COR^{24}$, $CO_2R^{24}$, $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl, and r is 1-2.

Alternatively, A is H or OH; X is H or $COCH_3$; W, Y, and Z are as described above; and $R^4$ is

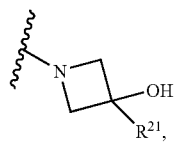

where $R^{21}$ is H, $C_1$-$C_6$ alkyl, $C_6$-$C_{12}$ aryl, heteroaryl, $C_1$-$C_4$ alkaryl, or $C_1$-$C_4$ alkheteroaryl.

Alternatively, A is H or OH; X is H or $COCH_3$; W, Y, and Z are as described above; and $R^4$ is

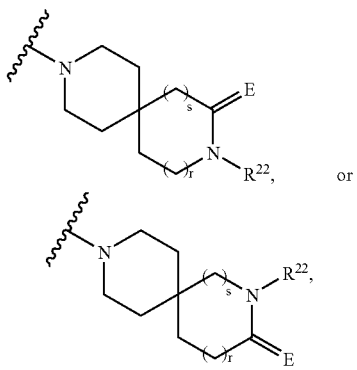

where =E is =O or (H,H), $R^{22}$ is H, $C_1$-$C_6$ alkyl, $C_6$-$C_{12}$ aryl, heteroaryl, $C_1$-$C_4$ alkaryl, $C_1$-$C_4$ alkheteroaryl, $COR^{24}$, $CO_2R^{24}$, $CONHR^{24}$, $CSR_{24}$, $COSR^{24}$, $CSOR^{24}$, $CSNHR^{24}$, $SO_2R^{24}$, or $SO^2NHR^{24}$, where $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl, r is 1-2, and s is 0-1.

Alternatively, A is H or OH; X is H or $COCH_3$; W, Y, and Z are as described above; and $R^4$

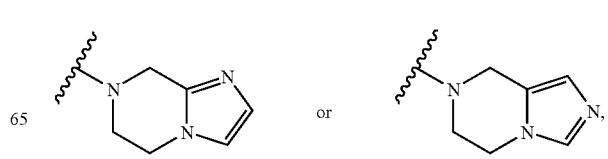

where $R^{22}$ is H $C_1$-$C_6$ alkyl, $COR^{24}$, $CO_2R^{24}$, $CONHR^{24}$, $CSR^{24}$, $COSR^{24}$, $CSOR^{24}$, $CSNHR^{24}$, $SO_2R^{24}$, or $SO_2NHR^{24}$, where $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl.

In one embodiment, A is H or OH; X is H or $COCH_3$; W, Y, and Z are as described above; and $R^4$ is

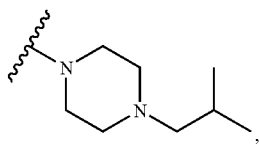

where one or both of Y and Z is F.

In another embodiment, W is O; Y is H; Z is H; A is OH, X is H or $COCH_3$, and $R^4$ is

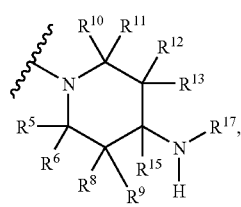

where each of $R^5$ and $R^6$ is H, or $R^5$ and $R^6$ together are =O, each of $R^8$, $R^9$, $R^{12}$, $R^{13}$ and $R^{15}$ is H, $C_1$-$C_6$ alkyl, or $C_1$-$C_4$ alkaryl, each of $R^{10}$ and $R^{11}$ is H, $C_1$-$C_6$ alkyl, or $C_1$-$C_4$ alkaryl, or $R^{10}$ and $R^{11}$ together are =O, $R^{17}$ is H, $C_1$-$C_6$ alkyl, $COR^{19}$, $CO_2R^{19}$, or $CONHR^{19}$, $CSR_{19}$, $COSR^{19}$, $CSOR^{19}$, $CSNHR^{19}$, $SO_2R^{19}$, or $SO_2NHR^{19}$, where $R^{19}$ is $C_1$-$C_6$ alkyl, $C_6$-$C_{12}$ aryl, $C_1$-$C_4$ alkaryl, heteroaryl, or $C_1$-$C_4$ alkheteroaryl.

In another embodiment, W is O; Y is H; Z is H; A is H or OH, X is H or $COCH_3$, and $R^4$ is

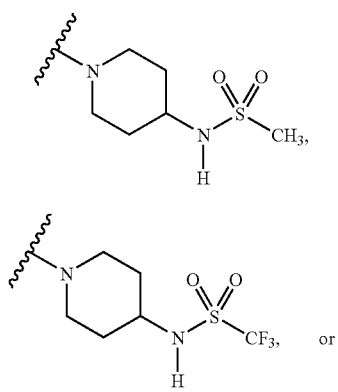

In another embodiment, W is O; Y is H; Z is H; A is H or OH, X is H or $COCH_3$, and $R^4$ is

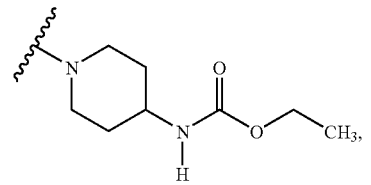

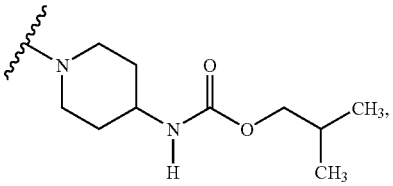

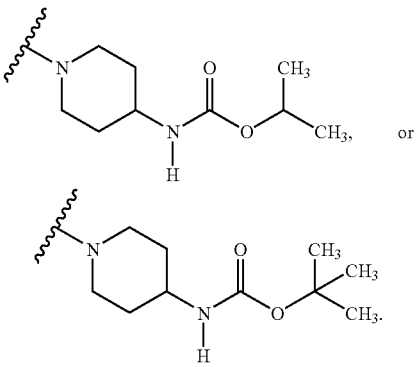

In another embodiment, W is O; Y is H; Z is H; X is H or $COCH_3$; A is H or OH; and $R^4$ is selected from the group consisting of:

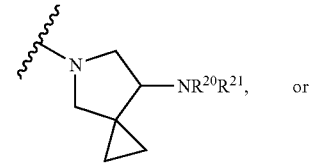

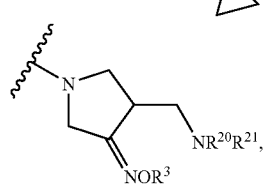

where $R^{20}$ and $R^{21}$ are as described above, or

W is O; Y is H; Z is H; X is H or $COCH_3$, A is H or OH; and $R^4$ is:

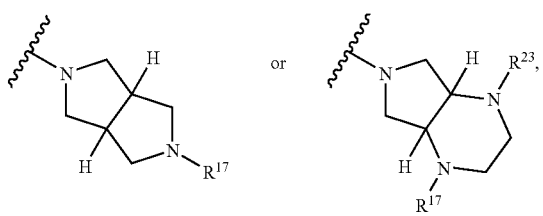

where each of $R^{17}$ and $R^{23}$ is, independently, H, $C_1$-$C_6$ alkyl, $COR^{24}$, $CO_2R^{24}$, or $CONHR^{24}$, where $R^{24}$ is $C_1$-$C_6$ alkyl, $C_1$-$C_4$ alkaryl, heteroaryl, or $C_1$-$C_4$ alkheteroaryl., or W is O, Y is H, Z is H, X is $COCH_3$, A is OH, and $R^4$ is selected from the group consisting of

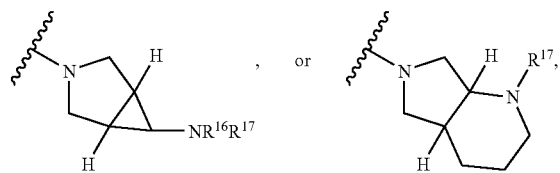

where $R^{16}$ and $R^{17}$ are as described above.

The invention also features pharmaceutical compositions that include a compound of formula (I) and a pharmaceutically acceptable carrier or diluent.

In another aspect, the invention features a method of killing, treating, or preventing a microbial infection in an animal, preferably a mammal, and most preferably a human, that includes administering to the animal a pharmaceutical composition of the invention. The invention further features treating or preventing diseases associated with such microbial infections. Such methods of treatment or prevention may include the oral, topical, intravenous, intramuscular, or subcutaneneous administration of compositions of the invention.

The invention also features a method for treating or preventing the development of an atherosclerosis-associated disease in a patient by administering to the patient a compound of formula (I) in an amount effective to treat or prevent the development of the atherosclerosis-associated disease in the patient. The patient is typically diagnosed as having the atherosclerosis-associated disease (or being at increased risk of developing the disease) or as having macrophages or foam cells infected with *C. pneumoniae* prior to the administration of a compound of formula (I).

The invention also features a method of reducing the level of C-reactive protein in a patient in need thereof by administering to the patient a compound of formula (I) in an amount effective to reduce the level of C-reactive protein in the patient. In one embodiment, the patient has not been diagnosed as having a bacterial infection. In another embodiment, the patient has been diagnosed as having macrophages or foam cells infected with *C. pneumoniae*.

The invention also features a method for reducing *C. pneumoniae* replication in macrophages or foam cells in a patient in need thereof by administering a compound of formula (I) to the patient in an amount effective to reduce *C. pneumoniae* replication in macrophages or foam cells in the patient.

The invention also features a method for treating a persistent *C. pneumoniae* infection in macrophages or foam cells in a patient by administering a compound of formula (I) to the patient in an amount effective to treat the *C. pneumoniae* infection in macrophages or foam cells in the patient.

The invention also features a method for treating a chronic disease associated with an infection of *C. pneumoniae* by administering a compound of formula (I) to the patient in an amount effective to treat the infection.

In any of the foregoing aspects, the dosage of a compound of formula (I) is normally about 0.001 to 1000 mg/day. The compound may be given daily (e.g., a single oral dose of 2.5 to 25 mg/day) or less frequently (e.g., a single oral dose of 5, 12.5, or 25 mg/week). Treatment may be for one day to one year, or longer. In one embodiment, a compound of formula (I) is administered at an initial does of 2.5 to 100 mg for one to seven consecutive days, followed by a maintenance dose of 0.005 to 10 mg once every one to seven days for one month, one year, or even for the life of the patient.

If desired, a compound of formula (I) may be administered in conjunction with one or more additional agents such as anti-inflammatory agents (e.g., non-steroidal anti-inflammatory drugs (NSAIDs; e.g., detoprofen, diclofenac, diflunisal, etodolac, fenoprofen, flurbiprofen, ibuprofen, indomethacin, ketoprofen, meclofenameate, mefenamic acid, meloxicam, nabumeone, naproxen sodium, oxaprozin, piroxicam, sulindac, tolmetin, celecoxib, rofecoxib, aspirin, choline salicylate, salsalte, and sodium and magnesium salicylate) and steroids (e.g., cortisone, dexamethasone, hydrocortisone, methylprednisolone, prednisolone, prednisone, triamcinolone)), antibacterial agents (e.g., azithromycin, clarithromycin, erythromycin, gatifloxacin, levofloxacin, amoxicillin, metronidazole, penicillin G, penicillin V, methicillin, oxacillin, cloxacillin, dicloxacillin, nafcillin, ampicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, moxifloxacin, gemifloxacin, sitafloxacin, daptomycin, garenoxacin, ramoplanin, faropenem, polymyxin, tigecycline, AZD2563, or trimethoprim), platelet aggregation inhibitors (e.g., abciximab, aspirin, cilostazol, clopidogrel, dipyridamole, eptifibatide, ticlopidine, or tirofiban), anticoagulants (e.g., dalteparin, danaparoid, enoxaparin, heparin, tinzaparin, or warfarin), antipyretics (e.g., acetaminophen), or lipid lowering agents (e.g., cholestyramine, colestipol, nicotinic acid, gemfibrozil, probucol, ezetimibe, or statins such as atorvastatin, rosuvastatin, lovastatin simvastatin, pravastatin, cerivastatin, and fluvastatin). These additional agents may be administered within 14 days, 7 days, 1 day, 12 hours, or 1 hour of administration of the rifamycin analog, or simultaneously therewith. The additional therapeutic agents may be present in the same or different pharmaceutical compositions as the rifamycin analog. When present in different pharmaceutical compositions, different routes of administration may be used. For example, a compound of formula (I) may be administered orally, while a second agent may be administered by intravenous, intramuscular, or subcutaneous injection.

The invention also features a stent coated with a compound of formula (I). The stent can be, e.g., a wire mesh tube used to hold open an artery. Stents are typically inserted following angioplasty.

The invention also features methods and compositions for treating or preventing an ear infection in a patient by orally administering or topically administering to the affected otic area (e.g., the tympanic membrane or the external auditory canal of the ear) of the patient a pharmaceutical composition including a therapeutically effective amount of a compound of formula (I). The compositions and methods of the invention can also be used to treat or prevent infections that result from surgery.

The invention also features a pharmaceutical composition suitable for topical administration to the ear of a patient containing a compound of formula (I) and a pharmaceutically-acceptable excipient, administered at a dose capable of reducing the infection in the patient. According to this invention, the compound of formula (I) can be in the amount between 0.001% and 5% weight/volume (w/v), preferably 0.01% and 3% w/v, more preferably 0.1% and 1% w/v, or most preferably 0.1% and 0.4% w/v. The compound of formula (I) can also be impregnated in a porous media (for example, an ear wick such as a sponge, gauze, cotton, or hydrocellulose), which is suitable for insertion into the ear of a patient. If desired, the composition may also include one or more penetration enhancers (e.g., alcohols, polyols, sulfoxides, esters, ketones, amides, oleates, surfactants, alkanoic acids, lactam compounds, alkanols, or admixtures thereof).

In another aspect, the invention also features a method for treating or preventing the development of an ear infection in a patient using a composition described above. A compound of formula (I) can be administered to the infected ear by means of drops or by the insertion of a rifamycin analog-impregnated porous media into the external ear canal to the tympanic membrane. Ear infections that can be treated using the methods and composition of the invention include otitis media and otitis externa. Types of otitis media amenable to treatment include, for example, acute otitis media, otitis media with effusion, and chronic otitis media. Types of otitis externa include acute otitis externa, chronic otitis externa, and malignant otitis externa. A rifamycin analog of the invention is administered to the ear (e.g., the tympanic membrane or the external auditory canal of the ear) to treat or prevent bacterial infections associated with otitis media (e.g., an infection of *H. influenza, M. catarhalis*, or *S. pneumoniae*) or in otitis externa (e.g., an infection of *S. intermedius, Streptococcus* spp. *Pseudomonas* spp., *Proteus* spp., or *E. coli*).

The methods and compositions of the invention are also useful to treat infections associated with otic surgical procedures such as tympanoplasty, stapedectomy, removal of tumors, or cochlear implant surgery. The compositions may also be used prophylactically, prior to therapies or conditions that can cause ear infections. Compositions containing a compound of formula (I) can therefore be applied to an area of the ear to which the surgical intervention will be performed, within at least seven days (before or after) of the surgical intervention. When treating a patient affected with otitis externa, an acidification therapy involving the administration of an acetic acid solution to the ear of the patient may also be performed.

Typically, patients are administered one to four drops of a compound of the invention in a total amount between 0.001% and 5% w/v, preferably 0.01% and 3% w/v, more preferably 0.1% and 1% w/v, or most preferably 0.1% and 0.4% w/v. The composition may be given daily (e.g., once, twice, three times, or four times daily) or less frequently (e.g., once every other day, or once or twice weekly). Treatment may be for 1 to 21 days, desirably 1 to 14 days, or even 3 to 7 days. Additional therapeutic agents, such as anti-inflammatory agents (e.g., non-steroidal anti-inflammatory or steroid), anesthetics, zinc salts, or other antimicrobial agents, can also be administered with a rifamycin analog of the invention. Non-steroidal anti-inflammatory agents include, for example, detoprofen, diclofenac, diflunisal, etodolac, fenoprofen, flurbiprofen, indomethacin, ketoprofen, mechlofenameate, mefenamic acid, meloxicam, nabumeone, naproxen sodium, oxaprozin, piroxicam, sulindac, tolmeting, celecoxib, rofecoxib, choline salicylate, salsate, sodium salicylate, magnesium salicylate, aspirin, ibuprofen, paracetamol, acetaminophen, and pseudoephedrine and steroids include, for example, hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone. Anesthetics according to the invention can be, for example, benzocaine, butamben picrate, tetracaine, dibucaine, prilocaine, etidocaine, mepivacaine, bupivicaine, and lidocaine. A zinc salt can be zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, and zinc glycinate, and antimicrobial agents according to the invention include, for example, azithromycin, clarithromycin, erythromycin, gatifloxacin, levofloxacin, amoxicillin, metronidazole, penicillin G, penicillin V, methicillin, oxacillin, cloxacillin, dicloxacillin, nafcillin, ampicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, telithromycin, ABT-773, lincomycin, clindamycin, vancomycin, oritavancin, dalbavancin, teicoplanin, quinupristin and dalfopristin, sulphanilamide, para-aminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, moxifloxacin, gemifloxacin, sitafloxacin, daptomycin, garenoxacin, ramoplanin, faropenem, polymyxin, tigecycline, AZD2563, or trimethoprim. These additional therapeutic agents can be present in the same or different pharmaceutical compositions as the rifamycin analog of formula (I). When a therapeutic agent is present in a different pharmaceutical composition, different routes of administration may be used. The rifamycin analog of formula (I) and the second therapeutic agent, for example, may also be administered within 24 hours of each other, and an anti-inflammatory agent, for example, may be administered orally, or by intravenous, intramuscular, or subcutaneous injection.

To increase the efficacy of the topically administered rifamycin analog-containing composition, it is desirable that the amount of debris and granulation tissue are reduced in the infected ear of the patient at least one hour prior to the administration of the rifamycin and at least once a day. Debris can be removed, for example, by suction, irrigation with a solution containing hydrogen peroxide, cauterization, or by manual techniques employing microinstruments and microscope. Reduction in the amount of granulation tissue in the infected ear may be performed by means of cautering, or by the administration of a steroid.

The invention also features a pharmaceutical pack containing (i) a compound of formula (I) in an amount effective to treat a patient having an ear infection; and (ii) instructions for administering the compound to the ear of a patient. The invention also features a container containing a rifamycin analog of formula (I) and a pharmaceutical excipient suitable for topical administration to the ear. If desired, an applicator for applying the composition to the ear may also be included. Desirably, the rifamycin analog can be in the amount between 0.001% and 5% weight/volume (w/v), preferably 0.01% and 3% w/v, more preferably 0.1% and 1% w/v, or most preferably 0.1% and 0.4% w/v and is present in amounts sufficient to treat for at least 1, 3, 5, 7, 10, 14, or 21 days. A penetration enhancer may also be added (e.g., alcohols, polyols, sulfoxides, esters, ketones, amides, oleates, surfactants, alkanoic acids, lactam compounds, alkanols, or admixtures thereof).

The invention also features a method for treating chronic gastritis, gastric ulcer, or duodenal ulcer associated with an infection of *H. pylori*, or preventing the disease or infection, in a patient. The method includes the step of orally administering to the patient an effective amount of a compound of formula (I) to treat the patient. The compound is normally about 0.1 to 1000 mg/day (desirably about 1 to 100 mg/day, more desirably about 1 to 50 mg/day, and even more desirably about 1 to 25 mg/day). The compound may be given daily (e.g., once, twice, three times, or four times daily) or less frequently (e.g., once every other day, or once or twice weekly). Treatment may be for 1 to 21 days, desirably 1 to 14 days or even 3 to 7 days. If desirable, a rifamycin analog can be administered with a proton pump inhibitor (e.g., omeprazole, esomeprazole, lansoprazole, leminoprazole, pantoprazole or robeprazole), and/or bismuth preparation (e.g., colloidal bismuth subcitrate or bismuth subsalicylate).

The invention also features a pharmaceutical pack including (i) a compound of formula (I) in an amount effective to treat chronic gastritis, gastric ulcer, or duodenal ulcer associated with an infection of *H. pylori* in a patient; and (ii) instructions for administering the compound to the patient. Desirably, the compound is in unit amounts of between 0.1 and 1000 mg (e.g., between 1 and 50 mg or between 5 and 50 mg), and is present in amounts sufficient to treat for at least 1, 3, 5, 7, 10, 14, or 21 days. The pack may optionally include a proton pump inhibitor and/or bismuth preparation. In one embodiment, the rifamycin analog of formula (I) is in a pharmaceutical composition with the proton pump inhibitor and/or bismuth preparation.

The invention also features a method for treating a patient having antibiotic-associated bacterial diarrhea or an infection of *C. difficile*, or preventing the disease or infection in the patient. The method includes the step of orally administering to the patient an effective amount of a compound of formula (I) to treat the patient. The compound is normally about 0.1 to 1000 mg/day (desirably about 1 to 100 mg/day, more desirably about 1 to 50 mg/day, and even more desirably about 1 to 25 mg/day). The compound may be given daily (e.g., once, twice, three times, or four times daily) or less frequently (e.g., once every other day, or once or twice weekly). Treatment may be for 1 to 21 days, desirably 1 to 14 days or even 3 to 7 days. In one embodiment, a rifamycin analog is administered at an initial dose of between 5 and 100 mg, followed by subsequent doses of between 1 and 50 mg for 3 to 7 days. A single dose (e.g., in a dosage of between 5 and 50 mg) can also be employed in the method of the invention. If desirable, a rifamycin analog of formula (I) can be administered with a second antibiotic (e.g., metronidazole or vancomycin), either simultaneously or sequentially.

The invention also features a pharmaceutical pack including (i) a compound of formula (I) in an amount effective to treat a patient having antibiotic-associated bacterial diarrhea or an infection of *C. difficile*; and (ii) instructions for administering the compound to the patient for treating or preventing a *C. difficile* infection. Desirably, the compound is in unit amounts of between 1 and 1000 mg (e.g., between 1 and 50 mg or between 5 and 50 mg), and is present in amounts sufficient to treat for at least 1, 3, 5, 7, 10, 14, or 21 days.

The invention features a method for treating a patient having an infection of *Chlamydia trachomatis*. The method includes the step of administering to the patient a compound of formula (I) in an amount effective to treat the patient. In one embodiment, the patient is administered a single oral dose of a compound of formula (I).

The invention also features a pharmaceutical pack that includes (i) a single oral dose of a compound of formula (I) in an amount effective to treat a patient having an infection of *C. trachomatis* or *N. gonorrhoeae*; and (ii) instructions for administering the single oral dose to the patient. Desirably, the dose is in an amount between 0.1 and 100 mg (e.g., between 1 and 50 mg or between 5 and 25 mg).

The invention also features a method of treating a patient having a chronic disease associated with a bacterial infection caused by bacteria capable of establishing a cryptic phase. This method includes the step of administering to a patient a compound of formula (I) for a time and in an amount sufficient to treat the cryptic phase of the bacterial infection. The chronic disease may be an inflammatory disease. Examples of inflammatory diseases include but are not limited to asthma, coronary artery disease, arthritis, conjunctivitis, lymphogranuloma venerum (LGV), cervicitis, and salpingitis. The chronic disease can also be an autoimmune disease (e.g., systemic lupus erythematosus, diabetes mellitus, or graft versus host disease).

The invention also features a method for treating a patient diagnosed as being infected with a bacterium having a multiplying form and a non-multiplying form by administering to the patient (i) a rifamycin analog of formula (I) and (ii) a second antibiotic that is effective against the multiplying form of the bacterium, wherein the two antibiotics are administered in amounts and for a duration that, in combination, treat the patient.

In a related aspect, the invention features a method of treating a chronic disease associated with a persistent bacterial infection or treating the persistent bacterial infection itself by administering a compound of formula (I).

In preferred embodiments of any of the foregoing aspects, the persistent intracellular bacterial infection is caused by one of the following: *Chlamydia* spp. (e.g., *C. trachomatis, C. pneumoniae, C. psittaci, C. suis, C. pecorum, C. abortus, C. caviae, C. felis, C. muridarum*), *N. hartmannellae, W. chondrophila, S. negevensis*, or *P. acanthamoeba*.

The time sufficient to treat a bacterial infection ranges from one week to one year, but it can also be extended over the lifetime of the individual patient, if necessary. In more preferable embodiments, the duration of treatment is at least 30 days, at least 45 days, at least 10 days, or at least 180 days. Ultimately, it is most desirable to extend the treatment for such a time that the bacterial infection is no longer detected.

The rifamycin analogs of formula (I) are useful against drug resistant Gram-positive cocci such as methicillin-resistant *S. aureus* and vancomycin-resistant enterococci, and are useful in the treatment of community-acquired pneumonia, upper and lower respiratory tract infections, skin and soft tissue infections, hospital-acquired lung infections, bone and joint infections, and other bacterial infections.

The compounds and methods of the present invention can be used to treat, for example, respiratory tract infections, acute bacterial otitis media, bacterial pneumonia, urinary tract infections, complicated infections, noncomplicated infections, pyelonephritis, intra-abdominal infections, deep-seated abcesses, bacterial sepsis, skin and skin structure infections, soft tissue infections, bone and joint infections, central nervous system infections, bacteremia, wound infections, peritonitis, meningitis, infections after burn, urogenital tract infections, gastrointestinal tract infections, pelvic inflammatory disease, endocarditis, and other intravascular infections.

The compounds and methods of the present invention can also be used to treat diseases associated with bacterial infection. For example, bacterial infections can produce inflammation, resulting in the pathogenesis of atherosclerosis, multiple sclerosis, rheumatoid arthritis, diabetes, Alzheimer's disease, asthma, cirrhosis of the liver, psoriasis, meningitis, cystic fibrosis, cancer, or osteoporosis. Accordingly, the present invention also features a method of treating the diseases associated with bacterial infection listed above.

The methods of the present invention can be used to treat or prevent infections by bacteria from a variety of genera, such as *Escherichia* spp., *Enterobacter* spp., *Enterobacteriaceae* spp., *Klebsiella* spp., *Serratia* spp., *Pseudomonas* spp., *Acinetobacter* spp., *Bacillus* spp., *Micrococcus* spp., *Arthrobacter* spp., *Peptostreptococcus* spp., *Staphylococcus* spp., *Enterococcus* spp., *Streptococcus* spp., *Haemophilus* spp., *Neisseria* spp., *Bacteroides* spp., *Citrobacter* spp., *Branhamella* spp., *Salmonella* spp., *Shigella* spp., *Proteus* spp., *Clostridium* spp., *Erysipelothrix* spp., *Listeria* spp., *Pasteurella* spp., *Streptobacillus* spp., *Spirillum* spp., *Fusospirocheta* spp., *Treponema* spp., *Borrelia* spp., *Actinomycetes* spp., *Mycoplasma* spp., *Chlamydia* spp., *Rickettsia* spp., *Spirochaeta* spp., *Legionella* spp., *Mycobacteria* spp., *Ureaplasma* spp., *Streptomyces* spp., and *Trichomoras* spp. Accordingly, the invention features a method of treating infections by the bacteria belonging to the genera above, among others.

Particular Gram-positive bacterial infections that can be treated according to the method of the invention include infections by *Staphylococcus aureus, Staphylococcus epidermidis, Enterococcusfaecalis, Enterococcus faecium, Clostridium perfringens, Streptococcus pyogenes, Streptococcus pneumoniae*, other *Streptococcus* spp., and other *Clostridium* spp.

Multi-drug resistant strains of bacteria can be treated according to the methods of the invention. Resistant strains of bacteria include penicillin-resistant, methicillin-resistant, quinolone-resistant, macrolide-resistant, and/or vancomycin-resistant bacterial strains. The multi-drug resistant bacterial infections to be treated using the methods of the present invention include infections by penicillin-, methicillin-, macrolide-, vancomycin-, and/or quinolone-resistant *Streptococcus pneumoniae*; penicillin-, methicillin-, macrolide-, vancomycin-, and/or quinolone-resistant *Staphylococcus aureus*; penicillin-, methicillin-, macrolide-, vancomycin-, and/or quinolone-resistant *Streptococcus pyogenes*; and penicillin-, methicillin-, macrolide-, vancomycin-, and/ or quinolone-resistant enterococci.

The invention also features a method of eradicating non-multiplying bacteria not eradicated in a patient following treatment with a first antibiotic by administering to the patient a rifamycin antibiotic of formula (I) or (II) in an amount and for a duration sufficient to eradicate the non-multiplying bacteria in the patient.

Compounds of the invention may also be used to treat or prevent viral infections.

In another aspect, the invention features a pharmaceutical composition that includes a compound described herein in any pharmaceutically acceptable form, including isomers such as diastereomers and enantiomers, salts, solvates, and polymorphs thereof. In various embodiments, the composition includes a compound of the invention along with a pharmaceutically acceptable carrier or diluent.

In another aspect, the invention features a method of treating a microbial infection in an animal comprising co-administering a compound of the invention along with one or more antifungal agents, antiviral agents, antibacterial agents, or antiprotozoan agents, or combinations thereof.

In any of the above aspects, desirable rifamycin analogs of formula (I) include 4'-fluoro-5'-(4-isobutyl-1-piperazinyl)benzoxazinorifamycin, 4'-fluoro-5'-(1-piperazinyl)benzoxazinorifamycin, 4'-fluoro-5'-(3-methyl-1-piperazinyl)benzoxazinorifamycin, 4'-methoxy-6'-fluoro-5'-(3-methyl-1-piperazinyl)benzoxazinorifamycin, 4',6'-difluoro-5'-[(3R,5S)-3,5-dimethyl-1-piperazinyl]benzoxazinorifamycin, 4'-fluoro-6'-methoxy-5'-[(4aS,7aS)-octahydro-6H-pyrrolo[3,4-b]pyridin-6-yl]benzoxazinorifamycin, 4'-fluoro-5'-[6-amino-3-azabicyclo[3.1.0]hex-3-yl]benzoxazinorifamycin, 25-O-deacetyl-4'-fluoro-5'-(4-isobutyl-1-piperazinyl)benzoxazinorifamycin, 25-O-deacetyl-4'-fluoro-5'-(1-piperazinyl)benzoxazinorifamycin, 25-O-deacetyl-4'-fluoro-5'-(3-methyl-1-piperazinyl)benzoxazinorifamycin, 25-O-deacetyl-4'-methoxy-6'-fluoro-5'-(3-methyl-1-piperazinyl)benzoxazinorifamycin, 25-O-deacetyl-4',6'-difluoro-5'-[(3R,5S)-3,5-dimethyl-1-piperazinyl]benzoxazinorifamycin, 25-O-deacetyl-4'-fluoro-6'-methoxy-5'-[(4aS,7aS)-octahydro-6H-pyrrolo[3,4-b]pyridin-6-yl]benzoxazinorifamycin, 25-O-deacetyl-4'-fluoro-5'-[6-amino-3-azabicyclo[3.1.0]hex-3-yl]benzoxazinorifamycin, 25-O-deacetyl-25-(2'',3''-dihydroxypropylcarbonoxy)-5'-(4-isobutyl-1-piperazinyl)benzoxazinorifamycin, 25-O-deacetyl-25-(2'',3''-dihydroxypropylcarbonoxy)-4'-fluoro-5'-(4-isobutyl-1-piperazinyl)benzoxazinorifamycin, 25-O-deacetyl-25-(2'',3''-dihydroxypropylcarbonoxy)-4'-fluoro-5'-(1-piperazinyl)benzoxazinorifamycin, 25-O-deacetyl-25-(2'',3''-dihydroxypropylcarbonoxy)-4'-fluoro-5'-(3-methyl-1-piperazinyl)benzoxazinorifamycin, 25-O-deacetyl-25-(2'',3''-dihydroxypropylcarbonoxy)-4'-methoxy-6'-fluoro-5'(3-methyl-1-piperazinyl)benzoxazinorifamycin, 25-O-deacetyl-25-(2'',3''-dihydroxypropylcarbonoxy)-4',6'-difluoro-5'-[(3R,5S)-3,5-dimethyl-1-piperazinyl]benzoxazinorifamycin, 25-O-deacetyl-25-(2'',3''-dihydroxypropylcarbonoxy)-4'-fluoro-6'-methoxy-5'-[(4aS,7aS)-octahydro-6H-pyrrolo[3,4-b]pyridin-6-yl]benzoxazinorifamycin, 25-O-deacetyl-25-(2'',3''-dihydroxypropylcarbonoxy)-4'-fluoro-5'-[6-amino-3-azabicyclo[3.1.0]hex-3-yl]benzoxazinorifamycin, 4'-fluoro-5'-(4-isobutyl-1-piperazinyl)benzthiazinorifamycin, 4'-fluoro-5'-(1-piperazinyl)benzthiazinorifamycin, 4'-fluoro- 5'-(3-methyl-1-piperazinyl)benzthiazinorifamycin, 4'-methoxy-6'-fluoro-5'-(3-methyl-1-piperazinyl)benzthiazinorifamycin, 4',6'-difluoro-5'-[(3R,5S)-3,5-dimethyl-1-piperazinyl]benzthiazinorifamycin, 4'-fluoro-6'-methoxy-5'-[(4aS,7aS)-octahydro-6H-pyrrolo[3,4-b]pyridin-6-yl]benzthiazinorifamycin, 4'-fluoro-5'-[6-amino-3-azabicyclo[3.1.0]hex-3-yl]benzthiazinorifamycin, 25-O-deacetyl-4'-fluoro-5'-(4-isobutyl-1-piperazinyl)benzthiazinorifamycin, 25-O-deacetyl-4'-fluoro-5'-(1-piperazinyl)benzthiazinorifamycin, 25-O-deacetyl-4'-fluoro-5'-(3-methyl-1-piperazinyl)benzthiazinorifamycin, 25-O-deacetyl-4'-methoxy-6'-fluoro-5'-(3-methyl-1-piperazinyl)benzthiazinorifamycin, 25-O-deacetyl-4',6'-difluoro-5'-[(3R,5S)-3,5-dimethyl-1-piperazinyl]benzthiazinorifamycin, 25-O-deacetyl-4'-fluoro-6'-methoxy-5'-[(4aS,7aS)-octahydro-6H-pyrrolo[3,4-b]pyridin-6-yl]benzthiazinorifamycin, 25-O-deacetyl-4'-fluoro-5'-[6-amino-3-azabicyclo[3.1.0]hex-3-yl]benzthiazinorifamycin, 3'-hydroxy-5'-((3R,5S)-3,5-dimethylpiperazinyl)benzoxazinorifamycin, 3'-hydroxy-5'-((3R,5S)-3,5-diethylpiperazinyl)benzoxazinorifamycin, 3'-hydroxy-5'-((3R,5S)-3-ethyl-5-methylpiperazinyl)benzoxazinorifamycin, 25-O-deacetyl-3'-hydroxy-5'-((3R,5S)-3,5-dimethylpiperazinyl)benzoxazinorifamycin, 25-O-deacetyl-3'-hydroxy-5'-((3R,5S)-3-ethyl-5-methylpiperazinyl)benzoxazinorifamycin, 25-O-deacetyl-3'-hydroxy-5'-((3R,5S)-3,5-diethylpiperazinyl)benzoxazinorifamycin, 3'-hydroxy-5'-((4aR,7aR)octahydro-1H-pyrrolyl[3,4-b]pyridine)benzoxazinorifamycin, 3'-hydroxy-5'-((4aS,7aS)octahydro-1H-pyrrolyl[3,4-b]pyridine)benzoxazinorifamycin, 3'-hydroxy-5'-((8aR)-octahydropyrrolyl[1,2-a]pyrazine)benzoxazinorifamycin, 25-O-deacetyl-3'-hydroxy-5'-((8aR)-octahydropyrrolyl[1,2-a]pyrazine)benzoxazinorifamycin, 3'-hydroxy-5'-((8aS)-octahydropyrrolyl[1,2-a]pyrazine)benzoxazinorifamycin, 25-O-deacetyl-3'-hydroxy-5'-((8aS)-octahydropyrrolyl[1,2-a]pyrazine)benzoxazinorifamycin, 25-O-deacetyl-3'-hydroxy-5'-(4-methylpiperazinyl)benzoxazinorifamycin, 3'-hydroxy-5'-(ethyl piperidinyl-4-ylcarbamate)benzoxazinorifamycin, 25-O-deacetyl-3'-hydroxy-5'-(ethyl piperidinyl-4-ylcarbamate)benzoxazinorifamycin, 3'-hydroxy-5'-((3Z)-4-(aminomethyl)pyrrolidinyl-3-one O-methyloxime)benzoxazinorifamycin, 3'-hydroxy-5'-(5-azaspiro[2.4]heptan-7-amino-5-yl) benzoxazinorifamycin, 3'-hydroxy-5'-(5-aminopyrrolidinyl) benzoxazinorifamycin, 3'-hydroxy-5'-(4-ethylcarbamyl-1-piperidinyl)benzoxazinorifamycin (compound 1), 3'-hydroxy-5'-[6-(2-trimethylsilyl)ethylcarbamyl-(1R,5S)-3-azabicyclo[3.1.0]hex-3-yl]benzoxazinorifamycin (compound 2), 25-O-deacetyl-3'-hydroxy-5'-(4-ethylcarbamyl-1-piperidinyl)benzoxazinorifamycin (compound 3), 3'-hydroxy-5'-[6-amino-(1R,5S)-3-azabicyclo[3.1.0]hex-3-yl]benzoxazinorifamycin (compound 4), 3'-hydroxy-5'-[(4aS,7aS)-octahydro-6H-pyrrolo[3,4-b]pyridin-6-yl]benzoxazinorifamycin (compound 5), 3'-hydroxy-5'-(1-piperidinyl-4-(N-phenyl)propanamide)benzoxazinorifamycin (compound 6), 25-O-deacetyl-3'-hydroxy-5'-[(4aS,7aS)-octahydro-6H-pyrrolo[3,4-b]pyridin-6-yl]benzoxazinorifamycin (compound 7), 25-O-deacetyl-3'-hydroxy-5'-(1-piperidinyl-4-(N-phenyl)propanamide)benzoxazinorifamycin (compound 8), 3'-hydroxy-5'-(4-morpholinyl-1-piperidinyl)benzoxazinorifamycin (compound 9), 3'-hydroxy-5'-(3,8-diazabicyclo[3.2.1]octan-3-yl)benzoxazinorifamycin (compound 10), 25-O-deacetyl-3'-hydroxy-5'-(4-morpholinyl-1-piperidinyl)benzoxazinorifamycin (compound 11), 3'-hydroxy-5'-[(4aR,7aR)-octahydro-6H-pyrrolo[3,4-b]pyridin-6-yl]benzoxazinorifamycin (compound 12), 3'-hydroxy-5'-(4-(2-methylpropyl)carbamyl-1-piperidinyl) benzoxazinorifamycin (compound 13), 25-O-deacetyl-3'-hydroxy-5'-(4-(2-methylpropyl)carbamyl-1-piperidinyl) benzoxazinorifamycin (compound 14), 25-O-deacetyl-3'-hydroxy-5'-[(4aR,7aR)-octahydro-6H-pyrrolo[3,4-b]pyridin-6-yl]benzoxazinorifamycin (compound 15), 25-O-deacetyl-3'-hydroxy-5'-(3,8-diazabicyclo[3.2.1]octan-3-yl) benzoxazinorifamycin (compound 16), 3'-hydroxy-5'-(4-N,N-dimethylamino-1-piperidinyl)benzoxazinorifamycin (compound 17), 25-O-deacetyl-3'-hydroxy-5'-(4-N,N dimethylamino-1-piperidinyl)benzoxazinorifamycin (compound 18), 5'-(4-ethylcarbamyl-1-piperidinyl)-N'-methyl-benzodiazinorifamycin (compound 19), 25-O-deacetyl-3'-hydroxy-5'-[6-amino-(1R,5S)-3-azabicyclo[3.1.0]hex-3-yl] benzoxazinorifamycin (compound 20), 3'-hydroxy-5'-[6-ethylcarbamyl-(1R,5s)-3-azabicyclo[3.1.0]hex-3-yl] benzoxazinorifamycin (compound 21), 3'-hydroxy-5'-[4-isopropylcarbamyl-1-piperidinyl]benzoxazinorifamycin (compound 22), 3'-hydroxy-5'-[4-trifluoromethylsulfonyl-1-piperidinyl]benzoxazinorifamycin (compound 23), 3'-hydroxy-5'-[4-butanamide-1-piperidinyl]benzoxazinorifamycin (compound 24), 3'-hydroxy-5'-[4-methylsulfonyl-1-piperidinyl]benzoxazinorifamycin (compound 25), 25-O-deacetyl-3'-hydroxy-5'-[4-propyluryl-1-piperidinyl] benzoxazinorifamycin (compound 26), 25-O-deacetyl-3'-hydroxy-5'-[4-methylsulfonyl-1-piperidinyl] benzoxazinorifamycin (compound 27), 3'-hydroxy-5'-[4-propyluryl-1-piperidinyl]benzoxazinorifamycin (compound 28), 25-O-deacetyl-3'-hydroxy-5'-[4-isopropylcarbamyl-1-piperidinyl]benzoxazinorifamycin (compound 29), 25-O-deacetyl-3'-hydroxy-5'-[4-methylcarbamyl-1-piperidinyl] benzoxazinorifamycin (compound 30), 25-O-deacetyl-5'-(4-ethylcarbamyl-1-piperidinyl)-N'-methylbenzdiazinorifamycin (compound 31),3'-hydroxy-5'-[4-methylcarbamyl-1-piperidinyl]benzoxazinorifamycin (compound 32),3'-hydroxy-5'-[4-amino-1-piperidinyl]benzoxazinorifamycin (compound 33),3'-hydroxy-5'-[4-ethyluryl-1-piperidinyl]benzoxazinorifamycin (compound 34), 3'-hydroxy-5'-[4-propylsulfonyl-1-piperidinyl]benzoxazinorifamycin (compound 35), 25-O-deacetyl-3'-hydroxy-5'-[4-butanamide-1-piperidinyl]benzoxazinorifamycin (compound 36), 25-O-deacetyl-3'-hydroxy-5'-[4-ethyluryl-1-piperidinyl]benzoxazinorifamycin (compound 37), 25-O-deacetyl-3'-hydroxy-5'-[4-trifluoromethylsulfonyl-1-piperidinyl]benzoxazinorifamycin (compound 38), 25-O-deacetyl-3'-hydroxy-5'-[4-amino-1-piperidinyl] benzoxazinorifamycin (compound 39),3'-hydroxy-5'-[1-ethylcarbamyl-(4aR,7aR)-octahydro-6H-pyrrolo[3,4-b]pyridin-6-yl]benzoxazinorifamycin (compound 40),3'-hydroxy-5'-[1-ethylcarbamyl-(4aS,7aS)-octahydro-6H-pyrrolo[3,4-b]pyridin-6-yl]benzoxazinorifamycin,3'-hydroxy-5'-[4-methoxyethylcarbamyl-1-piperidinyl] benzoxazinorifamycin (compound 41), 25-O-deacetyl-3'-hydroxy-5'-[1-ethylcarbamyl-(4aR,7aR)-octahydro-6H-pyrrolo[3,4-b]pyridin-6-yl]benzoxazinorifamycin (compound 42), 25-O-deacetyl-3'-hydroxy-5'-[1-ethylcarbamyl-(4aS,7aS)-octahydro-6H-pyrrolo[3,4-b]pyridin-6-yl]benzoxazinorifamycin, 25-O-deacetyl-3'-hydroxy-5'-[4-acetamide-1-piperidinyl]benzoxazinorifamycin (compound 43),3'-hydroxy-5'-[4-acetyl-1-piperidinyl]benzoxazinorifamycin (compound 44), 3'-hydroxy-5'-[4-S-methylthiocarbamyl-1-piperidinyl]benzoxazinorifamycin (compound 45), 25-O-deacetyl-3'-hydroxy-5'-[1-acetyl-(4aR,7aR)-octahydro-6H-pyrrolo[3,4-b]pyridin-6-yl]benzoxazinorifamycin (compound 46), 25-O-deacetyl-3'-hydroxy-5'-[1-acetyl-(4aS,7aS)-octahydro-6H-pyrrolo[3,4-b]pyridin-6-yl]benzoxazinorifamycin, 3'-hydroxy-5'-[-acetyl-(4aR,7aR)-octahydro-6H-pyrrolo[3,4-b]pyridin-6-yl]

benzoxazinorifamycin (compound 47), 3'-hydroxy-5'-[1-acetyl-(4aS,7aS)-octahydro-6H-pyrrolo[3,4-b]pyridin-6-yl]benzoxazinorifamycin, 3'-hydroxy-5,'-[4-(2,2-dimethylethyl)carbamyl-1-piperidinyl]benzoxazinorifamycin (compound 48), 3'-hydroxy-5'-[4-(4-(S-methylthiocarbamyl)-1-piperidinylcarbonyl)amino-1-piperidinyl]benzoxazinorifamycin (compound 49), 3'-hydroxy-5'-[4-(4-methylpiperazinylcarbonyl)amino-1-piperidinyl]benzoxazinorifamycin (compound 50), 3'-hydroxy-5'-[4-ethylcarbamylmethyl-1-piperidinyl]benzoxazinorifamycin (compound 51), 25-O-deacetyl-3'-hydroxy-5'-[4-(2,2-dimethylethyl)carbamyl-1-piperidinyl]benzoxazinorifamycin (compound 52), 3'-hydroxy-5'-[6-N,N-dimethylamino-(1R,5S)-3-azabicyclo[3.1.0]hex-3-yl]benzoxazinorifamycin (compound 53), 3'-hydroxy-5'-[6-N,N-dimethylamino-(1R,5S)-3-azabicyclo[3.1.0]hex-3-yl]benzoxazinorifamycin (compound 54), 3'-hydroxy-5'-[4-acetylaminomethyl-1-piperidinyl]benzoxazinorifamycin (compound 55), 25-O-deacetyl-3'-hydroxy-5'-[4-acetylaminomethyl-1-piperidinyl]benzoxazinorifamycin (compound 56), 3'-hydroxy-5'-[4-phenyl-1-piperidinyl]benzoxazinorifamycin (compound 57), 3'-hydroxy-5'-[1-methyl-(4aS,7aS)-octahydro-6H-pyrrolo[3,4-b]pyridin-6-yl]benzoxazinorifamycin (compound 58), 3'-hydroxy-5'-[1-methyl-(4aR,7aR)-octahydro-6H-pyrrolo[3,4-b]pyridin-6-yl]benzoxazinorifamycin, 25-O-deacetyl-3'-hydroxy-5'-[1-methyl-(4aS,7aS)-octahydro-6H-pyrrolo[3,4-b]pyridin-6-yl]benzoxazinorifamycin (compound 59), 25-O-deacetyl-3'-hydroxy-5'-[1-methyl-(4aR,7aR)-octahydro-6H-pyrrolo[3,4-b]pyridin-6-yl]benzoxazinorifamycin, 25-O-deacetyl-3'-hydroxy-5'-[4-ethylcarbamylmethyl-1-piperidinyl]benzoxazinorifamycin (compound 60), 3'-hydroxy-5'-[4-(2-hydroxyethyl)-1-piperidinyl]benzoxazinorifamycin (compound 61), 25-O-deacetyl-3'-hydroxy-5'-[4-phenyl-1-piperidinyl]benzoxazinorifamycin (compound 62), 25-O-deacetyl-3'-hydroxy-5'-[4-methoxyethylcarbamyl-1-piperidinyl]benzoxazinorifamycin (compound 63), 5'-[(3R,5S)-3,5-dimethyl-1-piperazinyl]benzthiazinorifamycin (compound 64), 5'-[(3S,5R)-3,5-dimethyl-1-piperazinyl]benzthiazinorifamycin, 25-O-deacetyl-5'-[(3R,5S)-3,5-dimethyl-1-piperazinyl]benzthiazinorifamycin (compound 65), 25-O-deacetyl-5'-[(3S,5R)-3,5-dimethyl-1-piperazinyl]benzthiazinorifamycin, 25-O-deacetyl-3'-hydroxy-5'-[4-(2-hydroxyethyl)-1-piperidinyl]benzoxazinorifamycin (compound 66), 25-O-deacetyl-3'-hydroxy-5'-[4-propylsulfonyl-1-piperidinyl]benzoxazinorifamycin (compound 67), 5'-[(2S,5R)-4-(cyclopropylmethyl)-2,5-dimethylpiperazinyl]benzthiazinorifamycin (compound 68), 5'-[(2R,5S)-4-(cyclopropylmethyl)-2,5-dimethylpiperazinyl]benzthiazinorifamycin, 5'-[4-N,N-dimethylamino-1-piperidinyl]benzthiazinorifamycin (compound 69), 25-O-deacetyl-5'-[(2S,5R)-4-(cyclopropylmethyl)-2,5-dimethylpiperazinyl]benzthiazinorifamycin (compound 70), 25-O-deacetyl-5'-[(2R,5S)-4-(cyclopropylmethyl)-2,5-dimethylpiperazinyl]benzthiazinorifamycin, 3'-hydroxy-5'-[4-methyl-4-N,N-dimethylamino-1-piperidinyl]benzoxazinorifamycin (compound 71), 3'-hydroxy-5'-[4-methyl-4-acetylamino-1-piperidinyl]benzoxazinorifamycin (compound 72), 25-O-deacetyl-3'-hydroxy-5'-[4-methyl-4-N,N-dimethylamino-1-piperidinyl]benzoxazinorifamycin (compound 73), 25-O-deacetyl-3'-hydroxy-5'-[4-methyl-4-acetylamino-1-piperidinyl]benzoxazinorifamycin (compound 74), 3'-hydroxy-5'-[(3R)-N,N-dimethylamino-1-pyrrolidinyl]benzoxazinorifamycin (compound 75), 3'-hydroxy-5'-[(3S)-N,N-dimethylamino-1-pyrrolidinyl]benzoxazinorifamycin, 5'-[(8aS)octahydropyrrolo[1,2-a]pyrazin-2-yl]benzthiazinorifamycin (compound 76), 5'-[(8aR)octahydropyrrolo[1,2-a]pyrazin-2-yl]benzthiazinorifamycin, 25-O-deacetyl-5'-[(8aS)octahydropyrrolo[1,2-a]pyrazin-2-yl]benzthiazinorifamycin (compound 77), 25-O-deacetyl-5'-[(8aR)octahydropyrrolo[1,2-a]pyrazin-2-yl]benzthiazinorifamycin (compound 78), or 25-O-deacetyl-3'-hydroxy-5'-[3-hydroxy-1-azetidinyl]benzoxazinorifamycin (compound 79).

As used herein, the terms "alkyl" and the prefix "alk-" are inclusive of both straight chain and branched chain saturated or unsaturated groups, and of cyclic groups, i.e., cycloalkyl and cycloalkenyl groups. Unless otherwise specified, acyclic alkyl groups are from 1 to 6 carbons. Cyclic groups can be monocyclic or polycyclic and preferably have from 3 to 8 ring carbon atoms. Exemplary cyclic groups include cyclopropyl, cyclopentyl, cyclohexyl, and adamantyl groups. Alkyl groups may be substituted with one or more substituents or unsubstituted. Exemplary substituents include alkoxy, aryloxy, sulfhydryl, alkylthio, arylthio, halogen, alkylsilyl, hydroxyl, fluoroalkyl, perfluoroalkyl, amino, aminoalkyl, disubstituted amino, quaternary amino, hydroxyalkyl, carboxyalkyl, and carboxyl groups. When the prefix "alk" is used, the number of carbons contained in the alkyl chain is given by the range that directly precedes this term, with the number of carbons contained in the remainder of the group that includes this prefix defined elsewhere herein. For example, the term "$C_1$-$C_4$ alkaryl" exemplifies an aryl group of from 6 to 18 carbons attached to an alkyl group of from 1 to 4 carbons.

By "aryl" is meant a carbocyclic aromatic ring or ring system. Unless otherwise specified, aryl groups are from 6 to 18 carbons. Examples of aryl groups include phenyl, naphthyl, biphenyl, fluorenyl, and indenyl groups.

By "heteroaryl" is meant an aromatic ring or ring system that contains at least one ring hetero-atom (e.g., O, S, Se, N, or P). Unless otherwise specified, heteroaryl groups are from 1 to 9 carbons. Heteroaryl groups include furanyl, thienyl, pyrrolyl, imidazolyl, pyrazolyl, oxazolyl, isoxazolyl, thiazolyl, isothiazolyl, triazolyl, tetrazolyl, oxadiazolyl, oxatriazolyl, pyridyl, pyridazyl, pyrimidyl, pyrazyl, triazyl, benzofuranyl, isobenzofuranyl, benzothienyl, indole, indazolyl, indolizinyl, benzisoxazolyl, quinolinyl, isoquinolinyl, cinnolinyl, quinazolinyl, naphtyridinyl, phthalazinyl, phenanthrolinyl, purinyl, and carbazolyl groups.

By "heterocycle" is meant a non-aromatic ring or ring system that contains at least one ring heteroatom (e.g., O, S, Se, N, or P). Unless otherwise specified, heterocyclic groups are from 2 to 9 carbons. Heterocyclic groups include, for example, dihydropyrrolyl, tetrahydropyrrolyl, piperazinyl, pyranyl, dihydropyranyl, tetrahydropyranyl, dihydrofuranyl, tetrahydrofuranyl, dihydrothiophene, tetrahydrothiophene, and morpholinyl groups.

Aryl, heteroaryl, or heterocyclic groups may be unsubstituted or substituted by one or more substituents selected from the group consisting of $C_{1-6}$ alkyl, hydroxy, halo, nitro, $C_{1-6}$ alkoxy, $C_{1-6}$ alkylthio, trifluoromethyl, $C_{1-6}$ acyl, arylcarbonyl, heteroarylcarbonyl, nitrile, $C_{1-6}$ alkoxycarbonyl, alkaryl (where the alkyl group has from 1 to 4 carbon atoms) and alkheteroaryl (where the alkyl group has from 1 to 4 carbon atoms).

By "alkoxy" is meant a chemical substituent of the formula —OR, where R is an alkyl group. By "aryloxy" is meant a chemical substituent of the formula —OR', where R' is an aryl group. By "alkaryl" is meant a chemical substituent of the formula —RR', where R is an alkyl group and R' is an aryl group, By "alkheteraryl" is meant a chemical substituent of the formula RR", where R is an alkyl group and R" is a heteroaryl group.

By "halide" or "halogen" or "halo" is meant bromine, chlorine, iodine, or fluorine.

By "non-vicinal O, S, or NR" is meant an oxygen, sulfur, or nitrogen heteroatom substituent in a linkage, where the heteroatom substituent does not form a bond to a saturated carbon that is bonded to another heteroatom.

In structural representations where the chirality of a carbon has been left unspecified, it is to be presumed by one skilled in the art that either chiral form of that stereocenter is possible.

By "benzoxazinorifamycin" is meant a compound described by formula (A):

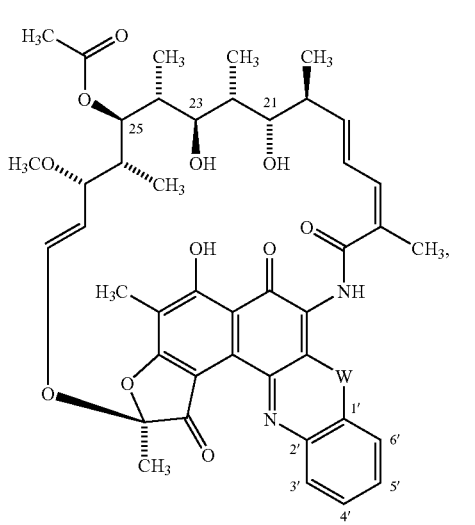

where W is O. By "benzthiazinorifamycin" is meant a compound described by formula (A), where W is S. By "benzdiazinorifamycin" is meant a compound described by formula (A), where W is N-R. For benzdiazinorifamycin, R can be H or an alkyl substituent. When R is an alkyl substituent, it is referred to as N'-R (e.g., N'-methyl) in the naming of the compound. Benzoxazinorifamycin, benzthiazinorifamycin, and benzdiazinorifamycin analogs that contain substituents are numbered according to the numbering provided in formula (A). By "25-O-deacetyl" rifamycin is meant a rifamycin analog in which the acetyl group at the 25-position has been removed. Analogs in which this position is further derivatized are referred to as a "25-O-deacetyl-25-(substituent)rifamycin", in which the nomenclature for the derivatizing group replaces "substituent" in the complete compound name. For example, a benzoxazinorifamycin analog in which the 25-acetyloxy group has been transformed to a carbonate group, with the other side of the carbonate bonded to a 2,3-dihydroxypropyl group, is referred to as a "25-O-deacetyl-25-(2",3"-dihydroxypropylcarbonoxy)-benzoxazinorifamycin."

By "atherosclerosis" is meant the progressive accumulation of smooth muscle cells, immune cells (e.g., lymphocytes, macrophages, or monocytes), lipid products (e.g., lipoproteins, or cholesterol), cellular waste products, calcium, or other substances within the inner lining of an artery, resulting in the narrowing or obstruction of the blood vessel and the development of atherosclerosis-associated diseases. Atherosclerosis is typically manifested within large and medium-sized arteries, and is often characterized by a state of chronic inflammation within the arteries.

By "atherosclerosis-associated disease" is meant any disorder that is caused by or is associated with atherosclerosis. Typically, atherosclerosis of the coronary arteries commonly causes coronary artery disease, myocardial infarction, coronary thrombosis, and angina pectoris. Atherosclerosis of the arteries supplying the central nervous system frequently provokes strokes and transient cerebral ischemia. In the peripheral circulation, atherosclerosis causes intermittent claudication and gangrene and can jeopardize limb viability. Atherosclerosis of an artery of the splanchnic circulation can cause mesenteric ischemia. Atherosclerosis can also affect the kidneys directly (e.g., renal artery stenosis).

A patient who is being treated for an atherosclerosis-associated disease is one who a medical practitioner has diagnosed as having such a disease. Diagnosis may be by any suitable means. Methods for diagnosing atherosclerosis by measuring systemic inflammatory markers are described, for example, in U.S. Pat. No. 6,040,147, hereby incorporated by reference. Diagnosis and monitoring may employ an electrocardiogram, chest X-ray, echocardiogram, cardiac catheterization, ultrasound (for the measurement of vessel wall thickness), or measurement of blood levels of CPK, CPK-MB, myoglobin, troponin, homocysteine, or C-reactive protein. A patient in whom the development of an atherosclerosis-associated disease is being prevented is one who has not received such a diagnosis. One in the art will understand that these patients may have been subjected to the same tests (electrocardiogram, chest X-ray, etc.) or may have been identified, without examination, as one at high risk due to the presence of one or more risk factors (e.g., family history, hypertension, diabetes mellitus, high cholesterol levels). Thus, prophylactic administration of a rifamycin analog is considered to be preventing the development of an atherosclerosis-associated disease.

An atherosclerosis-associated disease has been treated or prevented when one or more tests of the disease (e.g., any of the those described above) indicate that the patient's condition has improved or the patient's risk reduced. In one example, a reduction in C-reactive protein to normal levels indicates that an atherosclerosis-associated disease has been treated or prevented.

An alternative means by which treatment or prevention is assessed includes determination of the presence of an infection of C. pneumoniae. Any suitable method may be employed (e.g., determination of C. pneumoniae in blood monocytes or in the atheroma itself (e.g., in macrophages or foam cells present in the fatty streak), or detection of C. pneumoniae DNA, RNA, or antibodies to C. pneumoniae in a biological sample from the patient).

By "debris" is meant the mucoid exudate or desquamated epithelium in an infected ear of a patient having an ear infection.

By "ear wick" is meant a sponge, cotton, gauze, compressed hydroxycellulose, or any other material used to increase the penetration of rifamycin to the infected otic area. The ear wick is typically inserted into the canal under direct vision. Its presence helps wick eardrops along the canal, hold the solution in contact with the skin of the canal, and apply pressure to the canal skin.

By "granulation tissue" is meant the highly vascularized tissue that replaces the initial fibrin clot in a wound. Vascularization is a result of an ingrowth of capillary endothelium from the surrounding vasculature. The tissue is also rich in fibroblasts and leucocytes.

"Antibiotic-associated bacterial diarrhea" means the condition wherein antibiotic therapy disturbs the balance of the microbial flora of the gut, allowing pathogenic organisms such as *C. difficile* to flourish. These organisms cause diarrhea. Antibiotic-associated bacterial diarrhea includes such conditions as *C. difficile* associated diarrhea (CDAD) and pseudomembranous colitis.

"Pseudomembranous colitis," also known as pseudomembranous enterocolitis or enteritis, means the inflammation of the mucous membrane of both small and large intestine with the formation and passage of pseudomembranous material (composed of fibrin, mucous, necrotic epithelial cells and leukocytes) in the stools.

By "autoimmune disease" is meant a disease arising from an immune reaction against self-antigens and directed against the individual's own tissues. Examples of autoimmune diseases include but are not limited to systemic lupus erythematosus, rheumatoid arthritis, myasthenia gravis, and Graves' disease.

By "bacteria" is meant a unicellular prokaryotic microorganism that usually multiplies by cell division.

By "bacterial infection" is meant the invasion of a host animal by pathogenic bacteria. For example, the infection may include the excessive growth of bacteria that are normally present in or on the body of an animal or growth of bacteria that are not normally present in or on the animal. More generally, a bacterial infection can be any situation in which the presence of a bacterial population(s) is damaging to a host animal. Thus, an animal is "suffering" from a bacterial infection when an excessive amount of a bacterial population is present in or on the animal's body, or when the presence of a bacterial population(s) is damaging the cells or other tissue of the animal.

By "chronic disease" is meant a disease that is inveterate, of long continuance, or progresses slowly, in contrast to an acute disease, which rapidly terminates. A chronic disease may begin with a rapid onset or in a slow, insidious manner but it tends to persist for several weeks, months or years, and has a vague and indefinite termination.

By "immunocompromised" is meant a person who exhibits an attenuated or reduced ability to mount a normal cellular or humoral defense to challenge by infectious agents, e.g., viruses, bacterial, fungi, and protozoa. Persons considered immunocompromised include malnourished patients, patients undergoing surgery and bone narrow transplants, patients undergoing chemotherapy or radiotherapy, neutropenic patients, HIV-infected patients, trauma patients, burn patients, patients with chronic or resistant infections such as those resulting from myelodysplastic syndrome, and the elderly, all of who may have weakened immune systems.

By "inflammatory disease" is meant a disease state characterized by (1) alterations in vascular caliber that lead to an increase in blood flow, (2) structural changes in the microvasculature that permit the plasma proteins and leukocytes to leave the circulation, and (3) emigration of the leukocytes from the microcirculation and their accumulation in the focus of injury. The classic signs of acute inflammation are erythema, edema, tenderness (hyperalgesia), and pain. Chronic inflammatory diseases are characterized by infiltration with mononuclear cells (e.g., macrophages, lymphocytes, and plasma cells), tissue destruction, and fibrosis. Non-limiting examples of inflammatory disease include asthma, coronary artery disease, arthritis, conjunctivitis, lymphogranuloma venerum, and salpingitis.

By "intracytoplasmic inclusion" is meant a replicating reticulate body (RB) that has no cell wall. Such inclusions may be detected, for example, through chlamydiae sample isolation and propagation on mammalian cell lines, followed by fixing and staining using one of a variety of staining methods including Giemsa staining, iodine staining, and immunofluorescence. These inclusions have a typical round or oval appearance.

By "persistent bacterial infection" is meant an infection that is not completely eradicated through standard treatment regimens using anti-bacterial agents. Persistent bacterial infections are caused by bacteria capable of establishing a cryptic or latent phase of infection and may be classified as such by culturing the bacteria from a patient and demonstrating bacterial survival in vitro in the presence of anti-bacterial agents or by determination of anti-bacterial treatment failure in a patient. As used herein, a persistent infection in a patient includes any recurrence of chlamydial infection, after receiving anti-bacterial treatment, from the same species (e.g., *C. trachomatis*) more than two times over the period of two or more years or the detection of the cryptic phase of the infection in the patient by the methods described. An in vivo persistent infection can be identified through the use of a reverse transcriptase polymerase chain reaction (RT-PCR) to demonstrate the presence of 16S rRNA transcripts in bacterially infected cells after treatment with anti-bacterial agents (Antimicrob. Agents Chemother. 12:3288-3297, 2000).

By "replicating phase" is meant the phase of the bacterial cell cycle characterized by the presence of an RB. The RB is the actively replicating form of the Chlamydia. It contains no cell wall and is detected as an inclusion in the cell.

As used herein, the term "treating" refers to administering or prescribing a pharmaceutical composition for prophylactic and/or therapeutic purposes. To "prevent disease" refers to prophylactic treatment of a patient who is not yet ill, but who is susceptible to, or otherwise at risk of, a particular disease. To "treat disease" or use for "therapeutic treatment" refers to administering treatment to a patient already suffering from a disease to improve the patient's condition. Thus, in the claims and embodiments, treating is the administration to an animal either for therapeutic or prophylactic purposes. An ear infection has been treated when one or more tests of the disease (e.g., any of the those described below) indicate that the patient's condition has improved. The detection of an infection may be done by a pneumatic otoscopic examination of the patient, or by a reduction in infection-associated symptoms in the patient (e.g., inflammation of ear drums, redness of ear drums, presence of fluid in ears). Reduction of symptoms may also be determined, for example, by audiogram to check recovery from hearing loss. Prophylactic administration of a rifamycin of the invention is considered to be preventing the development of an ear infection.

By "effective amount" is meant the amount of a compound required to treat or prevent an infection. The effective amount of active compound(s) used to practice the present invention for therapeutic or prophylactic treatment of conditions caused by or contributed to by a microbial infection varies depending upon the manner of administration, the age, body weight, and general health of the subject. Ultimately, the attending physician or veterinarian will decide the appropriate amount and dosage regimen. Such amount is referred to as an "effective" amount.

The term "microbial infection" refers to the invasion of the host animal by pathogenic microbes. This includes the excessive growth of microbes that are normally present in or on the body of an animal. More generally, a microbial infection can be any situation in which the presence of a microbial population(s) is damaging to a host animal. Thus, an animal is "suffering" from a microbial infection when excessive numbers of a microbial population are present in or on an animal's body, or when the presence of a microbial population(s) is damaging the cells or other tissue of an animal.

The term "microbes" includes, for example, bacteria, fungi, yeasts, viruses and protozoa.

By "intracellular pathogen" is meant an infection by any facultative or obligate intracellular microbe.

By "obligate intracellular pathogen" is meant a microbe that must use an intracellular location (e.g., a host cell) in order to replicate.

By "facultative intracellular pathogen" is meant a microbe that is able to survive within an intracellular location (e.g., a host cell), but does not require an intracellular environment to replicate.

The term "administration" or "administering" refers to a method of giving a dosage of a pharmaceutical composition to an animal, where the method is, e.g., topical, oral, intravenous, intraperitoneal, or intramuscular. The preferred method of administration can vary depending on various factors, e.g., the components of the pharmaceutical composition, site of the potential or actual disease, and severity of disease.

The terms "animal," "subject," and "patient" specifically include humans, cattle, horses, dogs, cats, and birds, but also can include many other species.

DETAILED DESCRIPTION

We have discovered that rifamycin analogs are useful for treating or preventing a variety of microbial infections. The compounds of the present invention are described by formula (I):

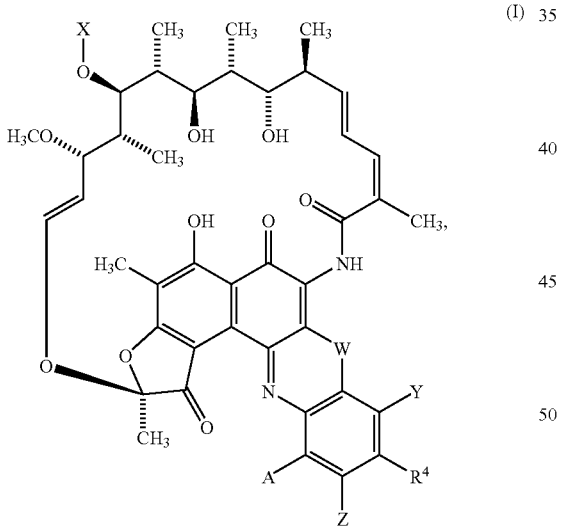

or a pharmaceutically acceptable salt thereof, wherein
A is H, OH, O—($C_1$-$C_6$ alkyl), or O—($C_1$-$C_4$ alkaryl);
W is O, S, or $NR^1$, wherein $R^1$ is H or $C_1$-$C_6$ alkyl;
X is H or $COR^2$, wherein $R^2$ is $C_1$-$C_6$ alkyl, which can be substituted with from 1 to 5 hydroxyl groups, or O—($C_3$-$C_7$ alkyl), which can be substituted with from 1 to 4 hydroxyl groups, wherein each alkyl carbon is bound to no more than one oxygen;
Y is H, $OR^3$, or Hal;
Z is H, $OR^3$, or Hal;
$R^3$ is $C_1$-$C_6$ alkyl; and $R^4$ has the formula:

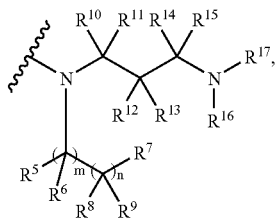

when each of m and n is 1,
each of $R^5$ and $R^6$ is H, or $R^5$ and $R^6$ together are =O;
$R^7$ and $R^{10}$ together form a single bond or a $C_1$-$C_3$ linkage, which optionally contains a non-vicinal O, S, or $N(R^{23})$, $R^7$ and $R^{12}$ together form a single bond or a $C_1$-$C_2$ linkage, which optionally contains a non-vicinal O, S, or $N(R^{23})$, or $R^7$ and $R^{14}$ together form a single bond or a $C_1$ linkage, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl;
$R^8$ is H, $C_1$-$C_6$ alkyl, or $C_1$-$C_4$ alkaryl, or $R^8$ and $R^{12}$ together form a single bond, or $R^8$ and $R^9$ together are =N—O $R^{18}$, wherein $R^{18}$ is H, $C_1$-$C_6$ alkyl, or $C_1$-$C_4$ alkaryl;
$R^9$ is H, $C_1$-$C_6$ alkyl, or $C_1$-$C_4$ alkaryl, or $R^9$ and $R^8$ together are =N—$OR^{18}$;
$R^{10}$ is H, $C_1$-$C_6$ alkyl, or $C_1$-$C_4$ alkaryl, or $R^{10}$ and $R^7$ together form a single bond or a $C_1$-$C_3$ linkage, which optionally contains a non-vicinal O, S, or $N(R^{23})$, or $R^{10}$ and $R^{16}$ together form a $C_1$-$C_2$ alkyl linkage, which optionally contains a non-vicinal O, S, or $N(R^{23})$, or $R^{10}$ and $R^{17}$ together form a $C_1$-$C_3$ alkyl linkage, which optionally contains a non-vicinal O, S, or $N(R^{23})$, or $R^{10}$ and $R^{11}$ together are =O, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl;
$R^{11}$ is H, or $R^{11}$ and $R^{10}$ together are =O;
$R^{12}$ is H, $C_1$-$C_6$ alkyl, or $C_1$-$C_4$ alkaryl, or $R^{12}$ and $R^7$ together form a single bond or a $C_1$-$C_2$ linkage, which optionally contains a non-vicinal O, S, or $N(R^{23})$, or $R^{12}$ and $R^8$ together form a single bond, or $R^{12}$ and $R^{16}$ together form a $C_2$-$C_4$ alkyl linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl;
each of $R^{13}$ and $R^{15}$ is H, $C_1$-$C_6$ alkyl, or $C_1$-$C_4$ alkaryl;
$R^{14}$ is H, $C_1$-$C_6$ alkyl, or $C_1$-$C_4$ alkaryl, or $R^{14}$ and $R^7$ together form a single bond or a $C_1$ linkage;
$R^{16}$ is H, $C_1$-$C_6$ alkyl, $C_1$-$C_6$ alkoxy, $C_6$-$C_{12}$ aryl, heteroaryl, $C_1$-$C_4$ alkaryl, or $C_1$-$C_4$ alkheteroaryl, or $R^{16}$ and $R^{12}$ together form a $C_2$-$C_4$ alkyl linkage, which optionally contains a non-vicinal O, S, or $N(R^{23})$, or $R^{16}$ and $R^{10}$ together form a $C_1$-$C_2$ alkyl linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl; and $R^{17}$ is H, $C_1$-$C_6$ alkyl, $COR^{19}$, $CO_2R^{19}$, or $CONHR^{19}$, $CSR^{19}$, $COSR^{19}$, $CSOR^{19}$, $CSNHR^{19}$, $SO_2R^{19}$, or $SO_2NHR^{19}$, wherein $R^{19}$ is $C_1$-$C_6$ alkyl, $C_6$-$C_{12}$ aryl, $C_1$-$C_4$ alkaryl, heteroaryl, or $C_1$-$C_4$ alkheteroaryl, or $R^{17}$ and $R^{10}$ together from $C_1$-$C_3$ alkyl linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_2$-$C_6$ alkyl, $C_6$-$C_{12}$ aryl, $C_1$-$C_4$ alkaryl, heteroaryl, or $C_1$-$C_4$ alkheteroaryl;

or when m is 0 and n is 1, $R^7$ and $R^{10}$ together form a single bond or a $C_1$-$C_4$ linkage, which optionally contains a non-vicinal O, S, or $N(R^{23})$, $R^7$ and $R^{12}$ together form a single bond or a $C_1$-$C_3$ linkage, which optionally contains a non-vicinal O, S, or $N(R^{23})$, or $R^7$ and $R^{14}$ together form a single bond or a $C_1$-$C_2$ linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl;

each of $R^8$, $R^9$, and $R^{11}$ is H;

$R^{15}$ is H, $C_1$-$C_6$ alkyl, or $C_1$-$C_4$ alkaryl;

$R^{10}$ is H or $R^{10}$ and $R^7$ together form a single bond or a $C_1$-$C_4$ linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl;

$R^{12}$ is H, $C_1$-$C_6$ alkyl, or $C_1$-$C_4$ alkaryl, or $R^{12}$ and $R^7$ together form a single bond or a $C_1$-$C_3$ linkage, which optionally contains a non-vicinal O, S, or $N(R^{23})$, $R^{12}$ and $R^{13}$ together form a —$CH_2CH_2$— linkage, or $R^{12}$ and $R^{16}$ together form a $C_2$-$C_4$ alkyl linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl;

$R^{13}$ is H, $C_1$-$C_6$ alkyl, $C_1$-$C_4$ alkaryl, or $R^{13}$ and $R^{12}$ together form a —$CH_2CH_2$— linkage;

$R^{14}$ is H, $C_1$-$C_6$ alkyl, or $C_1$-$C_4$ alkaryl, or $R^{14}$ and $R^7$ together form a single bond or a $C_1$-$C_2$ linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl;

$R^{16}$ is H, $C_1$-$C_6$ alkyl, $C_1$-$C_6$ alkoxy, $C_6$-$C_{12}$ aryl, heteroaryl, $C_1$-$C_4$ alkaryl, or $C_1$-$C_4$ alkheteroaryl, or $R^{16}$ and $R^{12}$ together form a $C_2$-$C_4$ alkyl linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl; and $R^{17}$ is H, $C_1$-$C_6$ alkyl, $COR^{19}$, $CO_2R^{19}$, or $CONHR^{19}$, $CSR^{19}$, $COSR^{19}$, $CSOR^{19}$, $CSNHR^{19}$, $SO_2R^{19}$, or $SO_2NHR^{19}$, wherein $R^{19}$ is $C_1$-$C_6$ alkyl, $C_6$-$C_{12}$ aryl, $C_1C_4$ alkaryl, heteroaryl, or $C_1$-$C_4$ alkheteroaryl; or A is OH;

X is H;

W, Y, and Z are defined as above; and $R^4$ is selected from the group consisting of:

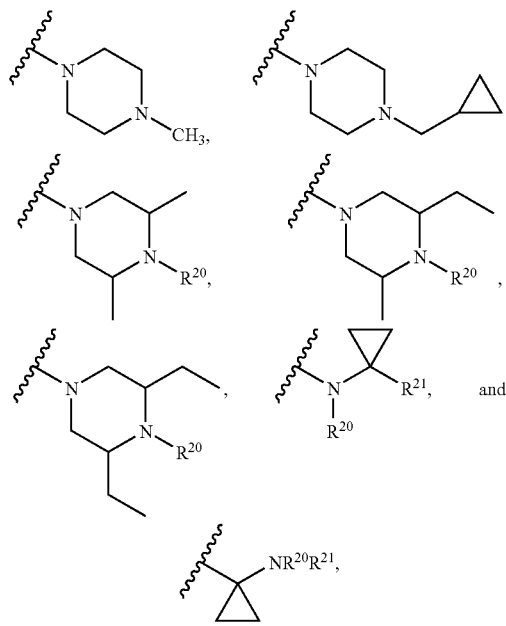

wherein $R^{21}$ is H, $C_1$-$C_6$ alkyl, $C_6$-$C_{12}$ aryl, heteroaryl, $C_1$-$C_4$ alkaryl, or $C_1$-$C_4$ alkheteroaryl, $R^{20}$ is H, $C_1$-$C_6$ alkyl, $COR^{19}$, $CO_2R^{19}$, or $CONHR^{19}$, $CSR^{19}$, $COSR^{19}$, $CSOR^{19}$, $CSNHR^{19}$, $SO_2R^{19}$, or $SO_2NHR^{19}$, wherein $R^{19}$ is $C_1$-$C_6$ alkyl, $C_6$-$C_{12}$ aryl, $C_1$-$C_4$ alkaryl, heteroaryl, or $C_1$-$C_4$ alkheteroaryl; or A is OH;

X is $COCH_3$;

W, Y, and Z are defined as above; and $R^4$ is selected from the group consisting of:

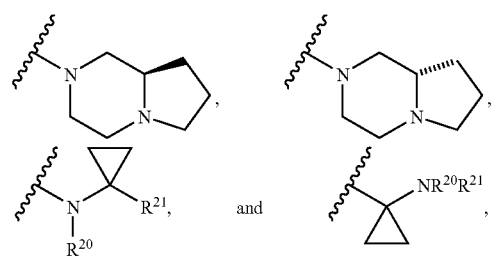

wherein $R^{21}$ is H, $C_1$-$C_6$ alkyl, $C_6$-$C_{12}$ aryl, heteroaryl, $C_1$-$C_4$ alkaryl, or $C_1$-$C_4$ alkheteroaryl, $R^{20}$ is H, $C_1$-$C_6$ alkyl, $COR^{19}$, $CO_2R^{19}$, or $CONHR^{19}$, $CSR^{19}$, $COSR^{19}$, $CSOR^{19}$, $CSNHR^{19}$, $SO_2R^{19}$, or $SO_2NHR^{19}$, wherein $R^{19}$ is $C_1$-$C_6$ alkyl, $C_6$-$C_{12}$ aryl, $C_1$-$C_4$ alkaryl heteroaryl, or $C_1$-$C_4$ alkheteroaryl; or A is H or OH;

X is H or $COCH_3$;

W, Y, and Z are defined as above; and $R^4$ is

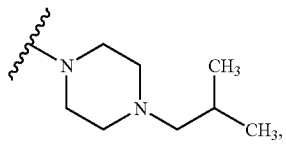

with the proviso that one or both of Y and Z are Hal, or

A is H or OH;
X is H or $COCH_3$;
W, Y, and Z are defined as above; and
$R^4$ is

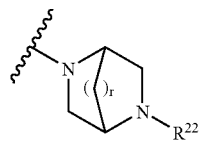 or 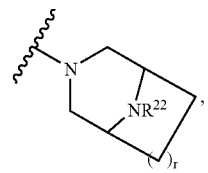

wherein $R^{22}$ is H, $C_1$-$C_6$ alkyl, $C_6$-$C_{12}$ aryl, heteroaryl, $C_1$-$C_4$ alkaryl, $C_1$-$C_4$ alkheteroaryl, $COR^{24}$, $CO_2R^{24}$, $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl, and r is 1-2, or A is H or OH;
X is H or $COCH_3$;
W, Y, and Z are defined as above; and
$R^4$ is

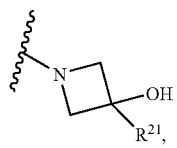

wherein $R^{21}$ is H, $C_1$-$C_6$ alkyl, $C_6$-$C_{12}$ aryl, heteroaryl, $C_1$-$C_4$ alkaryl, or $C_1$-$C_4$ alkheteroaryl, or A is H or OH;
X is H or $COCH_3$;
W, Y, and Z are defined as above; and
$R^4$ is

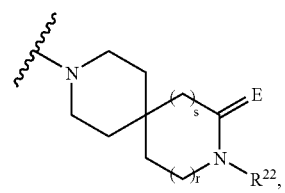 or

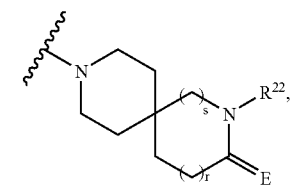

wherein =E is =O or (H,H), $R^{22}$ is H, $C_1$-$C_6$ alkyl, $C_6$-$C_{12}$ aryl, heteroaryl, $C_1$-$C_4$ alkaryl, $C_1$-$C_4$ alkheteroaryl, $COR^{24}$, $CO_2R^{24}$, $CONHR^{24}$, $CSR^{24}$, $COSR^{24}$, $CSOR^{24}$, $CSNHR^{24}$, $SO_2R^{24}$, or $S_2NHR^{24}$, wherein $R^{24}$ is $C_1$-$C_6$ alkyl, $C_6$-$C_{12}$ aryl, $C_1$-$C_4$ alkaryl, heteroaryl, or $C_1$-$C_4$ alkheteroaryl, r is 1-2, and s is 0-1, or A is H or OH;
X is H or $COCH_3$;
W, Y, and Z are as described above;
and $R^4$ is

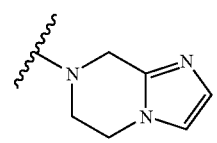 or 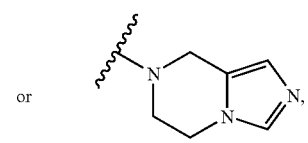

For those compounds in which $R^4$ has the formula:

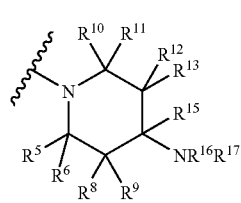

several different ring systems can be constructed from this generic formula. In one example, compounds having formula (A) are constructed when each of m and n is 1 and $R^7$ forms a single bond with $R^{14}$.

(A)

In another example, compounds having formula (B) are constructed when each of m and n is 1, $R^7$ forms a single bond with $R^{14}$, and $R^8$ forms a single bond with $R^{12}$.

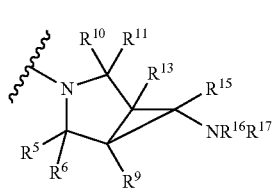

(B)

In another example, compounds having formula (C) are constructed when m is 0 and n is 1, $R^7$ forms a single bond with $R^{14}$, and $R^{12}$ forms a $C_3$ alkyl linkage with $R^{16}$.

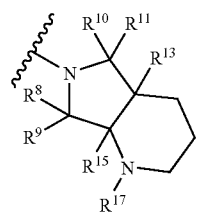

(C)

In another example, compounds having formula (D) are constructed when m is 0, n is 1, and $R^7$ forms a single bond with $R^{14}$.

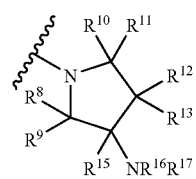

(D)

In another example, compounds having formula (E) are constructed when each of m and n is 1 and $R^7$ forms a single bond with $R^{12}$.

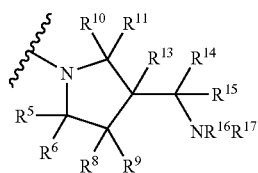

(E)

In another example, compounds having formula (F) are constructed when each of m and n is 1, $R^7$ forms a single bond with $R^{12}$, and $R^8$ forms a $C_1$ linkage with $R^{16}$.

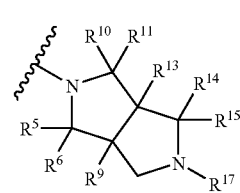

(F)

In yet another example, compounds having formula (G) are constructed when m is 0 and n is 1, $R^7$ forms a single bond with $R^{14}$, and $R^{12}$ forms a $C_2$ alkyl linkage, containing an $NR^{23}$ moiety, with $R^{16}$.

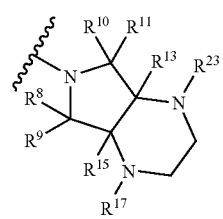

(G)

We have identified a method of preventing, stabilizing, or inhibiting the growth of microbes, or killing microbes. The method involves contacting microbes or a site susceptible to microbial growth with a compound of the invention. Compounds of the present invention can be used to treat, stabilize or prevent a microbial infection in an animal. In this method, the step of contacting microbes or a site susceptible to microbial infection (e.g., a site in or on the body of an animal) with a compound of the invention includes administering to the animal the compound in an amount sufficient to treat, stabilize, or prevent the microbial infection in the animal. In a related aspect, the invention features a method of treating any disease associated with such a microbial infection.

Compounds of the present invention can be used to treat atherosclerosis or diseases associated therewith, sexually transmitted diseases caused, for example, by *C. trachomatis* or *N. gonorrhoeae*, otitis media and other ear infections, antibiotic-associated colitis, gastritis and ulcers associated with an infection of *H. pylori*, Gram-positive infections, community-acquired pneumonia, upper and lower respiratory tract infections, skin and soft tissue infections, bone and joint infections, hospital-acquired lung infections, urinary tract infections, pyelonephritis, intra-abdominal infections, bacteremia, bacterial sepsis, would infections, peritonitis, osteomyelitis, infections after bums, pelvic inflammatory disease, and diseases associated with chronic infections.

Atherosclerosis and other Diseases Associated with Chlamydial Infection

An association was previously reported in International Publication No. WO 98/50074 between the cryptic phase of a persistent chlamydial infection of body fluids and/or tissues and several chronic disease syndromes of previously unknown etiology in humans. To date, these diseases include, but are not limited to, atherosclerosis, multiple sclerosis, rheumatoid arthritis, inflammatory bowel disease, interstitial cystitis, fibromyalgia, autonomic nervous dysfunction (neural-mediated hypotension); pyoderma gangrenosum, and chronic fatigue syndrome.

As described in International Publication No. WO 98/50074, several lines of evidence have led to the establishment of a link between *Chlamydia* and a broad set of inflammatory, autoimmune, and immune deficiency diseases. These include (i) the association between the cryptic phase of a persistent chlamydial infection of body fluids and/or tissues and several chronic disease syndromes as described above, (ii) published evidence of an association between atherosclerosis and *Chlamydia* (*Circulation*, 96:404-407, 1997), and (iii) an understanding of the impact the persistent infection established by the cryptic phase of chlamydial infections can have on infected cells and the immune system. Thus, the present invention describes methods for treating chronic diseases associated with the cryptic phase of a persistent chlamydial infection, such as autoimmune diseases, inflammatory diseases and diseases that occur in immunocompromised individuals by treating the cryptic phase of the infection in an individual in need thereof, using the rifamycin analogs described herein. Progress of the treatment can be evaluated, using the diagnostic tests described herein, to determine the presence or absence of *Chlamydia*. Physical improvement in the conditions and symptoms typically associated with the disease to be treated can also be evaluated. Based upon these evaluating factors, the physician can maintain or modify the anti-bacterial therapy accordingly.

The therapies described herein can be used for the treatment of chronic immune and autoimmune diseases when patients are demonstrated to have a *Chlamydia* load by the methods of detection described above. These diseases include, but are not limited to, chronic hepatitis, systemic lupus erythematosus, arthritis, thyroidosis, scleroderma, diabetes mellitus, Graves' disease, Beschet's disease, and graft versus host disease (graft rejection). The therapies of this invention can also be used to treat any disorders in which a chlamydial species is a factor or co-factor.

Thus, the present invention can be used to treat a range of disorders in addition to the above immune and autoimmune diseases when demonstrated to be associated with chlamydial infection by the methods of detection described herein; for example, various infections, many of which produce inflammation as primary or secondary symptoms, including, but not limited to, sepsis syndrome, cachexia, circulatory collapse and shock resulting from acute or chronic bacterial infection, acute and chronic parasitic and/or infectious diseases from bacterial, viral or fungal sources, such as a HIV, AIDS (including symptoms of cachexia, autoimmune disorders, AIDS dementia complex and infections) can be treated, as well as Wegners Granulomatosis.

Among the various inflammatory diseases, there are certain features that are generally agreed to be characteristic of the inflammatory process. These include fenestration of the microvasculature, leakage of the elements of blood into the interstitial spaces, and migration of leukocytes into the inflamed tissue. On a macroscopic level, this is usually accompanied by the familiar clinical signs of erythema, edema, tenderness (hyperalgesia), and pain. Inflammatory diseases, such as chronic inflammatory pathologies and vascular inflammatory pathologies, including chronic inflammatory pathologies such as aneurysms, hemorrhoids, sarcoidosis, chronic inflammatory bowel disease, ulcerative colitis, and Crohn's disease and vascular inflammatory pathologies, such as, but not limited to, disseminated intravascular coagulation, atherosclerosis, and Kawasaki's pathology are also suitable for treatment by methods described herein. The invention can also be used to treat inflammatory diseases such as coronary artery disease, hypertension, stroke, asthma, chronic hepatitis, multiple, sclerosis, peripheral neuropathy, chronic or recurrent sore throat, laryngitis, tracheobronchitis, chronic vascular headaches (including migraines, cluster headaches and tension headaches), and pneumonia.

Treatable disorders when associated with a chlamydial infection also include, but are not limited to, neurodegenerative diseases, including, but not limited to, demyelinating diseases, such as multiple sclerosis and acute transverse myelitis; extrapyramidal and cerebellar disorders, such as lesions of the corticospinal system; disorders of the basal ganglia or cerebellar disorders; hyperkinetic movement disorders such as Huntington's Chorea and senile chorea; drug-induced movement disorders, such as those induced by drugs which block CNS dopamine receptors; hypokinetic movement disorders, such as Parkinson's disease; progressive supranucleo palsy; cerebellar and spinocerebellar disorders, such as astructural lesions of the cerebellum; spinocerebellar degenerations (spinal ataxia, Friedreich's ataxia, cerebellar cortical degenerations, multiple systems degenerations (Mencel, Dejerine-Thomas, Shi-Drager, and Machado Joseph)); and systemic disorders (Refsum's disease, abetalipoprotemia, ataxia, telangiectasia, and mitochondrial multi-system disorder); demyelinating core disorders, such as multiple sclerosis, acute transverse myelitis; disorders of the motor unit, such as neurogenic muscular atrophies (anterior horn cell degeneration, such as amyotrophic lateral sclerosis, infantile spinal muscular atrophy and juvenile spinal muscular atrophy); Alzheimer's disease; Down's Syndrome in middle age; Diffuse Lewy body disease; senile dementia of Lewy body type; Wernicke-Korsakoff syndrome; chronic alcoholism; Creutzfeldt-Jakob disease; subacute sclerosing panencephalitis, Hallerrorden-Spatz disease; and Dementia pugilistica, or any subset thereof.

It is also recognized that malignant pathologies involving tumors or other malignancies, such as, but not limited to leukemias (acute, chronic myelocytic, chronic lymphocytic and/or myelodyspastic syndrome); lymphomas (Hodgkin's and non-Hodgkin's lymphomas, such as malignant lymphomas (Burkitt's lymphoma or mycosis fungoides)); carcinomas (such as colon carcinoma) and metastases thereof, cancer-related angiogenesis; infantile hemangiomas; and alcohol-induced hepatitis. Ocular neovascularization, psoriasis, duodenal ulcers, and angiogenesis of the female reproductive tract can also be treated when demonstrated by the diagnostic procedures described herein to be associated with a chlamydial infection.

Ear Infections

Ear infections typically affect the middle or the external ear and include, for example, otitis media, otitis externa, and infections caused by surgical interventions. Due to multiplicity of secondary complications that arise from ear infections such as hearing loss, the treatment and prevention of such conditions is critical.

Topical administration of a compound of formula (I) is effective in treating or preventing an infection of the ear, such as otitis media or otitis externa. In the case of otitis media or externa, infections are primarily caused by *H. influenza, M. catarhalis, S. pneumoniae, S. pyogenes, S. intermedius, S. epidermidis, S. aureus, S. caprae, S. auriculis, S. capitis, S. haemolytis, P. aeroginosa, P. mirabilis, P. vulgaris, E. faecalis*, or *E. coli*. A compound of formula (I) can be used to treat each of these infections of the ear. The rifamycin analog of formula (I) may, for example, be topically administered to the area of the ear to which surgical intervention was performed or, alternatively, the rifamycin may be administered to the ear of the patient prophylactically, prior to otic surgery, noninvasive otic procedures, or other types of surgery. Exemplary surgical procedures include for example, cochlear implant surgery, tympanoplasty, tympanostomy tube insertion, removal of tumors (e.g., cholesteatoma), or stapedectomy. The compound may be administered to the area of the ear to which surgical intervention will be performed, for example, within seven days, two days, one day, 12 hours, 10 hours, 6 hours, 4 hours, 2 hours, 1 hour, or less than 1 hour prior to or following the surgical intervention. The compositions may be used for acute treatment of temporary conditions, or may be administered chronically.

A compound of formula (I) may be given daily (e.g., once, twice, three times, or four times daily) or less frequently (e.g., once every other day, or once or twice weekly). Typically, patients are administered a dosage consisting of one to four drops of solution containing the compound. The compound may be contained in any appropriate amount in any suitable carrier substance, and is generally present in an amount between 0.001% and 5%, desirably 0.01% and 3%, more desirably 0.1% and 1%, and even more desirably 0.1% and 0.4% by weight of the total volume (w/v) of the composition. The compound is provided in a dosage form that is suitable for topical administration. Thus, a composition containing a compound of formula (I) may be in the form of a solution, aerosol, gel, ointment, nebulizer, or suspension. Alternatively, the rifamycin analog may be administered by placing an impregnated porous media into the external ear canal to the tympanic membrane. The pharmaceutical composition can generally be formulated according to conventional pharmaceutical practice.

Aural Toilet

The external auditory canal and tissues lateral to the infected middle ear often are covered with mucoid exudate or desquamated epithelium. Since topically applied preparations cannot generally penetrate affected tissues until these interposing materials are removed, aural toilet is desirably performed before administering a compound of formula (I). Aural toilet may be performed by a health provider, the patient, or any other individual. Removal of debris may be performed mechanically with the assistance of a microscope and microinstruments. Aural irrigation may also be performed using a solution containing peroxide. The concentration of peroxide should be the highest concentration without causing significant pain, or discomfort, to the patient. As an example, a solution of 50% peroxide and 50% sterile water can be used. Thirty to 40 mL of this solution can be irrigated through the external auditory canal, using a small syringe or bulb-type aspirator. The irrigant solution is allowed to drain out (e.g., for 5-10 minutes) prior to administering a rifamycin of the present invention.

Granulation Tissue

Granulation tissue often fills the middle ear and medial portions of the external auditory canal, and reducing this accumulation is beneficial for resolution of an ear infection. Granulation tissue may also prevent topically applied antimicrobial agents from penetrating to the site of infection, and the amount of granulation tissue is desirably reduced throughout the regimen. Although topical antimicrobial drops can reduce granulation by eliminating infection and by removing the inciting irritating inflammation, the amount of granulation tissue may be reduced using other methods known in the art. For example, topical steroids may hasten the resolution of middle ear granulation, thus improving penetration of topically delivered antibiotics.

Cautery may also be used to reduce the amount of granulation tissue and to reduce its formation. Microbipolar cautery may be administered by a health provider. Chemical cautery, using for example silver nitrate, may also be applied to an infected ear in the form of silver nitrate sticks. Excision of granulation tissue may also be performed by a health care provider with a microscope and microinstruments.

Ear Canal Acidification

In a patient affected with otitis externa, a therapy involving ear canal acidification to restore the physiological acidity of the ear may be performed. The affected ear is administered with a solution containing acetic acid, which may also include a steroid (e.g., hydrocortisone), aluminum acetate, or rubbing alcohol.

Topical Formulations

Pharmaceutical compositions according to the present invention can be formulated for topical administration to the ear of the patient. Patients having an ear infection may be administered with effective amounts of a rifamycin analog of the invention, by means of a solution (e.g., drops), ointment, gel, or aerosol (e.g., nebulizer). The composition is typically administered to the affected otic area by topically applying, for example, one to four drops of a solution or suspension, or a comparable amount of an ointment, gel, or other solid or semisolid composition, once, twice, three times, or more than three times per day. A porous media or an ear wick (e.g., cotton, gauze, or compressed hydroxycellulose) may also be used to increase the penetration of the rifamycin to the infected otic area. The ear wick, which is inserted into the canal under direct vision, is typically a dried sponge that helps wick eardrops along the canal, hold the solution in contact with the skin of the canal and apply pressure to the canal skin. Wicks may be removed at one day, two days, or more than two days, and may be replaced if necessary. Alternatively, the ear wick may itself be impregnated with a rifamycin analog of the invention. These formulations can be made according to known and conventional methods for preparing such formulations.

Since some of the compounds of formula (I) of this invention may not be highly soluble in water at physiological conditions, a solubilizing excipient may be used to increase solubility. Solubilization is taken to mean an improvement in the solubility by virtue of surface-active compounds that can convert substances that are insoluble or virtually insoluble in water into clear, or opalescent, aqueous solutions without changing the chemical structure of these substances in the process. Excipients used for this purpose are restricted to those that are safe for administration to humans. Typically such co-solvents are employed at a level of about 0.01% to 2% by weight.

A variety of solubilizing excipients may be used for the formulation of the rifamycin analog, including compounds belonging to the following classes: polyethoxylated fatty acids, PEG-fatty acid diesters, PEG-fatty acid mono-ester and di-ester mixtures, polyethylene glycol glycerol fatty acid esters, alcohol-oil transesterification products, polyglycerized fatty acids, propylene glycol fatty acid esters, mixtures of propylene glycol esters and glycerol esters, mono- and diglycerides, sterol and sterol derivatives, polyethylene glycol sorbitan fatty acid esters, polyethylene glycol alkyl ethers, sugar esters, polyethylene glycol alkyl phenols, polyoxyethylene-polyoxypropylene block copolymers, sorbitan fatty acid esters, lower alcohol fatty acid esters, or ionic surfactants. Such excipients are described for example, in U.S. patent application Ser. No: 60/385,532, hereby incorporated by reference.

Ototopical preparations may vary in viscosity. The use of viscosity enhancing agents to provide the compositions of the invention with viscosities greater than the viscosity of simple aqueous solutions may be desirable to increase the retention time in the ear. Such viscosity-building agents include, for example, polyvinyl alcohol, polyvinyl pyrrolidone, methyl cellulose, hydroxypropyl methylcellulose, hydroxyethyl cellulose, carboxymethyl cellulose, hydroxypropyl cellulose, or other agents known to those skilled in the art. Such agents are typically employed at a level of about 0.01% to 2% by weight. Optionally, these preparations may include a buffering agent to maintain an acidic pH, since the normal environment of the external auditory canal is acidic. However, if treatment is required in the middle ear where the pH is neutral, the pH can be adjusted accordingly.

Otic pharmaceutical products are typically packaged in multidose form. Preservatives are thus desired to prevent microbial contamination during use. Suitable preservatives include: polyquaternium-1, benzalkonium chloride, thimerosal, chlorobutanol, methyl paraben, propyl paraben, phenylethyl alcohol, edetate disodium, sorbic acid, or other agents known to those skilled in the art. Typically such preservatives are employed at a level of from 0.001% to 1.0% by weight.

A penetration enhancer may also be used to facilitate the diffusion of a rifamycin analog of the invention through the tympanic membrane into the middle and inner ear in order to reduce inflammation of ear tissues. A penetration enhancer is an agent used to increase the permeability of the skin to a pharmacologically active agent to increase the rate at which the drug diffuses through the skin and enters the tissues and bloodstream. A chemical skin penetration enhancer increases skin permeability by reversibly damaging or by altering the physiochemical nature of the stratum corneum to reduce its diffusional resistance (Osborne D W, Henke J J, *Pharmaceutical Technology*, November 1997, pp 58-86). Examples of penetration enhancers include without limitation: alcohols, such as ethanol and isopropanol; polyols, such as n-alkanols, limonene, terpenes, dioxolane, propylene glycol, ethylene glycol, other glycols, and glycerol; sulfoxides, such as dimethylsulfoxide (DMSO), dimethylformamide, methyl dodecyl sulfoxide, dimethylacetamide; esters, such as isopropyl myristate/palmitate, ethyl acetate, butyl acetate, methyl proprionate, and capric/caprylic triglycerides; ketones; amides, such as acetamides; oleates, such as triolein; various surfactants, such as sodium lauryl sulfate; various alkanoic acids, such as caprylic acid; lactam compounds, such as azone; alkanols, such as oleyl alcohol; dialkylamino acetates, and admixtures thereof. The use of such penetration enhancers is disclosed, for example, in U.S. Pat. No 6,093,417, hereby incorporated by reference.

Other Therapeutic Agents

Compositions containing a compound of the invention may also include a second therapeutic agent, including for example, another rifamycin, an anesthetic, an antimicrobial agent, a zinc salt, or an anti-inflammatory agent (e.g., an non-steroidal anti-inflammatory or a steroid). When admixing an antimicrobial agent, the antimicrobial agent is preferably penicillin G, penicillin V, methicillin, oxacillin, cloxacillin, dicloxacillin, nafcillin, ampicillin, amoxicillin, carbenicillin, ticarcillin, mezlocillin, piperacillin, azlocillin, temocillin, cepalothin, cephapirin, cephradine, cephaloridine, cefazolin, cefamandole, cefuroxime, cephalexin, cefprozil, cefaclor, loracarbef, cefoxitin, cefmatozole, cefotaxime, ceftizoxime, ceftriaxone, cefoperazone, ceftazidime, cefixime, cefpodoxime, ceftibuten, cefdinir, cefpirome, cefepime, BAL5788, BAL9141, imipenem, ertapenem, meropenem, astreonam, clavulanate, sulbactam, tazobactam, streptomycin, neomycin, kanamycin, paromycin, gentamicin, tobramycin, amikacin, netilmicin, spectinomycin, sisomicin, dibekalin, isepamicin, tetracycline, chlortetracycline, demeclocycline, minocycline, oxytetracycline, methacycline, doxycycline, erythromycin, azithromycin, clarithromycin, telithromycin, ABT-773, lincomycin, clindamycin, vancomycin, oritavancin, dalbavancin, teicoplanin, quinupristin and dalfopristin, sulphanilamide, paraaminobenzoic acid, sulfadiazine, sulfisoxazole, sulfamethoxazole, sulfathalidine, linezolid, nalidixic acid, oxolinic acid, norfloxacin, perfloxacin, enoxacin, ofloxacin, ciprofloxacin, temafloxacin, lomefloxacin, fleroxacin, grepafloxacin, sparfloxacin, trovafloxacin, clinafloxacin, gatifloxacin, moxifloxacin, gemifloxacin, sitafloxacin, metronidazole, daptomycin, garenoxacin, ramoplanin, faropenem, polymyxin, tigecycline, AZD2563, or trimethoprim. Preferred non-steroidal anti-inflammatory agents include, for example, detoprofen, diclofenac, diflunisal, etodolac, fenoprofen, flurbiprofen, indomethacin, ketoprofen, mechlofenameate, mefenamic acid, meloxicam, nabumeone, naproxen sodium, oxaprozin, piroxicam, sulindac, tolmeting, celecoxib, rofecoxib, choline salicylate, salsate, sodium salicylate, magnesium salicylate, aspirin, ibuprofen, paracetamol, acetaminophen, and pseudoephedrine, and preferred steroids include, for example, hydrocortisone, prednisone, fluprednisolone, triamcinolone, dexamethasone, betamethasone, cortisone, prednilosone, methylprednisolone, fluocinolone acetonide, flurandrenolone acetonide, and fluorometholone. Preferred anesthetics according to the invention include, for example, benzocaine, butamben picrate, tetracaine, dibucaine, prilocaine, etidocaine, mepivacaine, bupivicaine, and lidocaine. A zinc salt can be zinc sulfate, zinc chloride, zinc acetate, zinc phenol sulfonate, zinc borate, zinc bromide, zinc nitrate, zinc glycerophosphate, zinc benzoate, zinc carbonate, zinc citrate, zinc hexafluorosilicate, zinc diacetate trihydrate, zinc oxide, zinc peroxide, zinc salicylate, zinc silicate, zinc stannate, zinc tannate, zinc titanate, zinc tetrafluoroborate, zinc gluconate, or zinc glycinate. All of the therapeutic agents employed in the compositions of the present invention can be used in the dose ranges currently known and used for these agents. Different concentrations may be employed depending on the clinical condition of the patient, the goal of therapy (treatment or prophylaxis), the anticipated duration, and the severity of the infection for which a rifamycin analog of the invention is being administered. Additional considerations in dose selection include the type of infection, age of the patient (e.g., pediatric, adult, or geriatric), general health, and comorbidity.

Assays

Compounds of the present invention can be screened for antimicrobial activity by measuring their minimum inhibitory concentration (MIC), using standard MIC in vitro assays (see, for example, Tomioka et al., *Antimicrob. Agents Chemother.* 37:67 (1993). Agents can be screened against *C. pneumoniae, C. trachomatis, M. tuberculosis* (including multiple drug resistant strains), *M. avium* complex, and other intracellular infectious microbes. Details of a standard MIC assay are provided in Example 2.

Therapy

The invention features a method of treating or preventing a disease or condition associated with a microbial infection by administering a compound of formulas (I). Compounds of the present invention may be administered by any appropriate route for treatment or prevention of a disease or condition associated with a microbial infection, inflammation, or infection derived autoimmune disease. These may be administered to humans, domestic pets, livestock, or other animals with a pharmaceutically acceptable diluent, carrier, or excipient, in unit dosage form. Administration may be topical, parenteral, intravenous, intra-arterial, subcutaneous, intramuscular, intracranial, intraorbital, ophthalmic, intraventricular, intracapsular, intraspinal, intracisternal, intraperitoneal, intranasal, aerosol, by suppositories, or oral administration.

Therapeutic formulations may be in the form of liquid solutions or suspensions; for oral administration, formulations may be in the form of tablets or capsules; and for intranasal formulations, in the form of powders, nasal drops, or aerosols.

Methods well known in the art for making formulations are found, for example, in *Remington: The Science and Practice of Pharmacy* (20th ed., ed. A.R. Gennaro AR.), Lippincott Williams & Wilkins, 2000. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Nanoparticulate formulations (e.g., biodegradable nanoparticles, solid lipid nanoparticles, liposomes) may be used to control the biodistribution of the compounds. Other potentially useful parenteral delivery systems include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycholate and deoxycholate, or may be oily solutions for administration in the form of nasal drops, or as a gel. The concentration of the compound in the formulation will vary depending upon a number of factors, including the dosage of the drug to be administered, and the route of administration.

Formulations for oral use include tablets containing the active ingredient(s) in a mixture with non-toxic pharmaceutically acceptable excipients. These excipients may be, for example, inert diluents or fillers (e.g., sucrose, sorbitol, sugar, mannitol, microcrystalline cellulose, starches including potato starch, calcium carbonate, sodium chloride, lactose, calcium phosphate, calcium sulfate, or sodium phosphate); granulating and disintegrating agents (e.g., cellulose derivatives including microcrystalline cellulose, starches including potato starch, croscarmellose sodium, alginates, or alginic acid); binding agents (e.g., sucrose, glucose, sorbitol, acacia, alginic acid, sodium alginate, gelatin, starch, pregelatinized starch, microcrystalline cellulose, magnesium aluminum silicate, carboxymethylcellulose sodium, methylcellulose, hydroxypropyl methylcellulose, ethylcellulose, polyvinylpyrrolidone, or polyethylene glycol); and lubricating agents, glidants, and antiadhesives (e.g., magnesium stearate, zinc stearate, stearic acid, silicas, hydrogenated vegetable oils, or talc). Other pharmaceutically acceptable excipients can be colorants, flavoring agents, plasticizers, humectants, buffering agents, and the like.

The tablets may be uncoated or they may be coated by known techniques, optionally to delay disintegration and absorption in the gastrointestinal tract and thereby providing a sustained action over a longer period. The coating may be adapted to release the active drug substance in a predetermined pattern (e.g., in order to achieve a controlled release formulation) or it may be adapted not to release the active drug substance until after passage of the stomach; this may be achieved by means of an enteric coating (e.g., a pH-sensitive enteric polymer). Desirably, a substantial amount of the drug is released in the lower gastrointestinal tract. The coating may be a sugar coating, a film coating (e.g., based on hydroxypropyl methylcellulose, methylcellulose, methyl hydroxyethylcellulose, hydroxypropylcellulose, carboxymethylcellulose, acrylate copolymers, polyethylene glycols and/or polyvinylpyrrolidone), or a coating based on methacrylic acid copolymer, cellulose acetate phthalate, hydroxypropyl methylcellulose phthalate, hydroxypropyl methylcellulose acetate succinate, polyvinyl acetate phthalate, shellac, and/or ethylcellulose. Furthermore, a time delay material such as, for example, glyceryl monostearate or glyceryl distearate, may be employed.

The solid tablet compositions may include a coating adapted to protect the composition from unwanted chemical changes (e.g., chemical degradation prior to the release of the active drug substance). The coating may be applied on the solid dosage form in a similar manner as that described in *Encyclopedia of Pharmaceutical Technology*, 20$^{th}$ Edition, Eds. Swarbrick and Boyland, 2000.

Formulations for oral use may also be presented as chewable tablets, or as hard gelatin capsules wherein the active ingredient is mixed with an inert solid diluent (e.g., potato starch, lactose, microcrystalline cellulose, calcium carbonate, calcium phosphate or kaolin), or as soft gelatin capsules wherein the active ingredient is mixed with water or an oil medium, for example, peanut oil, liquid paraffin, or olive oil. Powders and granulates may be prepared using the ingredients mentioned above under tablets and capsules in a conventional manner using, e.g., a mixer, a fluid bed apparatus or a spray drying equipment.

Controlled release compositions for oral use may be constructed to release the active drug by controlling the dissolution and/or the diffusion of the active drug substance.

Any of a number of strategies can be pursued in order to obtain controlled release in which the rate of release outweighs the rate of metabolism of the compound in question. In one example, controlled release is obtained by appropriate selection of various formulation parameters and ingredients, including, e.g., various types of controlled release compositions and coatings. Thus, the drug is formulated with appropriate excipients into a pharmaceutical composition that, upon administration, releases the drug in a controlled manner. Examples include single or multiple unit tablet or capsule compositions, oil solutions, suspensions, emulsions, microcapsules, microspheres, nanoparticles, patches, and liposomes.

Dissolution or diffusion controlled release can be achieved by appropriate coating of a tablet, capsule, pellet, or granulate formulation of compounds, or by incorporating the compound into an appropriate matrix. A controlled release coating may include one or more of the coating substances mentioned above and/or, e.g., shellac, beeswax, glycowax, castor wax, carnauba wax, stearyl alcohol, glyceryl monostearate, glyceryl distearate, glycerol palmitostearate, ethylcellulose, acrylic resins, dl-polylactic acid, cellulose acetate butyrate, polyvinyl chloride, polyvinyl acetate, vinyl pyrrolidone, polyethylene, polymethacrylate, methylmethacrylate, 2-hydroxymethacrylate, methacrylate hydrogels, 1,3 butylene glycol, ethylene glycol methacrylate, and/or polyethylene glycols. In a controlled release matrix formulation, the matrix material may also include, e.g., hydrated methylcellulose, carnauba wax and stearyl alcohol, carbopol 934, silicone, glyceryl tristearate, methyl acrylate-methyl methacrylate, polyvinyl chloride, polyethylene, and/or halogenated fluorocarbon.

A controlled release composition containing a compound of the invention may also be in the form of a buoyant tablet or capsule (i.e., a tablet or capsule that, upon oral administration, floats on top of the gastric content for a certain period of time). A buoyant tablet formulation of the compound(s) can be prepared by granulating a mixture of the drug(s) with excipients and 20-75% w/w of hydrocolloids, such as hydroxyethylcellulose, hydroxypropylcellulose, or hydroxypropylmethylcellulose. The obtained granules can then be compressed into tablets. On contact with the gastric juice, the tablet forms a substantially water-impermeable gel barrier around its surface. This gel barrier takes part in maintaining a density of less than one, thereby allowing the tablet to remain buoyant in the gastric juice.

Formulations for Colonic Release

Due to the lack of digestive enzymes, colon is considered a suitable site for the absorption of various drugs. Furthermore, colonic drug delivery of a compound of the invention allows local, direct treatment of colonic disease, e.g., ulcerative colitis, Crohn's disease, or colon cancer. In addition, as the colon has a longer retention time, drug absorption is prolonged, and total bioavailability is increased. See Sintov et al., *Int. J. Pharma*. 143:101-106 (1996).

One approach for delivering a compound of the invention to the colon is based on the different pH of each compartment of the gastrointestinal tract, with the pH of the proximal GI tract being lower than that of the distal GI tract. Thus, polymers that are insoluble at low pH and soluble at higher pH have been used to deliver drugs to the distal GI tract. U.S. Pat. Nos. 5,401,512 and 5,541,170, and WO 95/11024 describe drug compositions for selectively releasing the drug in the colon by way of exploiting the difference in pH between the colon and other parts of the GI tract.

Another approach is based on the fact that transit time through the stomach is approximately 2 hours, whereas transit time through the small intestine is approximately 4-6 hours. Thus, in this approach, the delivery system is designed to withhold the release of a compound of the invention for about 6-8 hours from the time of administration. For example, U.S. Pat. Nos. 5,482,718; 4,627,851; 4,693,895; 4,705,515; 5,171,580; 5,536,507; and 4,904,474; and EP 621 032 A1, JP 34929/1991A, EP 453 001 A1, and EP 572 942 A2 disclose time dependent drug delivery system. They are designed to prevent drug release for a period of time expected to be sufficient for the composition to pass through the upper gastrointestinal tract.

In addition, it is well known that enzymes capable of reducing azo bonds or hydrolyzing glycosidic bonds, which are not degraded in the stomach and small intestine, are present in the colon. Thus, another approach for the colonic delivery of a compound of the invention is to use azo bond-containing polymers (azo polymers) or glycosidic bond-containing materials.

The glycosidic bond-containing polymers include disaccharides, oligosaccharides, and polysaccharides. U.S. Pat. No. 5,505,966 discloses a pharmaceutical composition containing calcium pectinate as a major component and a filler such as pectin, dextran, avicel, or mixture thereof. U.S. Pat. No. 5,525,634 discloses a pharmaceutical composition containing a synthetic or natural polymer that is degradable by a colonic enzyme, herein calcium pectinate is disclosed as an example of a natural polymer. In U.S. Pat. No. 5,505,966, the calcium pectinate composition is used in the form of a coacervate pellet. It is believed that calcium pectinate, which is insoluble in water, is converted to a water-soluble matrix by sodium ions or potassium ions present in the digestion solution of upper GI. U.S. Pat. No. 5,525,634 describes a compressed tablet formulation that is prepared by pulverizing and compressing a pharmaceutical composition containing a drug and calcium pectinate. In the composition, the strength of compression largely affects the system disintegration through the GI tract. In another example useful for the formulation of compounds of the invention for colonic release, Adkin et al., *Pharm. Res*. 14:103-107,1997, describe the addition of Guar gum or pectin as a binder of calcium pectinate compressed tablets and coating them with enteric material. In this example, Guar gum or pectin is used as a binder for preventing easy disintegration in upper GI to achieve sustained release effect in colon. In other examples useful for the colonic delivery of the compounds of the invention, U.S. Pat. No. 4,432,966 discloses a composition comprising microcrystalline cellulose and ethyl cellulose; EP 627 173 A1 describes a cellulose composition; WO 95/35100 discloses a starch capsule and a composition comprising an enteric coating; U.S. Pat. No. 5,422,121 discloses a composition comprising a guar gum or locust bean gum blended with a film forming material, and U.S. Pat. No. 6,413,494 describes compositions that contain two polysaccharides, such as, for example, galactomannan and pectin, which are degradable by colonic enzymes and are useful for colonic release formulations.

The compound may be optionally administered as a pharmaceutically acceptable salt, such as a non-toxic acid addition salts or metal complexes that are commonly used in the pharmaceutical industry. Examples of acid addition salts include organic acids such as acetic, lactic, pamoic, maleic, citric, malic, ascorbic, succinic, benzoic, palmitic, suberic, salicylic, tartaric, methanesulfonic, toluenesulfonic, or trifluoroacetic acids or the like; polymeric acids such as tannic acid, carboxymethyl cellulose, or the like; and inorganic acid such as hydrochloric acid, hydrobromic acid, sulfuric acid phosphoric acid, or the like. Metal complexes include zinc, iron, and the like.

Pharmaceutical formulations of compounds of the invention described herein include isomers such as diastereomers and enantiomers, mixtures of isomers, including racemic mixtures, salts, solvates, and polymorphs thereof.

Compounds of the invention may be used in combination with another antifungal, antiviral, antibacterial, or antiprotozoan compound or combinations thereof. The other agent may be employed as a supplemental antimicrobial for the purpose of broadening the activity spectrum of the therapeutics or to obtain particular effects, such as, to reduce the development of drug resistant microbes. Compounds of the invention can be used either alone or in conjunction with other pharmaceutical compounds to effectively combat a single infection. For example, compounds of the invention may be used either alone or combined with acyclovir in a combination therapy to treat HSV-1. Compounds of the invention may also be used either alone or in conjunction with other pharmaceutical compounds to combat multiple infections. For example, compounds of the invention may be used in combination with one or more anti-mycobacterial agents agents such as isoniazid, pyrazinamide, or ethambutol to treat or prevent intracellular bacterial infections. Compounds of the invention may also be used in combination with Intron A and/or a biflavanoid for treating Hepatitis B; with gancyclovir, progancyclovir, famcyclovir, foscarnet, vidarabine, cidovir, and/or acyclovir for treating herpes viruses; and with ribavarin, amantidine, and/or rimantidine for treating respiratory viruses.

The following examples are put forth so as to provide those of ordinary skill in the art with a complete disclosure and description of how the methods and compounds claimed herein are performed, made, and evaluated, and are intended to be purely exemplary of the invention and are not intended to limit the scope of what the inventors regard as their invention.

Syntheses of Benzoxazinorifamycin Compounds

Rifamycin analogs of formula (I) can be synthesized by methods analogous to those disclosed in U.S. Pat. Nos. 4,610,919; 4,983,602; 5,786,349; 5,981,522; and 4,859,661, and *Chem. Pharm. Bull.*, 41:148 (1993), each of which is hereby incorporated by reference. Syntheses of rifamycin analogs of formula (I) are provided in the Examples. The synthesis of the 25-hydroxy prodrug analog (see Seligson, et al., *Anti-Cancer Drugs* 12:305-13, 2001), 25-O-deacetyl-25-(2",3"-dihydroxypropylcarbonoxy)-4'-fluoro-5'-[4-isobutyl-1-piperazinyl]benzoxazinorifamycin (Example 5 and FIG. 1) can be used as a guide for the synthesis of other rifamycin analogs in which the 25-hydroxyl group is derivatized (e.g., as an ester, a carbamate, or a carbonate).

Benzoxazinorifamycin compounds can be prepared using methods that require the selective protection and deprotection of alcohols, amines, sulfhydryls and/or carboxylic acid functional groups. For example, commonly used protecting groups for amines include carbamates, such as tert-butyl, benzyl, 2,2,2-trichloroethyl, 2-trimethylsilylethyl, 9-fluorenylmethyl, allyl, and m-nitrophenyl. Other commonly used protecting groups for amines include amides, such as formamides, acetamides, trifluoroacetamides, sulfonamides, trifluoromethanesulfonyl amides, trimethylsilylethane-sulfonamides, and tert-butylsulfonyl amides. Examples of commonly used protecting groups for carboxylic acids include esters, such as methyl, ethyl, tert-butyl, 9-fluorenylmethyl, 2-(trimethylsilyl)ethoxy methyl, benzyl, diphenylmethyl, O-nitrobenzyl, ortho-esters, and halo-esters. Examples of commonly used protecting groups for alcohols include ethers, such as methyl, methoxymethyl, methoxyethoxymethyl, methylthiomethyl, benzyloxymethyl, tetrahydropyranyl, ethoxyethyl, benzyl, 2-napthylmethyl, O-nitrobenzyl, P-nitrobenzyl, P-methoxybenzyl, 9-phenylxanthyl, trityl (including methoxy-trityls), and silyl ethers. Examples of commonly used protecting groups for sulfhydryls include many of the same protecting groups used for hydroxyls. In addition, sulfhydryls can be protected in a reduced form (e.g., as disulfides) or an oxidized form (e.g., as sulfonic acids, sulfonic esters, or sulfonic amides). Protecting groups can be chosen such that selective conditions (e.g., acidic conditions, basic conditions, catalysis by a nucleophile, catalysis by a Lewis acid, or hydrogenation) are required to remove each, exclusive of other protecting groups in a molecule. The conditions required for the addition of protecting groups to amine, alcohol, sulfhydryl, and carboxylic acid functionalities and the conditions required for their removal are provided in detail in T. W. Green and P. G. M. Wuts, *Protective Groups in Organic Synthesis* (2$^{nd}$ Ed.), John Wiley & Sons, 1991 and P. J. Kocienski, *Protecting Groups*, Georg Thieme Verlag, 1994 (hereby incorporated by reference). In the examples that follow, the use of protecting groups is indicated in a structure by the letter P, where P for any amine, carboxylic acid, sulfhydryl, or alcohol may be any of the protecting groups listed above.

EXAMPLE 1

General Coupling Procedure

The synthesis of 5'-substituted benzoxazinorifamycin, 5'-substituted benzthiazinorifamycin, and 5'-substituted benzdiazinorifamycin analogs can all proceed through the same general route as shown in Scheme 1, using the general methods disclosed in U.S. Pat. No. 4,965,261 for the attachment of amines to the 5'-position. In this scheme, rifamycin azaquinones of the formula II are dissolved in a suitable solvent, for example, DMSO, and reacted with amines or the formula III in the presence of manganese dioxide for several hours at room temperature to form azaquinones of the formula IV. If required, azaquinones of the formula IV can be further reacted with deprotection reagents to remove X at the 25-position, P' at the 21 and 23 positions, and/or any P''' protecting group introduced with amines of the formula III. In some embodiments, the 25-position can be further derivatized with groups that introduce useful pharmacodynamic properties, such as groups that transform a rifamycin analog into a prodrug. Such groups are known to those skilled in the art, examples of which can be found in Testa and Mayer, *Hydrolysis in Drug and Prodrug Metabolism: Chemistry, Biochemistry and Enzymology*, published by Vch. Verlagsgesellschaft Mbh. (2003), which is hereby incorporated by reference.

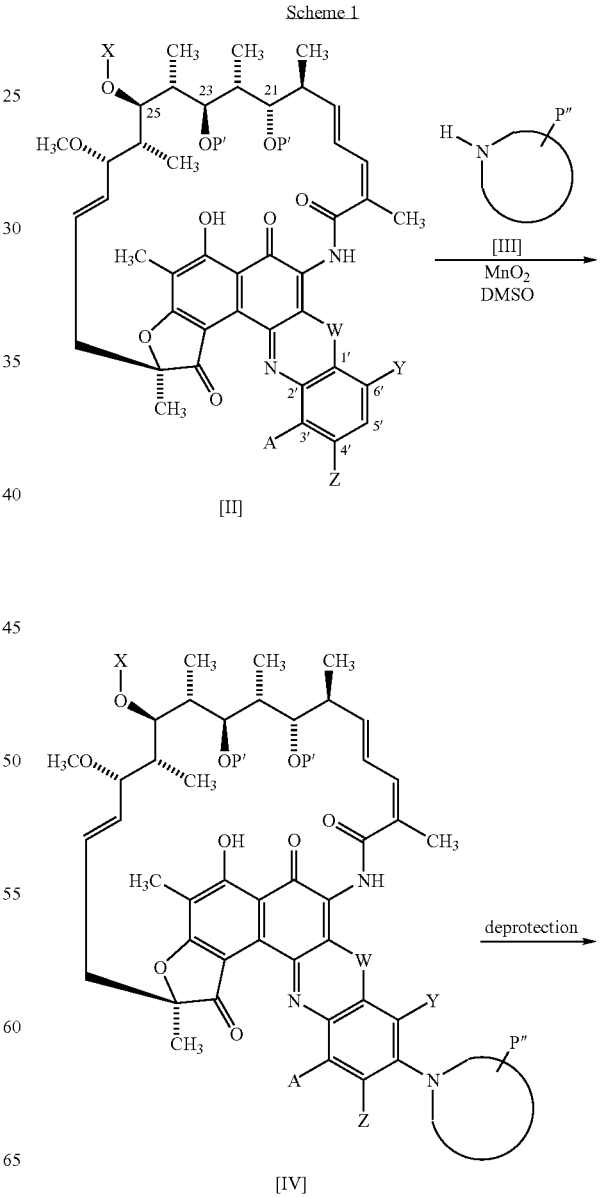

A general example is given as follows:

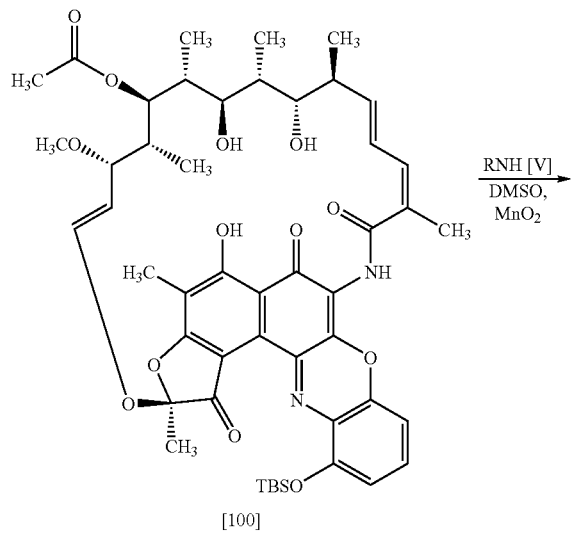

[100]

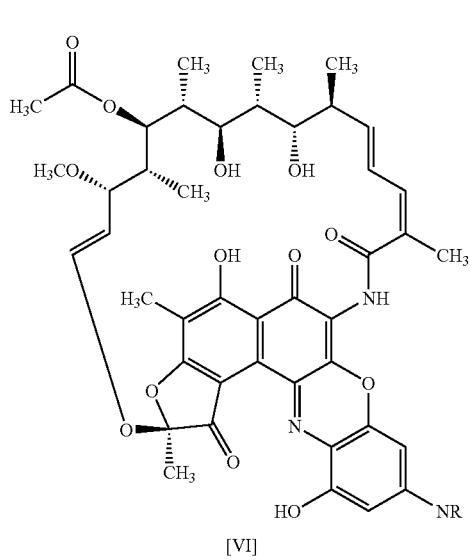

[VI]

Compound 100 (1.00 g, 1.09 mmol) was dissolved in methyl sulfoxide (10 mL) and treated with an amine of the formula V (2.18 mmol) and manganese(IV) oxide (0.95 g, 10.9 mmol) for between 12 h to 120 h at rt to 65° C. The reaction mixture was subsequently diluted with ethyl acetate, filtered through celite, washed with water (×3), and dried over $Na_2SO_4$. Filtration, followed by removal of the solvent in vacuo, yielded a residue that was purified via flash chromatography (silica gel) using an appropriate solvent system, such as 1-10% methanol in methylene chloride, to produce a benzoxazinorifamycin of the formula VI. If further purification is desired, a second column employing $C_{18}$ silica gel, using an appropriate solvent system such as 10% water in methanol, was performed.

Alternatively, using the methods described in *Helv. Chim. Acta* 56:2369 (1973), rifamycin quinones of the formula (VII) can be reacted with anilines of the formula VIII, as shown in Scheme 2, to produce azaquinones of the formula IX.

Scheme 2

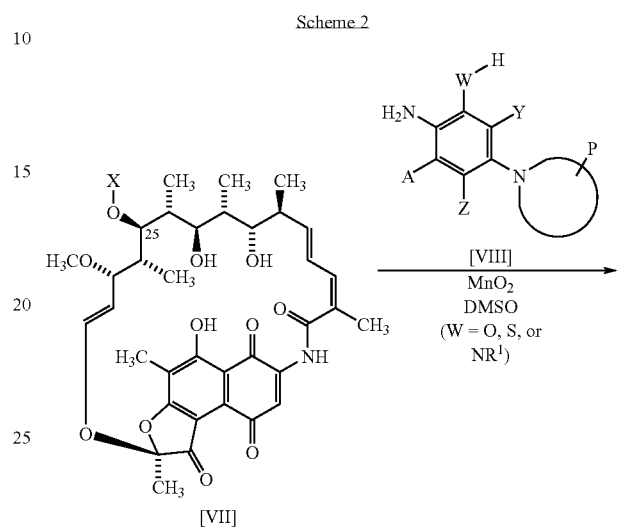

[VII]

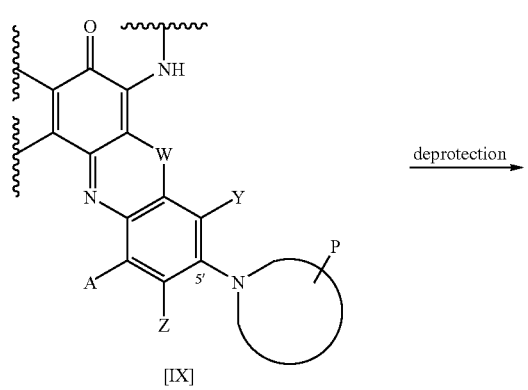

[IX]

EXAMPLE 2

General Deacetylation Procedure

Compounds of the formula VI (~100 mmol) were dissolved in methanol (5 mL) and then treated with saturated sodium hydroxide in methanol solution (5 mL) for between 0.5 h to 3 h at rt. The reaction mixture was then poured into saturated ammonium chloride solution and extracted with chloroform. The organics were washed with water (2×) and dried over $Na_2SO_4$. Filtration, followed by removal of the solvent in vacuo, yielded the desired des-acetyl product of the formula X. If desired, these products were purified via flash chromatography (silica gel) using an appropriate solvent system, such as 1-10% methanol in methylene chloride.

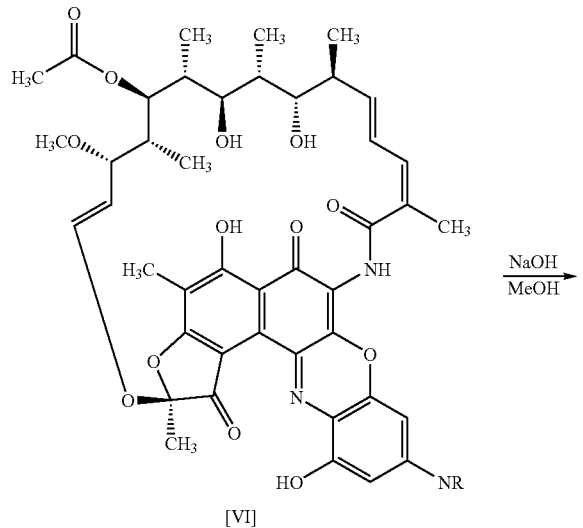

[VI]

[X]

EXAMPLE 3

Synthesis of Compound No. 1 (see Table 1 for Structure)

The title compound was prepared using the general coupling procedure of Example 1 with compound 100 (1.34 g, 1.46 mmol), commercially available piperidin-4-yl-carbamic acid, ethyl ester (628 mg, 3.65 mmol), and manganese(IV) oxide (1.27 g, 14.6 mmol), to provide compound 1 (1.01 g, 71% yield) as a blue solid, Mp=218-222° C.; ESI (+) MS: 971 (M+H$^+$); UV/Vis: $\lambda_{max}$=643.0 nm.

EXAMPLE 4

Synthesis of Compound No. 3 (see Table 1 for Structure)

The title compound was prepared by general deacetylation procedure of Example 2, using compound 1 (155 mg, 0.160 mmol) to provide compound 3 (133 mg, 89% yield) as a blue solid, Mp=206-216° C.; ESI (+) MS: 929 (M+H$^+$); UV/Vis: $\lambda_{max}$=643.0 nm.

EXAMPLE 5

Synthesis of Compound No. 80

[80]

The title compound was prepared using the general coupling procedure of Example 1 with compound 100 (933 mg, 1.02 mmol), commercially available (1S, 4S)-(+)-2,5-diazabicyclo[2.2.1]heptane dihydrobromide (531 mg, 2.04 mmol), diisopropylethylamine (1.07 mL, 6.12 mmol), and manganese(IV) oxide (887 mg, 10.2 mmol) to provide compound 80 (206 mg, 23% yield) as a blue solid, Mp=>330° C.; ESI (+) MS: 897 (M+H$^+$); UV/Vis: $\lambda_{max}$=649.4 nm.

EXAMPLE 6

Synthesis of Compound No. 2 (see Table 1 for Structure)

The precursor amine used in the preparation of compound 2 was prepared as follows:

47

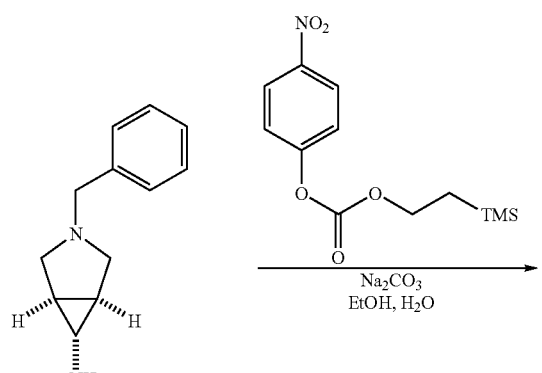

[101b]

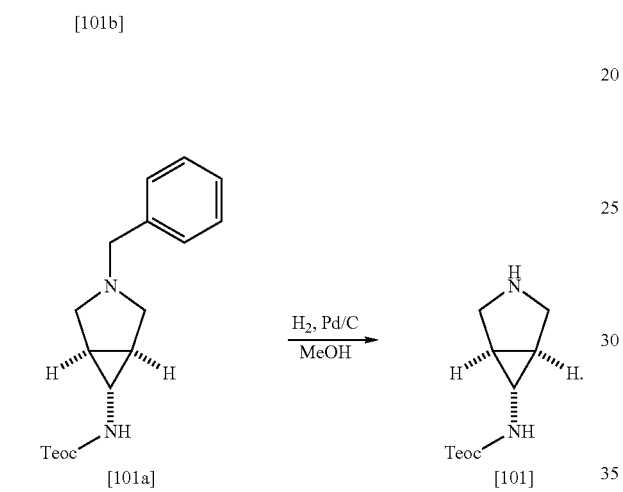

2-(Trimethylsilyl)ethyl p-nitrophenyl carbonate (2.26 g, 7.97 mmol) in abs. ethanol (10 mL) was added to a stirred suspension of compound 101b (1.50 g, 7.97 mmol, *J. Chem. Soc., Perkin Trans.* 1 2000: 1615-22) in aq. Na$_2$CO$_3$ (20 mL, 2M). Water (10 mL) was added and the sides of the flask were rinsed with abs. ethanol (15 mL). The reaction was refluxed with stirring for 1 hour, cooled, and then stirred under an atmosphere of N$_2$ at ambient temperature for 16.5 hours. Most of the solvent was removed in vacuo and the resulting slurry was partitioned between methylene chloride and water. The aqueous layer was extracted with methylene chloride (×3). The organic layers were combined and dried over Na$_2$SO$_4$. Filtration followed by removal of the solvent in vacuo yielded a residue that was purified via flash chromatography (19:1, methylene chloride:methanol) to yield compound 101b (2.12 g, 80% yield) as a light brown oil, $^1$H NMR (CDCl$_3$, 300 MHz): 0.03 (s, 9H), 0.97 (t,j=8.3 Hz, 2H), 1.50 (s, 2H), 2.38 (d,j=8.9 Hz, 2H), 2.92 (s, 1H), 3.06 (d,j=5.9 Hz, 2H), 3.55 (s, 2H), 4.14 (t,j=8.2 Hz, 2H), 4.64 (bs, 1H), 7.19-7.30 (m, 5H); ESI(+) MS:333(M+H$^+$).

A mixture of compound 101b (1.10 g, 3.31 mmol), Pd/C (550 mg, 10%, wet), and methanol (30 mL) was hydrogenated on a Parr apparatus at 50 psi H$_2$ for 20.5 hours. The reaction was filtered through celite, and the solvent removed in vacuo to yield compound 101 (799 mg, 100% yield) as a viscous yellow oil, $^1$H NMR (CDCl$_3$, 300 MHz): 0.04(s, 9H), 0.98 (t,j=8.4 Hz, 2H), 1.63 (s, 2H), 2.39 (d,j=1.8 Hz, 1H), 2.70 (bs, 1H), 2.98 (d,j=11.4 Hz, 2H), 3.19 (d,j=11.5 Hz, 2H), 4.15 (t,j=80 Hz, 2H), 5.30 (bs, 1H); ESI (+) MS: 243 (M+H$^+$).

48

The title compound was prepared using the general coupling procedure of Example 1 with compound 100 (1.38 g, 1.51 mmol), amine 101 (730 mg, 3.01 mmol), and manganese(IV) oxide (1.31 g, 15.1 mmol), to provide compound 2 (830 mg, 53% yield) as a blue solid, Mp=230-231° C.; ESI (+) MS: 1042 (M+H$^+$); UV/Vis: $\lambda_{max}$=640.0 nm.

EXAMPLE 7

Synthesis of Compound No. 81

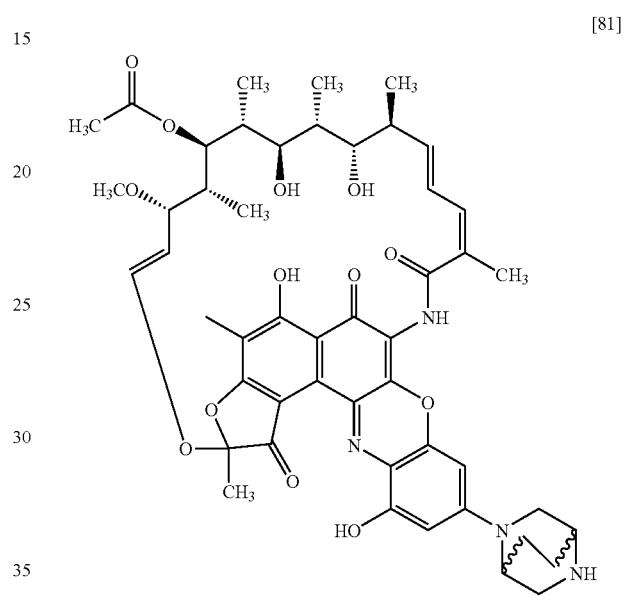

The title compound was prepared using the general coupling procedure of Example 1 using compound 100 (1.27 g, 1.39 mmol), 2,5-diaza-bicyclo[2.2.2]octane dihydrochloride (515 mg, 2.78 mmol, *J. Heterocyclic Chem.* 1974, 449-451 and *J. Med. Chem.* 1974, 481-487), diisopropylethylamine (1.45 mL, 8.34 mmol), and manganese(IV) oxide (1.21 g, 13.9 mmol) to provide compound 81 (54 mg, 4% yield) as a blue solid, Mp=>300° C.; ESI (+) MS: 911 (M+H$^+$); UV/Vis: $\lambda_{max}$=653.2 nm.

EXAMPLE 8

Synthesis of Compound No. 4 (see Table 1 for Structure)

A mixture of compound 2 (796 mg, 0.764 mmol), tetrabutylammonium fluoride (7.64 mL, 1.0 M in THF, 7.64 mmol), and acetonitrile (40 mL) was stirred under an atmosphere of N$_2$ at 50° C. for 18 hours. The reaction was cooled and poured over water. The aqueous layer was extracted with chloroform (×6). The combined organics were washed with water (×1), then dried over Na$_2$SO$_4$. Filtration, followed by removal of the solvent in vacuo, yielded a residue that was purified via MPLC (gradient, 1.25-20% methanol:methylene chloride), followed by reverse phase chromatography (C$_{18}$ silica, 9:1, methanol: water) to yield compound 4 as a blue solid (521 mg, 76% yield), Mp=216-217° C.; ESI (+) MS: 897 (M+H$^+$); UV/Vis: $\lambda_{max}$=642.3 nm.

EXAMPLE 9

Synthesis of Compound No. 20 (see Table 1 for Structure)

The title compound was prepared by the general deacetylation procedure of Example 2 using compound 4 (366 mg, 0.408 mmol) to provide compound 20 (232 mg, 66% yield) as a blue solid, Mp=211-231° C.; ESI (+) MS: 855 (M+H$^+$); UV/Vis: $\lambda_{max}$=642.8 nm.

EXAMPLE 10

Synthesis of Compound No. 5 (see Table 1 for Structure)

The precursor amine used in the preparation of compound 5 was prepared as follows:

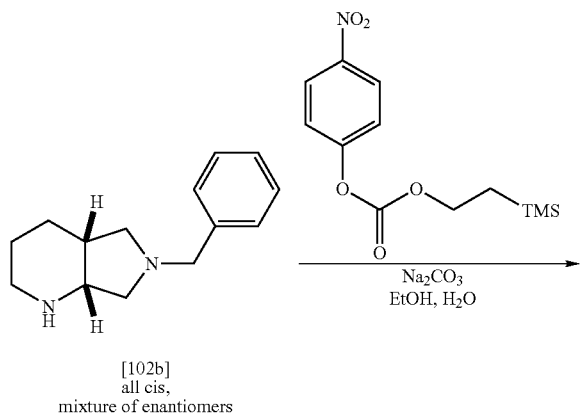

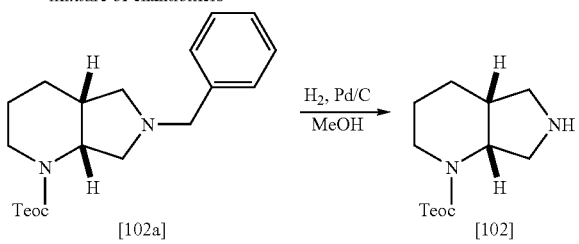

2-(Trimethylsilyl)ethyl p-nitrophenyl carbonate (2.53 g, 8.92 mmol) in abs. ethanol (25 mL) was added to a stirred suspension of compound 102b (U.S. Pat. No. 5,654,318, 1.93 g, 8.92 mmol) in aq. Na$_2$CO$_3$ (20 mL, 2M), followed by the addition of water (10 mL). The reaction was refluxed with stirring for 1 hour, cooled, and then stirred under an atmosphere of N$_2$ at ambient temperature for 19 hours. Most of the solvent was removed in vacuo and the resulting slurry was partitioned between methylene chloride and water. The aqueous layer was extracted with methylene chloride (×2). The organic layers were combined and dried over Na$_2$SO$_4$. Filtration followed by removal of the solvent in vacuo yielded a residue that was purified via flash chromatography (19:1, methylene chloride:methanol) to yield compound 102a (2.59 g, 80% yield) as a light brown oil, $^1$H NMR (CDCl$_3$, 300 MHz): 0.03 (s, 9H), 0.95-1.01 (m, 2H), 1.38-1.76 (m, 5H), 2.13-2.15 (m, 1H), 2.50 (d,j=8.9 Hz, 1H), 2.61-2.67 (m, 1H), 2.73-2.87 (m, 3H), 3.66 (dd,j=21.5, 13.1 Hz, 2H), 3.93 (bs, 1H), 4.12-4.17 (m, 2H), 4.62 (bs, 1H), 7.22-7.31 (m, 5H); ESI (+) MS: 361 (M+H$^+$).

A mixture of compound 102a (2.57 g, 7.12 mmol), Pd/C (1.3 g, 10%, wet), and methanol (50 mL, sparged with H$_2$) was stirred under balloon pressure H$_2$ for 18 hours. The reaction was filtered through celite, and the solvent removed in vacuo. The resulting residue was purified via MPLC (4:1, methylene chloride:methanol) to yield compound 102 (951 mg, 49% yield) as a yellow oil, $^1$H NMR (CDCl$_3$, 300 MHz): 0.04 (s, 9H), 0.98-1.03 (m, 2H), 1.36-1.49 (m, 2H), 1.67-1.72 (m, 2H), 1.71 (bs, 1H), 2.00-2.10 (m, 1H), 2.73-2.83 (m, 3H), 3.06-3.18 (m, 2H), 4.00 (d,j=12.3 Hz, 1H), 4.15-4.21 (m, 2H), 4.49-4.54 (m, 1H); ESI (+) MS: 271 (M+H$^+$).

Teoc-protected precursors to compounds 5 and 12 were prepared by general coupling procedure 1 using compound 100 (1.56 g, 1.71 mmol), amine 102 (922 mg, 3.41 mmol), and manganese(IV) oxide (1.49 g, 17.1 mmol) to provide 511 mg (28%) of a blue solid (1:1.1, diastereomer A: diastereomer B) and 601 mg (33%) of a blue solid (diastereomer B). Diastereomer A eluted first using a silica column on MPLC (50-100% ethyl acetate:hexanes).

A mixture of the Teoc-protected diastereomer A and B precursors to compound 5 (1:1.1, diastereomer A: diastereomer B, 363 mg, 0.339 mmol), tetrabutylammonium fluoride (3.40 mL, 1.0 M in THF, 3.39 mmol), and acetonitrile (10 mL) was stirred in a sealed flask at 50° C. for 23 hours. The reaction was cooled, and poured over water. The aqueous layer was extracted with chloroform (×2). The combined organics were washed with water (×3), then dried over Na$_2$SO$_4$. Filtration followed by removal of the solvent in vacuo yielded a residue that was purified via MPLC (gradient, 1.25-5% methanol:methylene chloride) followed by preparatory thin layer chromatography (1.0 mm silica, 9:1, methylene chloride:methanol, ~50 mg per plate) to yield compound 5 as a blue solid (155 mg), Mp=>300° C.; ESI (+) MS: 925 (M+H$^+$); UV/Vis: $\lambda_{max}$=650.3 nm.

EXAMPLE 11

Synthesis of Compound No. 12 (see Table 1 for Structure)

A mixture of the Teoc-protected diastereomer B precursor to compound 12 from Example 10 (337 mg, 0.315 mmol), tetrabutylammonium fluoride (3.15 mL, 1.0 M in THF, 3.15 mmol), and acetonitrile (10 mL) was stirred in a sealed flask at 50° C. for 23 hours. The reaction was cooled, and poured over water. The aqueous layer was extracted with chloroform (×2). The combined organics were washed with water (×3), then dried over Na$_2$SO$_4$. Filtration followed by removal of the solvent in vacuo yielded a residue that was purified via MPLC (gradient, 1.25-10% methanol:methylene chloride) followed by preparatory thin layer chromatography (1.0 mm silica, 9:1, methylene chloride:methanol, ~50 mg per plate) to yield compound 12 as a blue solid (162 mg), Mp=>320° C.; ESI (+) MS: 925 (M+H$^+$); UV/Vis: $\lambda_{max}$=650.5 nm.

EXAMPLE 12

Synthesis of Compound No. 7 (see Table 1 for Structure)

The title compound was prepared by the general deacetylation procedure of Example 2 using compound 5 (66 mg, 0.0713 mmol) to provide compound 7 (62 mg, 98% yield) as a blue solid, Mp=240-243° C.; ESI (+) MS: 883 (M+H$^+$); UV/Vis: $\lambda_{max}$=650.2 nm.

EXAMPLE 13

Synthesis of Compound No. 15 (see Table 1 for Structure)

The title compound was prepared by the general deacetylation procedure of Example 2 using compound 12 (103 mg, 0.111 mmol) to provide 98 mg of compound 15 (100% yield) as a blue solid, Mp=216-227° C.; ESI (+) MS: 883 (M+H$^+$); UV/Vis: $\lambda_{max}$=650.3 nm.

EXAMPLE 14

Synthesis of Compound No. 6 (see Table 1 for Structure)

The title compound was prepared by the general coupling procedure of Example 1 using compound 100 (2.00 g, 2.18 mmol), commercially available N-phenyl-N-(4-piperidinyl) propanamide (1.01 g, 4.36 mmol), and manganese(IV) oxide (1.93 g, 22.1 mmol) to provide compound 6 (1.35 g, 60% yield) as a blue solid, Mp=224-228° C.; ESI (+) MS: 1031 (M+H$^+$); UV/Vis: $\lambda_{max}$=642.5 nm.

EXAMPLE 15

Synthesis of Compound No. 8 (see Table 1 for Structure)

The title compound was prepared by the general deacetylation procedure of Example 2 using compound 6 (0.320 g, 0.310 mmol) to provide compound 8 (0.301 g, 98% yield) as a blue solid, Mp=214-216° C.; ESI (+) MS: 957 (M+H$^+$); UV/Vis: $\lambda_{max}$=642.8 nm.

EXAMPLE 16

Synthesis of Compound No. 9 (see Table 1 for Structure)

The title compound was prepared by the general coupling procedure of Example 1 using compound 100 (2.50 g, 2.73 mmol), commercially available 4-(piperidin-4-yl)-morpholine (1.00 g, 5.87 mmol), and manganese(IV) oxide (2.40 g, 27.6 mmol) to provide compound 9 (1.26 g, 47% yield) as a blue solid, Mp=228-230° C.; ESI (+) MS: 969 (M+H$^+$); UV/Vis: $\lambda_{max}$=646.0 nm.

EXAMPLE 17

Synthesis of Compound No. 11 (see Table 1 for Structure)

The title compound was prepared by the general deacetylation procedure of Example 2 using compound 9 (0.410 g, 0.420 mmol) to provide compound 11 (0.380 g, 96% yield) as a blue solid, Mp=222-224° C.;, ESI (+) MS: 927 (M+H$^+$); UV/Vis: $\lambda_{max}$=646.2 nm.

EXAMPLE 18

Synthesis of Compound No. 10 (see Table 1 for Structure)

The precursor amine used in the preparation of compound 10 was prepared as follows:

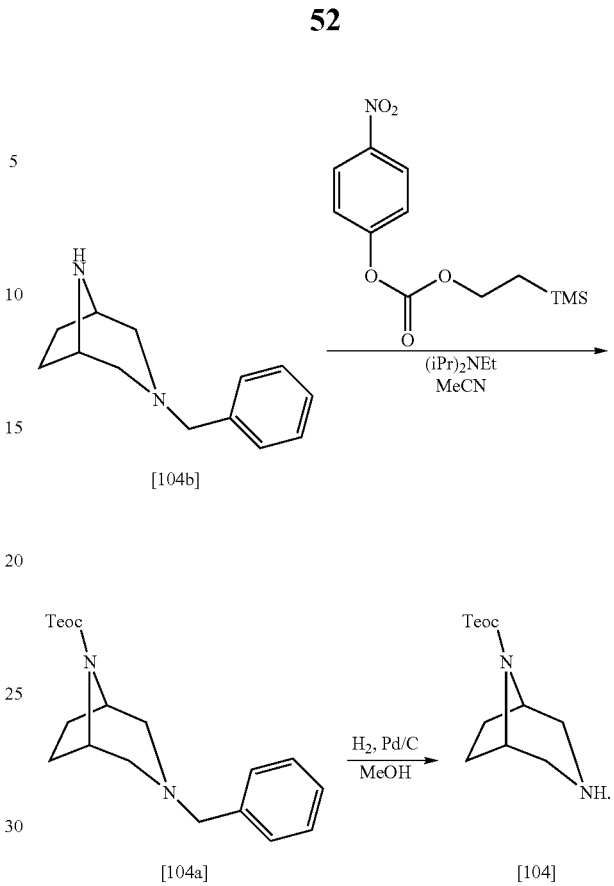

2-(Trimethylsilyl)ethyl p-nitrophenyl carbonate (1.35 g, 4.78 mmol) in acetonitrile (10 mL) was added to a stirred solution of compound 104b (Tet. Lett. 2002, 899-902, 920 mg, 4.55 mmol), and diisopropylethylamine (0.833 mL, 4.78 mmol) in acetonitrile (10 mL). The reaction was stirred at ambient temperature for 17.5 hours. The solvent was removed in vacuo and the resulting residue was dissolved in ethyl acetate and washed with 1M NaOH (×4), water (×2), then brine (×1), and dried over Na$_2$SO$_4$. Filtration, followed by removal of the solvent in vacuo, gave a residue that was purified via flash chromatography (1:4, ethyl acetate:hexanes, then 1:9 ethyl acetate:hexanes) to produce compound 104a (664 mg, 42% yield) as a colorless oil, $^1$H NMR (CDCl$_3$, 300 MHz): 0.03 (s, 9H), 0.96-1.02 (m, 2H), 1.80-1.95 (m, 4H), 2.29 (bs, 2H), 2.59-2.64 (m, 2H), 3.46 (s, 2H), 4.15-4.29 (m, 4H), 7.21-7.30 (m, 5H); ESI (+) MS: 347 (M+H$^+$).

A mixture of compound 104a (645 mg, 1.86 mmol), Pd/C (250 mg, 10%, wet), and methanol (25 mL) was hydrogenated on a Parr apparatus at 50 psi H$_2$ for 5 hours. The reaction was filtered through celite, and the solvent removed in vacuo to yield compound 104 (458 mg, 96% yield) as a white solid, $^1$H NMR (CDCl$_3$, 300 MHz): 0.03 (s, 9H), 0.94-0.99 (m, 2H), 1.76-1.91 (m, 5H), 2.60-2.64 (m, 2H), 2.94 (bs,2H), 4.11-4.18 (m, 4H); ESI (+) MS: 257 (M+H$^+$), which was used with out further purification.

The Teoc precursor to compound 10 was prepared by the general coupling procedure of Example 1 using compound 100 (805 mg, 0.880 mmol), amine 104 (452 mg, 1.76 mmol), and manganese(IV) oxide (765 mg, 8.80 mmol), which provided a blue solid (875 mg, 94% yield), ESI (+) MS: 1055 (M+H$^+$). A mixture of this Teoc precursor (506 mg, 0.480 mmol), tetrabutylammonium fluoride (4.80 mL, 1.0 M in THF, 4.80 mmol), and acetonitrile (15 mL) was stirred in a sealed flask at 50° C. for 22 hours. The reaction was cooled, and the solvent removed in vacuo. The residue was dissolved in chloroform and washed with water (×3) and dried over $Na_2SO_4$. Filtration followed by removal of the solvent in vacuo yielded a residue that was purified via MPLC (gradient, 2.5-10% methanol:methylene chloride), followed by reverse phase chromatography ($C_{18}$ silica, 9: 1, methanol:water), followed by preparatory thin layer chromatography (1.0 mm silica, 9: 1, methylene chloride:methanol, ~50 mg per plate) to yield compound 10 as a blue solid (198 mg, 45% yield), Mp=210-212° C.; ESI (+) MS: 911 (M+H$^+$); UV/Vis: $\lambda_{max}$=640.9 nm.

EXAMPLE 19

Synthesis of Compound No. 16 (see Table 1 for Structure)

The title compound was prepared by the general deacetylation procedure of Example 2 using compound 10 (87 mg, 0.0955 mmol) to provide compound 16 (83 mg, 100% yield) of a blue solid, Mp=208-229° C.; ESI (+) MS: 869 (M+H$^+$); UV/Vis: $\lambda_{max}$=641.2 nm.

EXAMPLE 20

Synthesis of Compound No. 13 (see Table 1 for Structure)

The title compound was prepared by the general coupling procedure of Example 1 using compound 100 (6.68 g, 7.30 mmol), piperidin-4-yl-carbamic acid isobutyl ester (EP 467325, 2.92 g, 14.6 mmol), and manganese(IV) oxide (6.35 g, 73.0 mmol) to provide compound 13 (4.59 g, 63% yield) as a blue solid, Mp=184-188° C.; ESI (+) MS: 999 (M+H$^+$); UV/Vis: $\lambda_{max}$=643.1 nm.

EXAMPLE 21

Synthesis of Compound No. 14 (see Table 1 for Structure)

The title compound was prepared by the general deacetylation procedure of Example 2 using compound 13 (304 mg, 0.304 mmol) to provide compound 14 (251 mg, 86%) as a blue solid, Mp=173-180° C.; ESI (+) MS: 957 (M+H$^+$); UV/Vis: $\lambda_{max}$=643.0 nm.

EXAMPLE 22

Synthesis of Compound No. 17 (see Table 1 for Structure)

The precursor amine used in the preparation of compound 17 was prepared as follows:

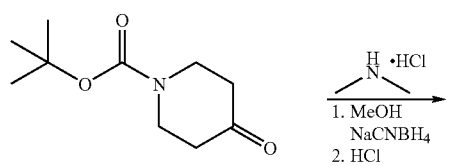

-continued

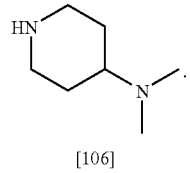

[106]

1-(tert-Butoxycarbonyl)-4-piperidone (998 mg, 4.75 mmol) in methanol (15 mL) was treated with dimethylamine hydrochloride (800 mg, 9.8 mmol) and sodium cyanoborohydride (270 mg, 4.3 mmol) at rt. After 4 days, concentrated HCl (~10 mL) was added and volume of the reaction was reduced in vacuo. The resulting residue was dissolved in $H_2O$ (30 mL) and treated with a 2M NaOH solution to achieve a pH of ~10. The aqueous solution was extracted with methylene chloride (3×20 mL) and the combined organics were dried over $Na_2SO_4$ and removed in vacuo. The resulting amine 106 (169 mg), $^1$H NMR (CDCl$_3$, 300 MHz):δ3.14 (m, 2H), 2.58 (td, J=12.3, 2.4 Hz, 2H), 2.28 (s, 6H), 2.22 (m, 1H), 1.82 (m, 2H), 1.68 (s, 1H), 1.37 (tdd, J=12.2, 12.2, 4.1 Hz, 2H); ESI (+) MS: 129 (M+H$^+$), was used without further purification.

The title compound was prepared by the general coupling procedure of Example 1 using compound 100 (724 mg, 0.791 mmol), amine 106 (169 mg, 1.32 mmol), and manganese(IV) oxide (857 mg, 9.9 mmol) to provide compound 17 (158 mg, 22%) as a blue solid, ESI (+) MS: 927 (M+H$^+$); UV/Vis: $\lambda_{max}$=646.3 nm.

EXAMPLE 23

Synthesis of Compound No. 18 (see Table 1 for Structure)

The title compound was prepared by the general deacetylation procedure of Example 2 using compound 17 (89 mg, 0.096 mmol) to provide compound 18 (70 mg, 82%) as a blue solid, Mp=214-216° C.; ESI (+) MS: 885 (M+H$^+$); UV/Vis: $\lambda_{max}$=646.5 nm.

EXAMPLE 23

Synthesis of Compound No. 19

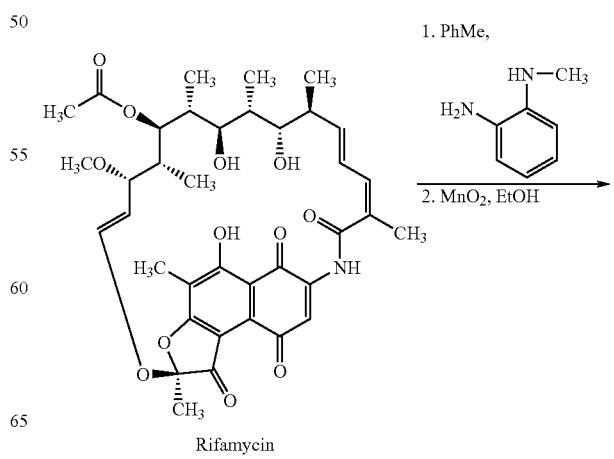

Rifamycin

-continued

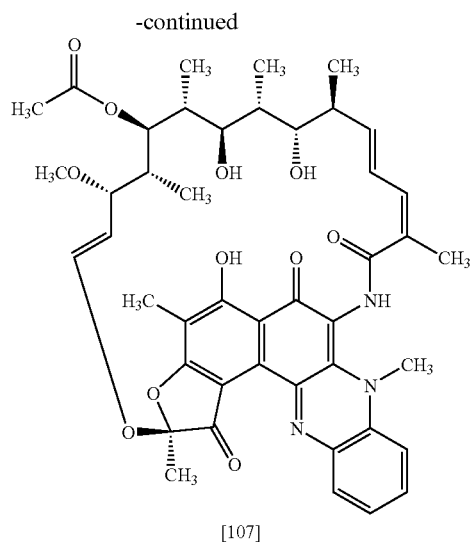

[107]

To a stirred solution of rifamycin (12.0 g, 17.3 mmol) in toluene was added N-methyl-1,2-phenylenediamine (2.10 g, 17.3 mmol) at room temperature. The resulting solution was heated at 65° C. for 48 h. The solvent was removed under vacuum. The residue was dissolved in ethanol (100 ml), and manganese(IV) oxide (14.8 g, 173 mmol) was added to the solution at room temperature. The mixture was stirred for another 48 h, followed by filtration through celite, which was washed with methylene chloride (200 mL). The combined filtrates were washed with $H_2O$ (2×200 ml) and the volume reduced in vacuo. Combiflash column (1:19:180 MeOH, ethyl acetate, methylene chloride) afforded 107 (3.8 g, 27%) as a purple solid, ESI (+) MS: 798 (M+H$^+$).

EXAMPLE 24

Synthesis of Compound No. 19 (see Table 1 for Structure)

The title compound was prepared by the general coupling procedure of Example 1 (heated to 50° C. for 5 days) using compound 107 (2.0 g, 2.5 mmol), commercially available piperidin-4-yl-carbamic acid ethyl ester (2.15 g, 12.5 mmol), and manganese(IV) oxide (21.8 g, 25 mmol) to provide compound 19 (570 mg, 23% yield) as a blue solid, Mp=220-240° C.; ESI (+) MS: 968 (M+H$^+$); UV/Vis: $\lambda_{max}$=592.7 nm.

EXAMPLE 25

Synthesis of Compound No. 31 (see Table 1 for Structure)

The title compound was prepared by the general deacetylation procedure of Example 2 using compound 19 (510 mg, 0.526 mmol) to provide compound 31 (120 mg, 24%) as a blue solid, Mp=250-252° C.; ESI (+) MS: 926 (M+H$^+$); UV/Vis: $\lambda_{max}$=591.5 nm.

EXAMPLE 26

Synthesis of Compound No. 21 (see Table 1 for Structure)

The precursor amine used in the preparation of compound 21 was prepared as follows:

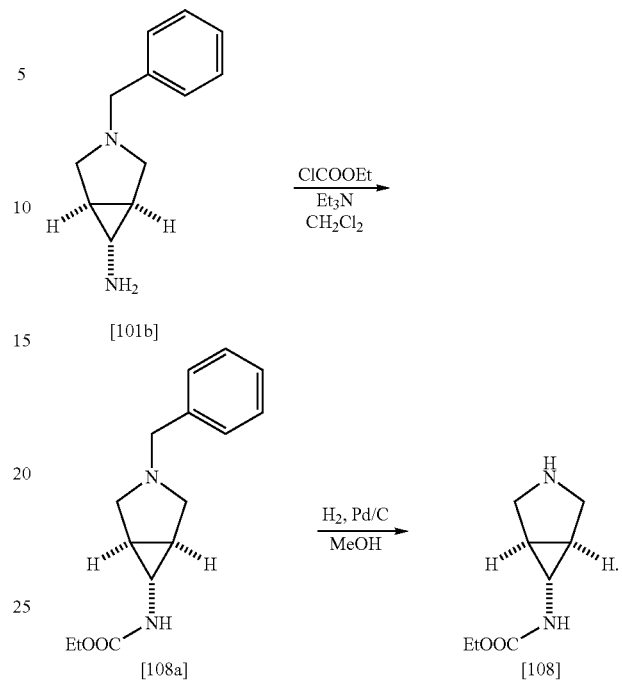

Ethyl chloroformate (0.171 mL, 1.79 mmol) was added to a stirred solution of compound 101b (306 mg, 1.63 mmol), triethylamine (0.341 mL, 2.45 mmol), and methylene chloride (15 mL) at 0° C. The reaction was stirred under an atmosphere of $N_2$ at 0° C. for 30 minutes. The reaction was quenched with sat. $NaHCO_3$ and the aqueous layer was extracted with methylene chloride (×1). The organics were combined and dried over $Na_2SO_4$. Filtration followed by removal of the solvent in vacuo yielded a residue that was purified via flash chromatography (19:1, methylene chloride:methanol) to yield compound 108a (381 mg, 90% yield) as a white solid,. $^1$H NMR (CDCl$_3$, 300 MHz): 1.23 (t,j=7.0 Hz, 3H), 1.50 (s, 2H), 2.38 (d,j=8.4 Hz, 2H), 2.93 (s, 1H), 3.06 (d,j=8.8 Hz, 2H), 3.55 (s, 2H), 4.10 (q,j=7.0 Hz, 2H), 4.67 (bs, 1H), 7.19-7.31 (m, 5H); ESI (+) MS: 261 (M+H$^+$).

A mixture of compound 108a (375 mg, 1.44 mmol), Pd/C (250 mg, 10%, wet), and methanol (25 mL) was hydrogenated on a Parr apparatus at 50 psi $H_2$ for 13 hours. The reaction was filtered through celite, and the solvent removed in vacuo to yield compound 108 (265 mg) as a light yellow oil, $^1$H NMR (CDCl$_3$, 300 MHz): 1.24 (t,j=7.0 Hz, 3H), 1.60 (s, 2H), 1.82 (s, 1H), 2.36 (d,j=1.7 Hz, 1H), 2.94 (d,j=11.4 Hz, 2H), 3.16 (d,j=11.5 Hz, 2H), 4.11 (q,j=6.9 Hz, 2H), 4.73 (bs, 1H); ESI (+) MS: 171 (M+H$^+$), which was used without further purification.

The title compound was prepared by the general coupling procedure of Example 1 using compound 100 (659 mg, 0.720 mmol), amine 108 (245 mg, 1.44 mmol), and manganese(IV) oxide (626 mg, 7.20 mmol) to provide compound 21 (129 mg, 18% yield) as a blue solid, Mp=>350° C.; ESI (+) MS: 969 (M+H$^+$); UV/Vis: $\lambda_{max}$=639.7 nm.

EXAMPLE 27

Synthesis of Compound No. 22 (see Table 1 for Structure)

The title compound was prepared by the general coupling procedure of Example 1 using compound 100 (6.19 g, 6.70 mmol), piperidin-4-yl-carbamic acid isopropyl ester (EP 467325, 2.52 g, 13.5 mmol), and manganese(IV) oxide (5.86 g, 67.0 mmol) to provide compound 22 (2.39 g, 36% yield) as a blue solid, Mp=>300° C.; ESI (+) MS: 985 (M+H$^+$); UV/Vis: $\lambda_{max}$=643.0 nm.

EXAMPLE 28

Synthesis of Compound No. 29 (see Table 1 for Structure)

The title compound was prepared by the general deacetylation procedure of Example 2 using compound 22 (0.850 g, 0.860 mmol) to provide compound 29 (0.640 g, 78%) as a blue solid, Mp=222-225° C.; ESI (+) MS: 911 (M+H$^+$); UV/Vis: $\lambda_{max}$=643.0 nm.

EXAMPLE 29

Synthesis of Compound No. 23 (see Table 1 for Structure)

The precursor amine used in the preparation of compound 23 was prepared as follows:

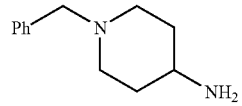
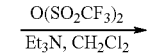
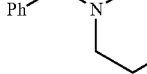
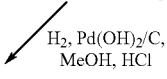
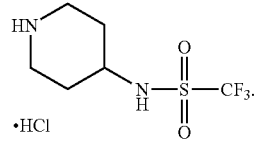

4-Amino-1-benzylpiperidine (685 mg, 3.61 mmol) in methylene chloride (10 mL) was treated with trifluoromethanesulfonic anhydride (1.6 mL, 3.4 mmol) and triethylamine (0.8 mL, 5.7 mmol) at 0° C. After warming to rt overnight the reaction was added to a saturated NaHCO$_3$ solution (100 mL) and extracted with methylene chloride (3×25 mL). The combined organics were dried over Na$_2$SO$_4$ and concentrated in vacuo. The resulting residue was purified via MPLC (silica gel, gradient 0-5%, methanol in methylene chloride) to yield compound 109a (844 mg, 2.6 mmol, 73%). ESI (+) MS: 323 (M+H$^+$).

Compound 109a (844 mg, 2.62 mmol) was dissolved in methanol (15 mL) and treated with HCl in diethylether (2 M, 1.5 mL). The solvent was removed under reduced pressure and the residue was redissolved in methanol (50 mL). Palladium hydroxide on carbon (20%, 152 mg, 0.22 mmol) was added and the reaction was treated with H$_2$ (55 psi). After 15 h the reaction was filtered (celite, vacuum) and concentrated in vacuo. The resulting amine salt 109 (620 mg), $^1$H NMR (DMSO-d$_6$, 300 MHz): δ 10.15 (s, 1H), 9.47 (s, 1H), 9.29 (s, 1H), 3.68 (m, 1H), 3.25 (m, 2H), 3.02 (m, 2H), 1.95 (dd, J=13.4, 2.8 Hz, 2H), 1.76 (m, 2H); ESI (+) MS: 233 (M+H$^+$), was used without further purification.

The title compound was prepared by the general coupling procedure of Example 1 using compound 100 (1.58 g, 1.73 mmol), amine 109 (580 mg, 2.16 mmol), manganese(IV) oxide (1.37 g, 15.7 mmol) and triethylamine (0.90 mL, 6.5 mmol) to provide compound 23 (351 mg, 20% yield) as a blue solid, Mp=238-240° C.; ESI (+) MS: 1031 (M+H$^+$); UV/Vis: $\lambda_{max}$=638.7 nm.

EXAMPLE 30

Synthesis of Compound No. 38 (see Table 1 for Structure)

The title compound was prepared by the general deacetylation procedure of Example 2 using compound 23 (103 mg, 0.099 mmol) to provide compound 38 (22 mg, 22% yield) as a blue solid, Mp=245-246° C.; APCI (+) MS: 989 (M+H$^+$); UV/Vis: $\lambda_{max}$=639.7 nm.

EXAMPLE 31

Synthesis of Compound No. 24 (see Table 1 for Structure)

The precursor amine used in the preparation of compound 24 was prepared as follows:

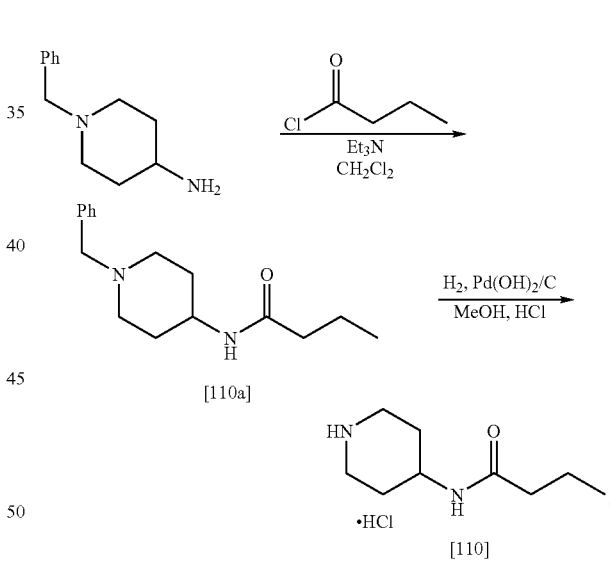

Butyryl chloride (1.30 mL, 12.4 mmol) was added to a stirred solution of 4-amino-1-benzylpiperidine (700 mg, 3.68 mmol), triethylamine (0.5 mL, 3.6 mmol), 4-dimethylaminopyridine (5 mg, 0.04 mmol), methylene chloride (10 mL) at 0° C. After addition, the reaction was allowed to come to rt and stirred for 4 days. After removal of the solvents in vacuo, the resulting residue was purified via MPLC (silica gel, gradient 2.5-7.5%, methanol in methylene chloride) to yield compound 110a (408 mg, 1.57 mmol, 42%). ESI (+) MS: 261 (M+H$^+$).

A mixture of compound 110a (400 mg, 1.54 mmol), palladium hydroxide on carbon (20%, 122 mg, 0.17 mmol), and methanol (25 mL) was hydrogenated on a Parr apparatus at 55 psi H$_2$ for 2 days. The reaction was filtered through celite, and the solvent removed in vacuo to yield compound 110 (345 mg), $^1$H NMR (CD$_3$OD, 300 MHz): δ3.93 (m, 1H), 3.41 (m, 2H), 3.09 (m, 2H), 2.20 (t, J=12.6 Hz, 2H), 2.09 (dd, J=13.8, 2.0 Hz, 2H), 1.70 (m, 2H), 1.64 (m, 2H), 0.94 (t, J=7.4 Hz, 3H); ESI (+) MS: 171 (M+H$^+$), which was used without further purification.

The title compound was prepared by the general coupling procedure of Example 1 using compound 100 (997 mg, 1.09 mmol), amine 110 (345 mg, 1.67 mmol), manganese(IV) oxide (1.10 g, 12.6 mmol), and triethylamine (2.0 mL, 14 mmol) to provide compound 24 (291 mg, 28% yield) as a blue solid, Mp=222-226° C.; ESI (+) MS: 969 (M+H$^+$); UV/Vis: $\lambda_{max}$=643.2 nm.

EXAMPLE 32

Synthesis of Compound No. 36 (see Table 1 for Structure)

The title compound was prepared by the general deacetylation procedure of Example 2 using compound 24 (83 mg, 0.086 mmol) to provide compound 36 (46 mg, 58% yield) as a blue solid, Mp=228-230° C.; APCI (+) MS: 927 (M+H$^+$); UV/Vis: $\lambda_{max}$=643.9 nm.

EXAMPLE 33

Synthesis of Compound No. 25 (see Table 1 for Structure)

The precursor amine used in the preparation of compound 25 was prepared as follows:

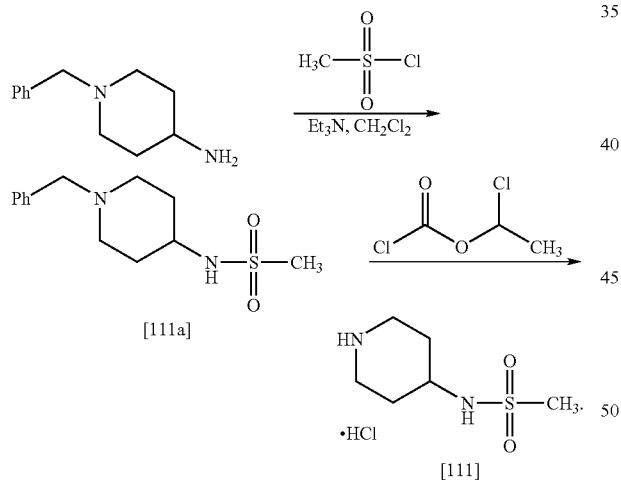

Methanesulfonyl chloride (0.5 mL, 6.4 mmol) was added to a stirred solution of 4-amino-1-benzylpiperidine (670 mg, 3.53 mmol), triethylamine (0.9 mL, 6.5 mmol), and methylene chloride (10 mL) at 0° C. After addition, the reaction stirred under an atmosphere of N$_2$ at 0° C. for 30 minutes, warmed to rt, and stirred an additional 32 h. After removal of the solvents in vacuo, the resulting residue was purified via MPLC (silica gel, gradient 0-10%, methanol in methylene chloride) to yield compound 111a (844 mg, 3.15 mmol, 89% yield), ESI (+) MS: 269 (M+H$^+$).

Compound 111a (460 mg, 1.72 mmol) was dissolved in methylene chloride (10 mL) and treated with 1-chloroethyl chloroformate (0.23 mL, 2.1 mmol) at 0° C. After 15 minutes the reaction was heated to reflux for 2 h. The solvent was removed under reduced pressure and the residue was dissolved in methanol (10 mL) and heated at reflux for 1 h. The reaction was reduced in vacuo and the resulting mixture of compound 111a and amine salt 111 was used without further purification. ESI (+) MS: 179(M+H$^+$).

The title compound was prepared by the general coupling procedure of Example 1 using compound 100 (1.43 g, 1.56 mmol), amine 111 (413 mg, 1.93 mmol), manganese(IV) oxide (1.01 g, 11.6 mmol), and triethylamine (2.0 mL, 14 mmol) to provide compound 25 (390 mg, 26% yield) as a blue solid, Mp=256-257° C.; ESI (+) MS: 977 (M+H$^+$); UV/Vis: $\lambda_{max}$=642.0 nm.

EXAMPLE 34

Synthesis of Compound No. 27 (see Table 1 for Structure)

The title compound was prepared by the general deacetylation procedure of Example 2 using compound 25 (98 mg, 0.10 mmol) to provide compound 27 (78 mg, 83% yield) as a blue solid, Mp=270-273° C.; ESI (+) MS: 935 (M+H$^+$); UV/Vis: $\lambda_{max}$=641.0 nm.

EXAMPLE 35

Synthesis of Compound No. 28 (see Table 1 for Structure)

The precursor amine used in the preparation of compound 28 was prepared as follows:

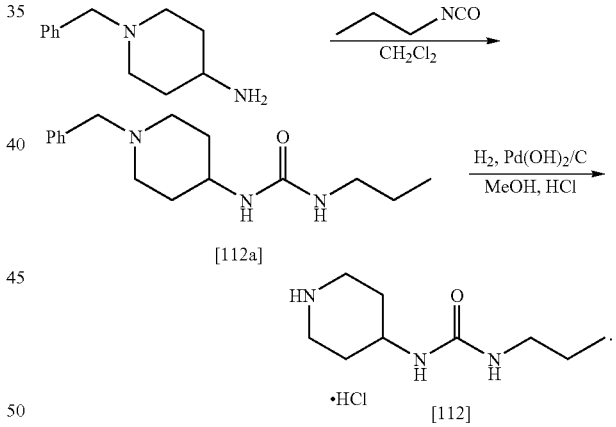

4-Amino-1-benzylpiperidine (1.01 g, 5.3 mmol) in methylene chloride (10 mL) was treated with N-propyl isocyanate (2.5 mL, 26.7 mmol) and diisopropylethylamine (3.5 mL, 20.1 mmol) at rt. After 16 h the reaction was added to a saturated NaHCO$_3$ solution (100 mL) and extracted with methylene chloride (3×25 mL). The combined organics were dried over Na$_2$SO$_4$ and reduced in vacuo. The resulting residue was purified via MPLC (silica gel, gradient 2.5-12.5%, methanol in methylene chloride) to yield compound 112a (1.13 g, 4.12 mmol, 78% yield), ESI (+) MS: 276 (M+H$^+$).

A mixture of compound 112a (1.13 g, 4.12 mmol), palladium hydroxide on carbon (20%, 325 mg, 0.46 mmol), and methanol (25 mL) was hydrogenated on a Parr apparatus at 55 psi H$_2$ for 4 days. The reaction was filtered through celite, and the solvent removed in vacuo to yield compound 112 (862 mg), $^1$H NMR (CD$_3$OD, 300 MHz): δ 3.72 (m, 1H), 3.34 (m, 2H), 3.09-3.04 (m, 2H), 3.05-2.97 (m, 2H), 2.06 (dd, J=13.8, 2.8 Hz, 2H), 1.59 (m, 2H), 1.48 (m, 2H), 0.91 (t, J=7.4 Hz, 3H), which was used without any further purification.

The title compound was prepared by the general coupling procedure of Example 1 using compound 100 (1.68 g, 1.84 mmol), amine 112 (862 mg, 3.9 mmol), manganese(IV) oxide (2.0 g, 23 mmol), and triethylamine (1.0 mL, 7.2 mmol) to provide compound 28 (1.27 g, 70% yield) as a blue solid, Mp=260-263° C.; ESI (+) MS: 984 (M+H$^+$); UV/Vis: λ$_{max}$=644.5 nm.

EXAMPLE 36

Synthesis of Compound No. 26 (see Table 1 for Structure)

The title compound was prepared by the general deacetylation procedure of Example 2 using compound 28 (300 mg, 0.305 mmol) to provide compound 26 (187 mg, 65% yield) as a blue solid, Mp=265-266° C.; ESI (+) MS: 942 (M+H$^+$); UV/Vis: λ$_{max}$=644.0 nm.

EXAMPLE 37

Synthesis of Compound No. 32 (see Table 1 for Structure)

The title compound was prepared by the general coupling procedure of Example 1 using compound 100 (2.25 g, 2.76 mmol), piperidin-4-yl-carbamic acid methyl ester (873 mg, 5.52 mmol, *Biorg. Med. Chem Lett*. 2001, 2475-2480), and manganese(IV) oxide (2.40 g, 27.6 mmol) to provide compound 32 (2.27 g, 86% yield) as a blue solid, Mp=149-153° C.; ESI (+) MS: 957 (M+H$^+$); UV/Vis: λ$_{max}$=645.5 nm.

EXAMPLE 38

Synthesis of Compound No. 30 (see Table 1 for Structure)

The title compound was prepared by the general deacetylation procedure of Example 2 using compound 32 (438 mg, 0.458 mmol) to provide compound 30 (386 mg, 92%) as a blue solid, Mp=212-225° C.; ESI (+) MS: 915 (M+H$^+$); UV/Vis: λ$_{max}$=643.1 nm.

EXAMPLE 39

Synthesis of Compound No. 33 (see Table 1 for Structure)

The title compound was prepared by the general coupling procedure of Example 1 using compound 100 (1.20 g, 1.31 mmol), 4-aminopiperidine (0.45 mL, 4.3 mmol), and manganese(IV) oxide (774 mg, 8.90 mmol) to provide compound 33 (431 mg, 37% yield) as a blue solid, Mp=278-279° C.; ESI (+) MS: 899 (M+H$^+$); UV/Vis: λ$_{max}$=647.7 nm.

EXAMPLE 40

Synthesis of Compound No. 39 (see Table 1 for Structure)

The title compound was prepared by the general deacetylation procedure of Example 2 using compound 33 (110 mg, 0.122 mmol) to provide 39 (95 mg, 91% yield) as a blue solid, Mp=265-266° C.; ESI (+) MS: 857 (M+H$^+$); UV/Vis: λ$_{max}$=647.8 nm.

EXAMPLE 41

Synthesis of Compound No. 34 (see Table 1 for Structure)

The precursor amine used in the preparation of compound 34 was prepared as follows:

4-Amino-1-benzylpiperidine (990 mg, 5.21 mmol) in methylene chloride (10 mL) was treated with N-ethyl isocyanate (2.0 mL, 25 mmol), and diisopropylethylamine (1.8 mL, 10 mmol) at rt. After 16 h the reaction was added to a saturated NaHCO$_3$ solution (100 mL) and extracted with methylene chloride (3×25 mL). The combined organics were dried over Na$_2$SO$_4$ and reduced in vacuo. The resulting residue was purified via MPLC (silica gel, gradient 2.5-12.5%, methanol in methylene chloride) to yield compound 113a (1.14 g, 4.39 mmol, 84% yield), ESI (+) MS: 262 (M+H$^+$).

A mixture of compound 113a (1.06 g, 4.08 mmol), palladium hydroxide on carbon (20%, 350 mg, 0.50 mmol), and methanol (50 mL) was hydrogenated on a Parr apparatus at 55 psi H$_2$ for 4 hours. The reaction was filtered through celite, and the solvent removed in vacuo to yield a mixture of compounds 113a and 113, $^1$H NMR (CD$_3$OD, 300 MHz): δ 3.79 (m, 1H), 3.41 (m, 2H), 3.22-3.15 (m, 2H), 3.15-3.05 (m, 2H), 2.09 (m, 2H), 1.73 (m, 2H), 1.13 (t, J=7.2 Hz, 3H), which were used without any further purification.

The title compound was prepared by the general coupling procedure of Example 1 using compound 100 (2.00 g, 2.16 mmol), amine 113 (1.05 g, 5.07 mmol), manganese(IV) oxide (2.20 g, 25 mmol) and triethylamine (1.5 mL, 11 mmol) to provide compound 34 (350 mg, 17%) as a blue solid, Mp=234-236° C.; ESI (+) MS: 970 (M+H$^+$); UV/Vis: λ$_{max}$=644.6 nm.

EXAMPLE 42

Synthesis of Compound No. 37 (see Table 1 for Structure)

The title compound was prepared by the general deacetylation procedure of Example 2 using compound 34 (200 mg, 0.206 mmol) to provide compound 37 (116 mg, 61%) as a blue solid, Mp=321-322° C.; APCI (+) MS: 928 (M+H+); UV/Vis: $\lambda_{max}$=645.0 nm.

EXAMPLE 43

Synthesis of Compound No. 35 (see Table 1 for Structure)

The precursor amine used in the preparation of compound 35 was prepared as follows:

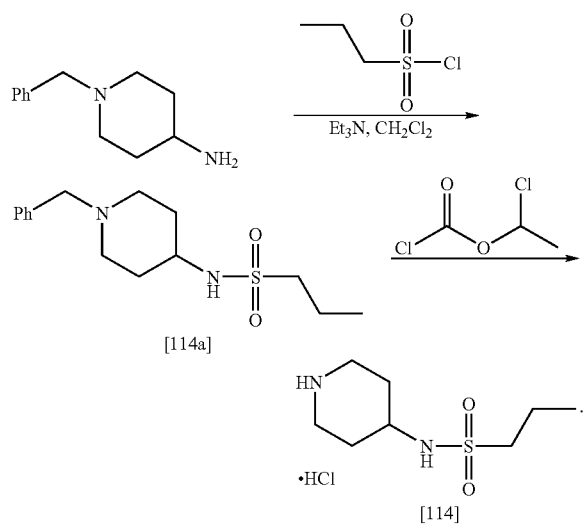

Propanesulfonyl chloride (0.9 mL, 7.9 mmol) was added to a stirred solution of 4-amino-1-benzylpiperidine (890 mg, 4.68 mmol), triethylamine (0.8 mL, 5.7 mmol), and methylene chloride (10 mL) at 0° C. After addition, the reaction stirred under an atmosphere of $N_2$ at 0° C. for 30 minutes, warmed to rt, and stirred an additional 32 h. After removal of the solvents in vacuo, the resulting residue was purified via MPLC (silica gel, gradient 0-5%, methanol in methylene chloride) to yield compound 114a (1.02 g, 3.44 mmol, 89%), $^1$H NMR (CDCl$_3$, 300 MHz):δ7.34-7.25 (m, 5H), 4.05 (d, J=7.7 Hz, 1H), 3.49 (s, 2H), 3.31 (m, 1H), 2.98 (m, 2H), 2.80 (m, 2H), 2.11 (m, 2H), 1.99 (m, 2H), 1.84 (m, 2H), 1.58 (m, 2H), 1.05 (t, J=7.4 Hz, 3H); ESI (+) MS: 297 (M+H+).

Compound 114a (883 mg, 2.98 mmol) was dissolved in methylene chloride (10 mL) and treated with 1-chloroethyl chloroformate (0.23 mL, 2.1 mmol) at 0° C. After 15 minutes the reaction was heated to reflux for 2 h. The solvent was removed under reduced pressure and the residue was dissolved in methanol (10 mL) and heated at reflux for 1 h. The reaction was reduced in vacuo and the resulting compound 114 (769 mg) was used without further purification.

The title compound was prepared by the general coupling procedure of Example 1 using compound 100 (1.24 g, 1.36 mmol), amine 114 (769 mg, 3.17 mmol), manganese(IV) oxide (1.40 g, 16 mmol), and triethylamine (0.8 mL, 6 mmol) to provide compound 35 (640 mg, 47% yield) as a blue solid, Mp=220-226° C.; ESI (+) MS: 1005 (M+H+); UV/Vis: $\lambda_{max}$=641.7 nm.

EXAMPLE 44

Synthesis of Compound No. 67 (see Table 1 for Structure)

The title compound was prepared by the general deacetylation procedure of Example 2 using compound 35 (198 mg, 0.197 mmol) to provide compound 67 (110 mg, 58% yield) as a blue solid, Mp=215-216° C.; APCI (+) MS: 963 (M+H+); UV/Vis: $\lambda_{max}$=641.5 nm.

EXAMPLE 45

Synthesis of Compound No. 40 (see Table 1 for Structure)

The precursor amine used in the preparation of compound 40 was prepared as follows:

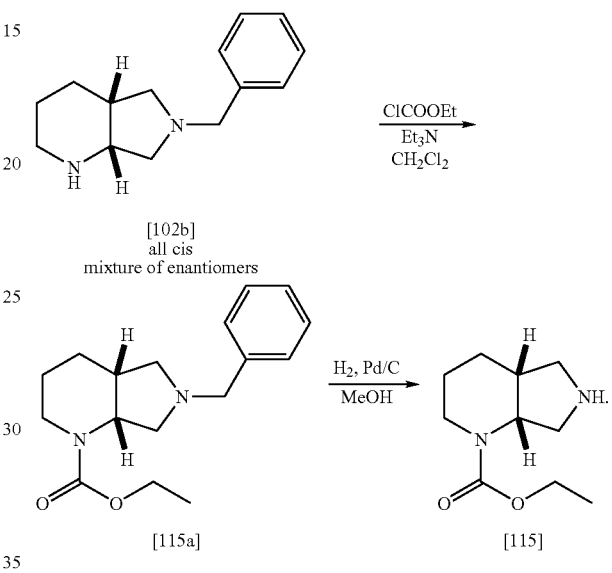

Ethyl chloroformate (0.491 mL, 5.14 mmol) was added to a stirred solution of compound 102b (1.01 g, 4.67 mmol, U.S. Pat. No. 5,654,318), triethylamine (0.980 mL, 7.01 mmol), and methylene chloride (20 mL) at 0° C. The reaction was stirred under an atmosphere of $N_2$ at 0° C. for 30 minutes, quenched with sat. NaHCO$_3$ and the aqueous layer extracted with methylene chloride (×1). The organics were combined and dried over Na$_2$SO$_4$. Filtration, followed by removal of the solvent in vacuo, yielded a residue that was purified via flash chromatography (1:1, ethyl acetate hexanes) to yield compound 115a (1.06 g, 79% yield) as a colorless oil, $^1$H NMR (CDCl$_3$, 300 MHz): 1.24 (t,j=7.1 Hz, 3H), 1.37-1.72 (m, 4H), 2.10-2.16 (m, 1H), 2.51 (d,j=8.9 Hz, 1H), 2.64 (t,j=8.2 Hz, 1H), 2.75-2.84 (m, 3H), 3.66 (dd, j=24.2, 13.1 Hz, 2H), 3.92 (bs, 1H), 4.11 (q,j=7.1 Hz, 2H), 4.63 (bs, 1H), 7.22-7.32 (m, 5H); ESI (+) MS: 289 (M+H+).

A mixture of compound 115a (1.05 g, 3.64 mmol), Pd/C (300 mg, 10%, wet), and methanol (25 mL) was hydrogenated on a Parr apparatus at 50 psi H$_2$ for 14.5 hours. The reaction was filtered through celite, and the solvent removed in vacuo to yield compound 115 (767 mg, quant., wet with methanol) as a light yellow oil, $^1$H NMR (CDCl$_3$, 500 MHz): 1.27 (t,j=3.5 Hz, 3H), 1.38-1.45 (m, 2H), 1.68-1.73 (m, 2H), 2.04-2.07 (m, 2H), 2.75-2.83 (m, 3H), 3.09-3.18 (m, 2H), 4.00 (d,j=11.5 Hz, 1H), 4.11-4.17 (m, 2H), 4.52-4.54 (m, 1H); ESI (+) MS: 199 (M+H+), which was used with out further purification.

The title compound was prepared by the general coupling procedure of Example 1 using compound 100 (1.65 g, 1.80 mmol), amine 115 (712 mg, 3.59 mmol) and manganese(IV)

oxide (1.56 g, 18.0 mmol) to provide compound 40, Diastereomer A (555 mg (31%) as a blue solid (higher $R_f$ using ethyl acetate as eluent) and compound 40b, Diastereomer B (660 mg, 37% yield, not shown in Table) as a blue solid (lower $R_f$ using ethyl acetate as eluent), Mp=>300° C.; ESI (+) MS: 997 (M+H$^+$); UV/Vis: $\lambda_{max}$=644.0 nm.

EXAMPLE 46

Synthesis of Compound No. 42 (see Table 1 for Structure)

The title compound was prepared by the general deacetylation procedure of Example 2 using compound 40 (110 mg, 0.110 mmol) to provide compound 42 (97 mg, 92% yield) as a blue solid, as mixture of diastereomers (as determined by HPLC and $^1$H NMR), Mp=>300° C.; ESI (+) MS: 955 (M+H$^+$); UV/Vis: $\lambda_{max}$=644.0 nm.

EXAMPLE 47

Synthesis of Compound No. 41 (see Table 1 for Structure)

The precursor amine used in the preparation of compound 41 was prepared as follows:

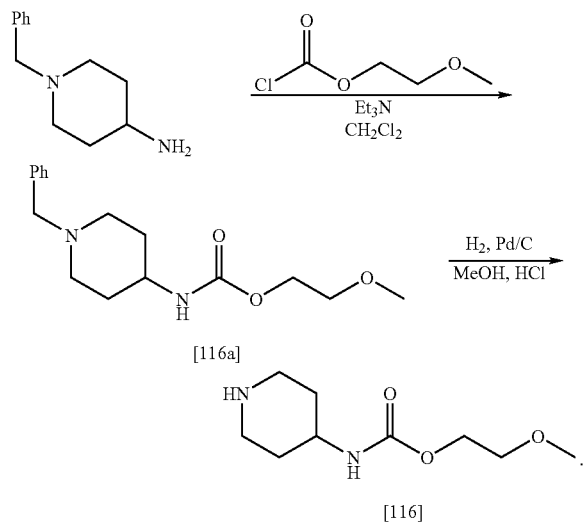

A stirred solution of 4-amino-1-benzylpiperidine (3.0 mL, 15.0 mmol) and triethylamine (3.4 mL, 24.4 mmol) in methylene chloride (50 mL) was cooled to 0° C. using an ice bath. To the reaction flask was added chloroformic acid, 2-methoxyethyl ester (2.00 mL, 17.5 mmol). The reaction was stirred under nitrogen at 0° C. for 45 minutes, quenched with saturated sodium bicarbonate (150 mL), extracted with methylene chloride (×3), and concentrated in vacuo to provide an oily residue. The residue was purified by flash chromatography (1:19, methanol:methylene chloride) to yield 4.64 g of compound 116a as a pale yellow oil, $^1$H NMR (300 MHz, CDCl$_3$) δ1.36-1.52 (m, 2H), 1.90 (d, 2H), 2.03-2.17 (t, 2H), 2.78 (d, 2H), 3.38 (s, 3.44-3.64 (m, 5H), 4.13-4.31 (m, 2H), 4.69 (d, 1H), 7.19-7.35 (m, 5H); ESI (+) MS: 293.

Compound 116a (4.64 g, 15.9 mmol) was dissolved in methanol (75 mL) and reacted with Pd/C (1.00 g, 10 wt %, wet) on a Parr apparatus at room temperature under 50 psi of hydrogen for 16 hours. The reaction was filtered through celite and the solids rinsed with methanol (250 mL). The filtrate and rinse were concentrated down to provide 3.13 g (97% yield) of amine 116 as a light yellow oil. $^1$H NMR (300 MHz, CDCl$_3$) δ 1.23-1.40 (m, 2H), 1.93 (d, 2H), 2.08 (s, 2H), 2.57-2.74 (t, 2H), 3.06 (d, 2H), 3.38 (s, 3H), 3.49-3.67 (m, 2H), 4.12-4.32 (m, 2H), 4.85 (s, 1H). ESI (+) MS: 203.

The title compound was prepared by the general coupling procedure of Example 1 using compound 100 (4.50 g, 5.16 mmol), amine 116 (3.13 g, 15.5 mmol), and manganese(IV) oxide (4.60 g, 52.9 mmol) to provide compound 41 (4.34 g, 84%) as a blue solid, Mp=175-183° C.; ESI (+) MS: 1001 (M+H$^+$); UV/Vis: $\lambda_{max}$=642.9 nm.

EXAMPLE 48

Synthesis of Compound No. 44 (see Table 1 for Structure)

The precursor amine used in the preparation of compound 44 was prepared as follows:

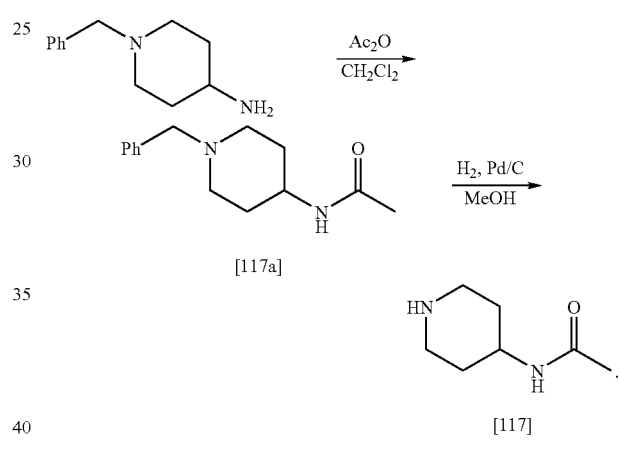

4-Amino-1-benzylpiperidine (1.31 g, 6.89 mmol) in methylene chloride (20 mL) was treated with acetic anhydride (0.80 mL, 8.5 mmol) and triethylamine (2.0 mL, 14 mmol) at rt. After 24 h the reaction was added to a saturated NaHCO$_3$ solution (100 mL) and extracted with methylene chloride (3×25 mL). The combined organics were dried over Na$_2$SO$_4$ and reduced in vacuo. The resulting residue was purified via MPLC (silica gel, gradient 2.5-12.5%, methanol in methylene chloride) to yield compound 117a (1.35 g, 5.8 mmol, 84% yield), ESI (+) MS: 233 (M+H$^+$).

A mixture of compound 117a (1.35 g, 5.8 mmol), palladium on carbon (10%, 421 mg, 0.79 mmol), and methanol (25 mL) was hydrogenated on a Parr apparatus at 55 psi H$_2$ for 24 hours. The reaction was filtered through celite, and the solvent removed in vacuo to yield compound 117, $^1$H NMR (CDCl$_3$, 300 MHz): δ5.45 (s, 1H), 3.87 (m, 1H), 3.07 (m, 2H), 2.69 (td, J=12.2, 2.5 Hz, 2H), 1.97 (s, 3H), 195 (m, 2H), 1.75 (s, 1H), 1.31 (m, 2H), which was used without any further purification.

The title compound was prepared by the general coupling procedure of Example 1 using compound 100 (1.83 g, 2.0 mmol), compound 17 (950 mg, 6.7 mmol), and manganese (IV) oxide (1.09 g, 12.5 mmol) to provide compound 44 (926 mg, 49% yield) as a blue solid, Mp=232-234° C.; ESI (+) MS: 941 (M+H$^+$); UV/Vis: $\lambda_{max}$=643.6 nm.

EXAMPLE 49

Synthesis of Compound No. 43 (see Table 1 for Structure)

The title compound was prepared by the general deacetylation procedure of Example 2 using compound 44 (272 mg, 0.289 mmol) to provide compound 43 (208 mg, 80%) as a blue solid, Mp=232-236° C.; ESI (+) MS: 899 (M+H$^+$); UV/Vis: $\lambda_{max}$=643.9 nm.

EXAMPLE 50

Synthesis of Compound No. 47 (see Table 1 for Structure)

The precursor amine used in the preparation of compound zz was prepared as follows:

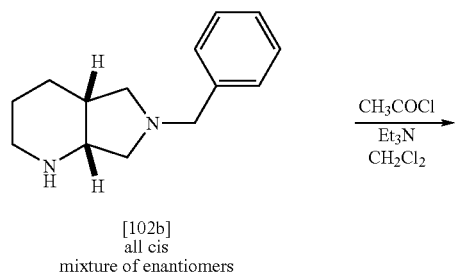

[102b]
all cis
mixture of enantiomers

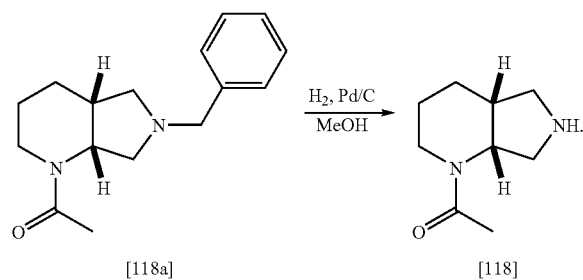

[118a]      [118]

Acetyl chloride (0.373 mL, 5.24 mmol) was added to a stirred solution of compound 102b (1.03 g, 4.76 mmol), triethylamine (1.0 mL, 7.14 mmol), and methylene chloride (20 mL) at 0° C. The reaction was stirred under an atmosphere of N$_2$ at 0° C. for 1 hour. The reaction was quenched with sat. NaHCO$_3$, and the aqueous layer was extracted with methylene chloride (×1). The organics were combined and dried over Na$_2$SO$_4$. Filtration followed by removal of the solvent in vacuo yielded a residue that was purified via flash chromatography (9:1, methylene chloride:methanol) to yield compound 118a (1.09 g, 87%) as a light yellow oil, $^1$H NMR (CDCl$_3$, 300 MHz): 1.31-1.78 (m, 4H), 2.06-2.39 (m, 4H), 2.48-2.90 (m, 4.5H, conformer), 3.06-3.16 (m, 0.5H, conformer), 3.58-3.75 (m, 2.5H, conformer), 4.32-4.44 (m, 1H), 5.03 (q,j=8.5 Hz, 0.5H, conformer), 7.21-7.35 (m, 5H); ESI (+) MS: 259 (M+H$^+$).

A mixture of compound 118a (2.18 g, 8.43 mmol), Pd/C (500 mg, 10%, wet), and methanol (50 mL) was hydrogenated on a Parr apparatus at 50 psi H$_2$ for 15 hours. The reaction was filtered through celite, and the solvent removed in vacuo to yield compound 118 (1.55 g, quant., wet with methanol) as a light yellow oil, $^1$H NMR (CDCl$_3$, 500 MHz): 1.35-1.53 (m, 2H), 1.73-1.77 (m, 2H), 2.08-2.14 (m, 4H), 2.56 (t,j=10.0 Hz, 0.4H, conformer), 2.77 (t,j=10.4 Hz, 0.6H, conformer), 2.82-2.86 (m, 2H), 2.96 (t,j=10.0 Hz, 0.4H, conformer), 2.82-2.86 (m, 2H), 3.05-3.09(m, 1H), 3.16-3.25 (m, 1.6H, conformer), 3.66 (d,j=12.7 Hz, 0.6H, conformer), 4.27 (q, j=8.1 Hz, 0.4H, conformer), 4.51 (d,j=13.9 Hz, 0.4H, conformer), 4.97 (q,j=8.1 Hz, 0.6H, conformer); ESI (+) MS: 169 (M+H$^+$), that was used with out further purification.

The title compound was prepared by the general coupling procedure of Example 1 using compound 100 (3.81 g, 4.16 mmol), amine 118 (1.40 g, 8.32 mmol) and manganese(IV) oxide (3.62 g, 41.6 mmol) to provide compound 47 (916 mg, 23% yield) as a blue solid, Mp=148-149° C.; ESI (+) MS: 967 (M+H$^+$); UV/Vis: $\lambda_{max}$=644.0 nm.

EXAMPLE 51

Synthesis of Compound No. 46 (see Table 1 for Structure)

The title compound was prepared by the general deacetylation procedure of Example 2 using compound 47 (214 mg, 0.221 mmol) to provide compound 46 (178 mg, 87% yield) as a blue solid, Mp=148-149° C.; ESI (+) MS: 967 (M+H$^+$); UV/Vis: $\lambda_{max}$=644.0 nm.

EXAMPLE 52

Synthesis of Compound Nos. 45 and 49 (see Table 1 for Structure)

The precursor amine used in the preparation of compounds 45 and 49 was prepared as follows:

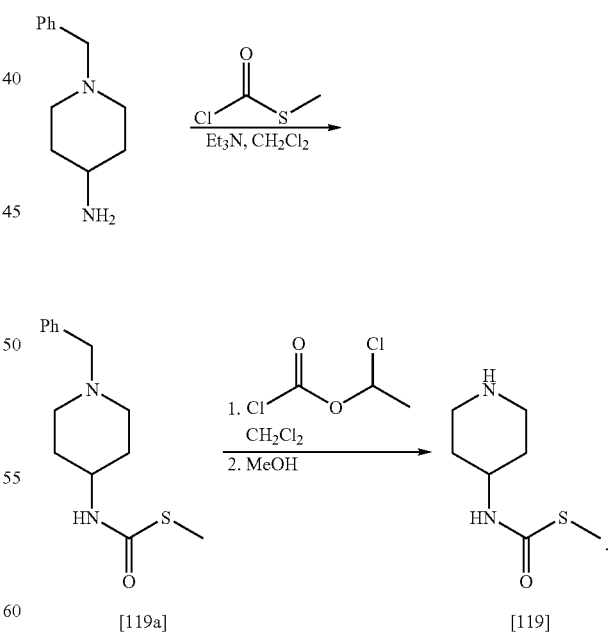

[119a]      [119]

Methylthiolchloroformate (1.0 g, 9.04 mmol) was added to a stirred solution of commercially available 4-amino-1-benzylpiperidine (1.68 ML, 8.22 mmol), triethylamine (1.71 mL, 12.3 mmol), and methylene chloride (30 mL) at 0° C. The reaction was stirred at 0° C. under an atmosphere of N$_2$ for 30 minutes, quenched with sat. NaHCO₃ and the aqueous layer was extracted once with methylene chloride. The organics were combined and dried over Na₂SO₄. Filtration, followed by removal of the solvent in vacuo, yielded a residue that was purified via flash chromatography (3:2, ethyl acetate:hexanes) to yield compound 119a (2.17 g, 100%) as a white solid, ¹H NMR (CDCl₃, 300 MHz): 1.41-1.53 (m, 2H), 1.93 (d,j=11.6 Hz, 2H), 2.06-2.15 (m, 2H), 2.34 (s, 3H), 2.79 (d,j=11.9 Hz, 2H), 3.79 (s, 2H), 3.79 (bs, 1H), 5.22 (bs, 1H), 7.23-7.34 (m, 5H); ESI (+) MS: 265 (M+H⁺).

α-Chloroethylchloroformate (0.870 mL, 8.06 mmol) was added slowly (over a period of 15 minutes) to a stirred solution of 119a (2.13 g, 8.06 mmol) in methylene chloride (20 mL) cooled in a brine/ice bath. The brine/ice bath was removed, and the reaction was refluxed with stirring for 1.5 hours. The reaction was cooled to ambient temperature and methanol (6 mL) was added. The reaction was again refluxed with stirring for 2 hours. The reaction was cooled to ambient temperature and the solvent was removed in vacuo. The resulting residue was purified via flash chromatography (1:9:40, NH₄OH:methanol:methylene chloride) to yield compound 119 (1.07 g, 74%) as a yellow semi-solid, ¹H NMR (CDCl₃, 300 MHz): 1.34-1.46 (m, 2H), 1.96-2.00 (m, 2H), 2.34 (s, 3H), 2.66-2.75 (m, 2H), 3.08-3.14 (m, 2H), 3.88-3.92 (m, 1H), 5.62 (bs, 1H); ESI (+) MS: 175 (M+H⁺), which was used without further purification.

The title compounds were prepared by the general coupling procedure of Example 1 using compound 100 (2.68 g, 2.93 mmol), amine 119 (1.02 g, 5.85 mmol) and manganese (IV) oxide (2.55 g, 29.3 mmol) to provide 859 mg of a blue solid (impure compound 45, higher $R_f$ using ethyl acetate as an eluent) and 603 mg of a blue solid (impure compound 49, lower $R_f$ using ethyl acetate as an eluent) after flash chromatography.

Impure compound 45 was purified via MPLC (gradient, 2-20% tetrahydrofuran:methylene chloride, followed by gradient, 1.25-2.5% methanol:methylene chloride) to provide compound 45 (162 mg, 6% yield), Mp=150-155° C.; ESI (+) MS: 973 (M+H⁺); UV/Vis: $\lambda_{max}$=642.0 nm.

Impure compound 49 was purified via MPLC (gradient, 1.25-4.5% methanol:methylene chloride) followed by preparatory thin layer chromatography (1.0 mm silica, ethyl acetate, ~50 mg per plate, each plate resolved 6 times) to provide compound 49 (87 mg), Mp=>300° C.; ESI (+) MS: 1099 (M+H⁺); UV/Vis: $\lambda_{max}$=643.1 nm.

EXAMPLE 53

Synthesis of Compound No. 48 (see Table 1 for Structure)

The title compound was prepared by the general coupling procedure of Example 1 using compound 100 (5.20 g, 5.96 mmol), 4-(tert-butoxycarbonylamino)piperidine (240 mg, 11.9 mmol) and manganese(IV) oxide (5.20 g, 59.8 mmol) to provide 2.15 g (36%) of a blue solid, Mp=218-228° C.; ESI (+) MS: 999 (M+H⁺); UV/Vis: $\lambda_{max}$=643.1 nm.

EXAMPLE 54

Synthesis of Compound No. 52 (see Table 1 for Structure)

The title compound was prepared by the general deacetylation procedure of Example 2 using compound 48 (0.300 g, 0.300 mmol) to provide compound 52 (0.273 g, 95%) as of a blue solid, Mp=230-232° C.; ESI (−) MS: 956 (M+H⁺); UV/Vis: $\lambda_{max}$=643.5 nm.

EXAMPLE 55

Synthesis of Compound No. 50 (see Table 1 for Structure)

A mixture of compound 45 (397 mg, 0.480 mmol), N-methylpiperazine (0.230 mL, 2.04 mmol) and methyl sulfoxide (5 mL) was stirred at ambient temperature for 6 days. The reaction was diluted with methylene chloride and poured over water. The aqueous layer was extracted with methylene chloride (×2) and the combined organics were washed with water (×2) then brine (×1) and dried over Na₂SO₄. Filtration followed by removal of the solvent in vacuo yielded a residue that was purified via MPLC (gradient, 2.5-10% methanol:methylene chloride) to yield compound 50 as a blue solid (74 mg, 18% yield). Mp=>300° C., ESI (+) MS: 1025 (M+H⁺), UV/Vis: $\lambda_{max}$=644.9 nm.

Example 56

Synthesis of Compound No. 51 (see Table 1 for Structure)

The title compound was prepared by the general coupling procedure of Example 1 using compound 100 (1.00 g, 1.10 mmol), (piperidin-4-ylmethyl)-carbamic acid ethyl ester (506 mg, 2.71 mmol), and manganese(IV) oxide (1.20 g, 13.80 mmol) to provide compound 51 (35 mg, 3% yield) as a blue solid, Mp=175-185° C.; ESI (+) MS: 985 (M+H⁺); UV/Vis: $\lambda_{max}$=647.5 nm.

EXAMPLE 57

Synthesis of Compound No. 60 (see Table 1 for Structure)

The title compound was prepared by the general deacetylation procedure of Example 2 using compound 51 (117 mg, 0.11 mol) to provide compound 60 (54 mg, 48%) as a blue solid, Mp=190-195° C.; ESI (+) MS: 943 (M+H⁺); UV/Vis: $\lambda_{max}$=638.9 nm.

EXAMPLE 58

Synthesis of Compound No. 53 (see Table 1 for Structure)

The precursor amine used in the preparation of compound 53 was prepared as follows:

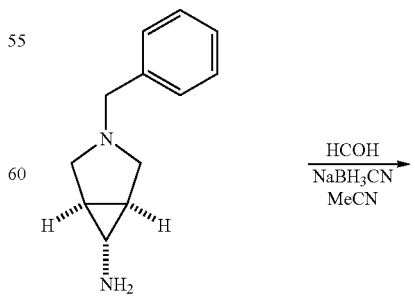

[101b]

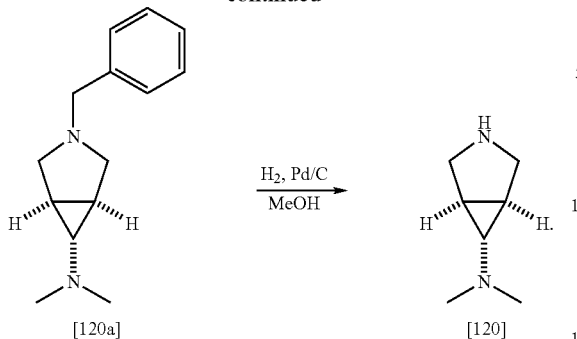

[120a]        [120]

Formaldehyde (21.5 mL, 37 wt. % solution in water, 276 mmol) followed by sodium cyanoborohydride (2.89 g, 46.0 mmol) was added to a stirred solution of compound 101b (1.73 g, 9.19 mmol) in acetonitrile (175 mL). The reaction was stirred under an atmosphere of $N_2$ at ambient temperature for 15 minutes at which time the pH was adjusted to neutral (pH paper) with acetic acid. The reaction was stirred under an atmosphere of $N_2$ at ambient temperature for 75 minutes (adjusting pH every 15 minutes if necessary), and the solvent was removed in vacuo. Aqueous NaOH (175 mL, 2M) was added, and the aqueous layer extracted with diethyl ether (×5). The organics were combined and dried over $Na_2SO_4$. Filtration followed by removal of the solvent in vacuo yielded a residue that was purified via flash chromatography (19:1 to 9:1, methylene chloride:methanol) to yield compound 120a (1.08 g, 57% yield) as a yellow oil, $^1$H NMR (CDCl$_3$, 300 MHz): 1.42-1.44 (m, 2H), 1.95-1.97 (m, 1H), 2.30 (s, 6H), 2.39 (d,j=8.5 Hz, 2H), 2.94 (d,j=8.8 Hz, 2H), 3.56 (s, 2H), 7.22-7.32 (m, 5H); ESI (+) MS: 217 (M+H$^+$).

A mixture of compound 120a (1.07 g, 4.95 mmol), Pd/C (300 mg, 10%, wet), and methanol (50 mL) was hydrogenated on a Parr apparatus at 50 psi $H_2$ 15 hours. The reaction was filtered through celite, and the solvent removed in vacuo. The resulting residue was dissolved in methanol (50 mL) to which was added Pd/C (600 mg, 10%, wet). The reaction was hydrogenated on a Parr apparatus at 55 psi $H_2$, at 50° C. for 20.5 hours. The reaction was filtered through celite, and the solvent removed in vacuo to yield compound 120 (528 mg, 84%) as a white solid. $^1$H NMR (CDCl$_3$, 500 MHz): 1.37 (t,j=2.0 Hz, 1H), 1.51 (q,j=2.0 Hz, 2H), 1.97 (bs, 1H), 2.29 (s, 6H), 2.90 (d,j=11.5 Hz, 2H), 3.00 (d,j=11.0 Hz, 2H). ESI (+) MS: 127 (M+H$^+$).

The title compound was prepared by the general coupling procedure of Example 1 using compound 100 (1.88 g, 2.05 mmol), amine 120 (518 mg, 4.10 mmol), and manganese (IV) oxide (1.78 g, 20.5 mmol) to provide compound 53 (1.24 g, 65% yield) as a blue solid, Mp=>370° C.; ESI (+) MS: 925 (M+H$^+$); UV/Vis: $\lambda_{max}$=642.4 nm.

EXAMPLE 59

Synthesis of Compound No. 54 (see Table 1 for Structure)

The title compound was prepared by the general deacetylation procedure of Example 2 using compound 53 (347 mg, 0.375 mmol) to provide compound 54 (289 mg, 87%) as a blue solid, Mp=>330° C.; ESI (+) MS: 883 (M+H$^+$); UV/Vis: $\lambda_{max}$=642.2 nm.

EXAMPLE 60

Synthesis of Compound No. 55 (see Table 1 for Structure)

The title compound was prepared by the general coupling procedure of Example 1 using compound 100 (1.00 g, 1.10 mmol), N-(piperidin-4-ylmethyl)-acetamide (452 mg, 2.89 mmol, U.S. Pat. No. 4,370,328), and manganese(IV) oxide (1.2 g, 13.80 mol) to provide compound 55 (215 mg, 20% yield) as a blue solid, Mp=214-218° C.; ESI (+) MS: 955 (M+H$^+$); UV/Vis: $\lambda_{max}$=647.5 nm.

EXAMPLE 61

Synthesis of Compound No. 56 (see Table 1 for Structure)

The title compound was prepared by the general deacetylation procedure of Example 2 using compound 55 (152 mg, 0.15 mol) to provide compound 56 (68 mg, 46% yield) as a blue solid, Mp=205-213° C.; ESI (+) MS: 913 (M+H$^+$); UV/Vis: $\lambda_{max}$=647.2 nm.

EXAMPLE 62

Synthesis of Compound No. 57 (see Table 1 for Structure)

The title compound was prepared by the general coupling procedure of Example 1 using compound 100 (2.70 g, 3.10 mmol), 4-phenylpiperidine (1.00 g, 6.20 mmol) and manganese(IV) oxide (2.70 g, 31.0 mmol) to provide compound 57 (1.97 g, 66% yield) as a blue solid, Mp=220-222° C.; ESI (+) MS: 960 (M+H$^+$); UV/Vis: $\lambda_{max}$=646.5 nm.

EXAMPLE 63

Synthesis of Compound No. 58 (see Table 1 for Structure)

The precursor amine used in the preparation of compound 58 was prepared as follows:

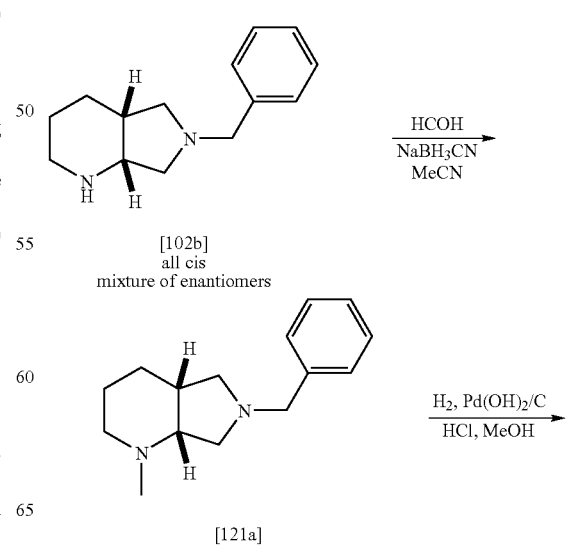

-continued

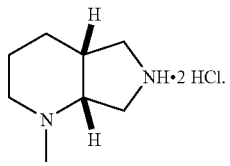

[121]

Formaldehyde (11.8 mL, 37 wt. % solution in water, 152 mmol) followed by sodium cyanoborohydride (1.59 g, 25.3 mmol) was added to a stirred solution of compound 102b (2.19 g, 10.1 mmol) in acetonitrile (100 mL). The reaction was stirred under an atmosphere of $N_2$ at ambient temperature for 15 minutes at which time the pH was adjusted to neutral (pH paper) with acetic acid. The reaction was stirred under an atmosphere of $N_2$ at ambient temperature for 4.5 hours, and the solvent was removed in vacuo. Aqueous NaOH (100 mL, 2M) was added, and extracted with diethyl ether (×5). The organics were combined and dried over $Na_2SO_4$. Filtration followed by removal of the solvent in vacuo yielded a residue that was purified via flash chromatography (9:1, methylene chloride:methanol) to yield compound 121a (1.95 g, 84% yield) as a yellow oil, $^1$H NMR (CDCl$_3$, 300 MHz): 1.47-1.84 (m, 4H), 2.04-2.13 (m, 1H), 2.19 (s, 3H), 2.23-2.33 (m, 1H), 2.57-2.66 (m, 3H), 2.72-2.81 (m, 2H), 2.95-3.01 (m, 1H), 3.75 (s, 2H), 7.22-7.38, (m, 5H); ESI (+) MS: 231 (M+H$^+$).

A mixture of compound 121a (1.94 g, 8.42 mmol), Pd/C (500 mg, 10%, wet), and methanol (50 mL, sparged with $H_2$) was stirred under balloon pressure $H_2$ for 12 hours. The reaction was filtered through celite, and the solvent removed in vacuo. The resulting residue was dissolved in methanol (50 mL) to which was added Pd/C (500 mg, 10%, wet). The reaction was hydrogenated on a Parr apparatus at 55 psi $H_2$, at 50° C. for 15.5 hours. The reaction was filtered through celite, and the solvent removed in vacuo. The resulting residue was dissolved in methanol (50 mL) to which was added Pd(OH)$_2$/C (500 mg, 20%, wet) and HCl (2 mL, conc.). The reaction was hydrogenated on a Parr apparatus at 50 psi $H_2$ for 10 hours. The reaction was filtered through celite, and the solvent removed in vacuo to yield compound 121 (1.70 g, 95% yield) as an off-white foam, $^1$H NMR (CD$_3$OD, 500 MHz): 1.86-2.01 (m, 4H), 2.86-2.92 (m, 5H), 3.04-3.12 (m, 1H), 3.51-3.65 (m, 3H), 3.78 (d,j=10.5 Hz, 1H), 3.91-3.94 (m, 2H). ESI (+) MS: 141 (M−2HCl+H$^+$).

The title compound was prepared by the general coupling procedure of Example 1 using compound 100 (6.68 g, 7.30 mmol), amine 121 (1.68 g, 7.88 mmol), triethylamine (3.30 mL, 23.6 mmol), and manganese(IV) oxide (3.43 g, 39.4 mmol) to provide compound 58 (1.57 g, 42% yield) as a blue solid after chromatography, Mp=>300° C.; ESI (+) MS: 939 (M+H$^+$); UV/Vis: $\lambda_{max}$=649.5 nm. The other diastereomers was also obtained.

EXAMPLE 64

Synthesis of Compound No. 59 (see Table 1 for Structure)

The title compound was prepared by the general deacetylation procedure of Example 2 using compound 58 (335 mg, 0.357 mmol) to provide compound 59 (278 mg, 87%) as a blue solid, Mp=>300° C.; ESI (+) MS: 897 (M+H$^+$); UV/Vis: $\lambda_{max}$=649.4 nm.

EXAMPLE 65

Synthesis of 25-O-deacetyl-25-(2",3"-dihydroxypropylcarbonoxy)-21,23-(1-methylethylidene acetal) rifamycin (Compound 122)

The title compound was prepared as follows:

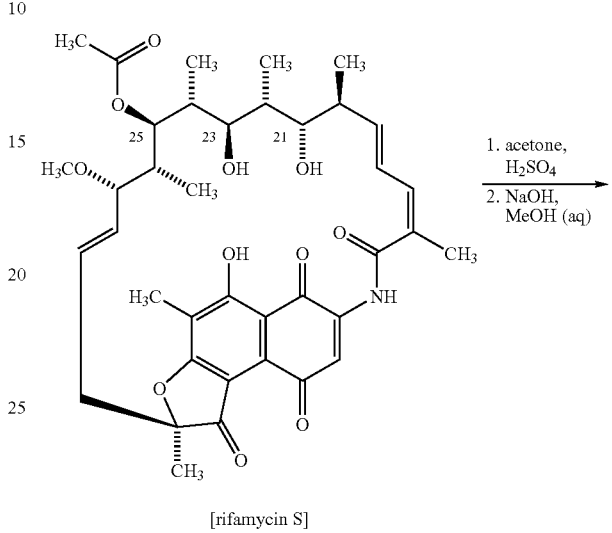

[rifamycin S]

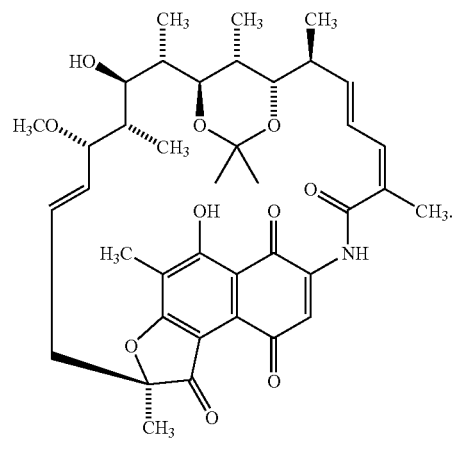

[122]

Following the procedure of Kump, et al., *Helv. Chim. Acta*. 56:2323 (1973), 5 microliters of concentrated sulfuric acid is added to a solution of rifamycin S (1.1 g), dimethoxypropane (1.1 mL), and dry acetone (12 mL). The reaction mixture is stirred 45 minutes at room temperature. Anhydrous sodium carbonate (1 g) is added and stirring continued for 5 min. The solution is filtered and evaporated to dryness. The residue is purified by flash-chromatography; elution with 1% methanol in dichloromethane affords rifamycin S, cyclic-21,23-(1-methylethylidene acetal), compound, which is dissolved in a cold solution of 5% NaOH in methanol (100 mL). The resulting mixture is stirred 18 hours at room temperature then diluted with icy water (100 mL), acidified (about pH 4) with citric acid and extracted with dichloromethane (3×100 mL). The combined extracts are dried and evaporated to dryness. The residue, by crystallization from ethyl ether/petroleum ether, gives compound 122, 25-O-deacetyl-rifamycin S, cyclic-21,23-(1-methylethylidene acetal).

In addition to its use in the synthesis of 25-(2",3"-dihydroxypropylcarbonoxy)oxybenzoxazinorifamycin analogs, as described below, compound 122 can also be used as a protected intermediate for the synthesis of other analogs in which the 25 position of rifamycin is derivatized. The conversion hydroxy groups to other moieties is well known to those skilled in the art.

EXAMPLE 66

Synthesis of 25-O-deacetyl-21,23-(1-methylethylidene acetal)-5'-[4-isobutyl-1-piperazinyl]benzoxazinorifamycin (Compound 123)

The title compound was prepared as follows:

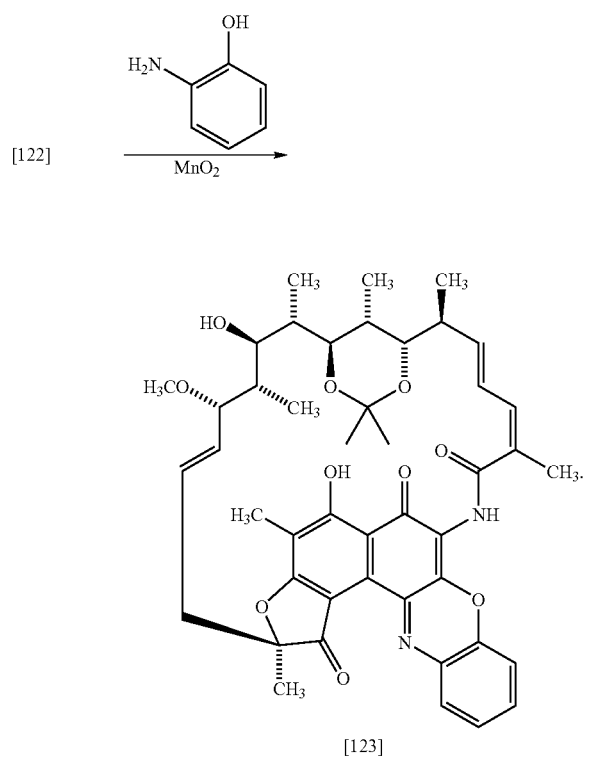

Compound 122 (0.30 g) and 2-hydroxyaniline (0.060 g) in 10 mL of toluene are stirred at room temperature for 12 days. After insoluble substances are filtered off, the solvent is removed under reduced pressure, and the residue dissolved in 7 mL of ethanol. To the solution is added 0.15 g of manganese dioxide and the mixture stirred at room temperature for 7 hours. Manganese dioxide is filtered off by using a filter aid and the solvent removed under reduced pressure. The residue is purified by silica-gel column-chromatography [eluent: chloroform-methanol (99:1)] to give the title compound (compound 123)

EXAMPLE 67

Synthesis of 25-O-deacetyl-25-(2",3"-dihydroxypropylcarbonoxy)-21,23-(1-methylethylidene acetal)-5'-[4-isobutyl-1-piperazinyl]benzoxazinorifamycin (Compound 124)

The title compound was prepared as follows:

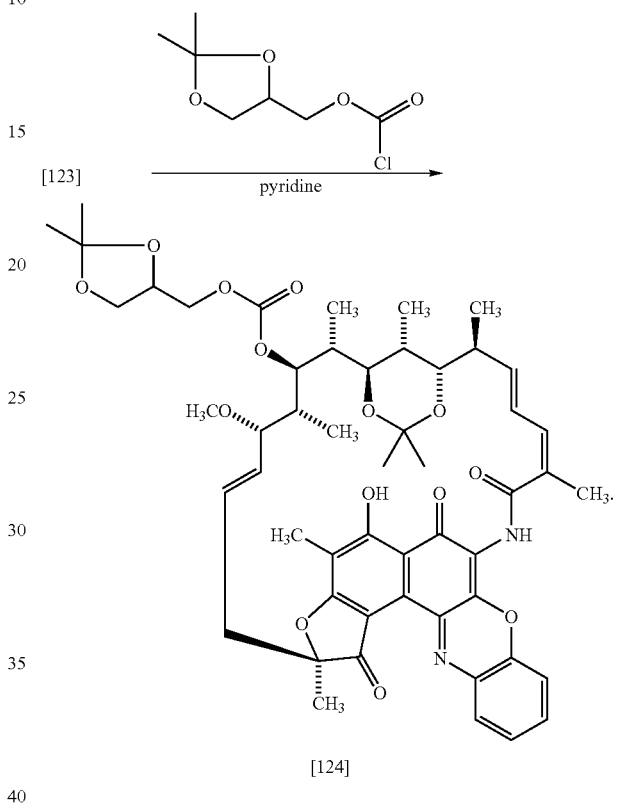

Compound 123 (0.20 g) and 1-O-chloroformyl-2,3-O-isopropylidene-D,L-glycerol (0.90 g, see Seligson, et al., *Anticancer Drugs* 12: 305-13,2001) are dissolved in dry $CH_2Cl_2$ (4 mL) and cooled to −70° C. under argon. Pyridine (0.28 mL) is added, the cold bath removed, and the reaction stirred at room temperature for 4.5 hours. The organics are washed with water and dried over magnesium sulfate. After filtration and concentration under reduced pressure, the resulting solution is purified by silica gel chromatography ($CH_2Cl_2$/acetone) to yield compound 124.

EXAMPLE 68

Synthesis of 25-O-deacetyl-25-(2",3"-dihydroxypropylcarbonoxy)-5'-[4-isobutyl-1-piperazinyl]benzoxazinorifamycin, (Compound 126)

The title compound was prepared as follows:

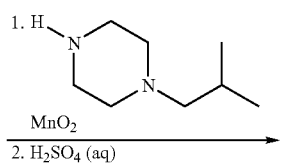

-continued

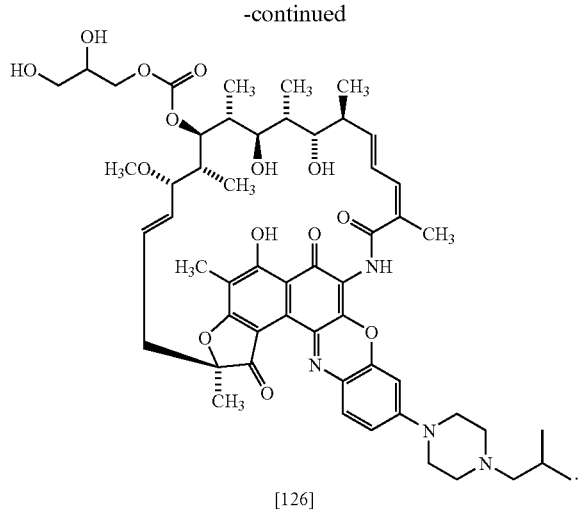

[126]

The general coupling procedure of Example 1 is used to prepare the title compound. To compound 124 (0.20 g) in 3 mL of dimethyl sulfoxide is added 100 mg of 4-isobutylpiperazine and 0.2 g of manganese dioxide. The mixture stirred at room temperature for 5 days. The reaction mixture is diluted by addition of ethyl acetate and insoluble substances are filtered off. The filtrate is washed successively with water and with a saturated aqueous solution of sodium chloride, and dried over anhydrous sodium sulfate. After the drying agent is filtered off, the solvent is removed under reduced pressure. The residue is purified twice by silica-gel column-chromatography [eluent: ethyl acetate/hexane, 1:1 to 9:1 gradient] to give 25-O-deacetyl-25-(2″,3″-dihydroxypropylcarbonoxy)-21,23-(1-methylethylidene acetal)-5'-[4-isobutyl-1-piperazinyl]benzoxazinorifamycin (compound 125).

Compound 125 is dissolved in THF (2 mL) and 3% (v/v) sulfuric acid/water (0.7 mL) is added. The reaction mixture is stirred for 16 hours at 40° C. After cooling, the reaction mixture is diluted with water (5 mL) and extracted with ethyl acetate (2×10 mL). The combined organics are dried over magnesium sulfate, filtered, and the volatiles removed under reduced pressure to give 25-O-deacetyl-25-(2″,3″-dihydroxypropylcarbonoxy)-5'-[4-isobutyl-1-piperazinyl]benzoxazinorifamycin, compound 126.

EXAMPLE 69

MIC Assay

MICs of candidate compounds of the invention can be determined, for example, by the method of Lee et al., Am. Rev. Respir. Dis. 136:349 (1987). To a BACTEC 12B vial (4 mL of 7H12B medium), 0.1 mL of a 10-fold dilution of subculture of the test organisms in 7H9 medium (optical density at 540 nm, 0.1) is inoculated and cultured at 37° C. until a growth index (GI) of 999 is reached. Then the broth culture is removed and diluted 100-fold, and 0.1 mL of the dilution is inoculated into a BACTEC 12B vial with or without a candidate compound. The candidate compound containing vials can hold 0.1 mL of candidate compound solution appropriately diluted to obtain the desired concentration. A 1% control vial, 0.1 mL of the 100-fold dilution of the inoculum described above, is inoculated into 12B vial without candidate compound. The 12B vials are incubated at 37° C., and GI readings recorded daily, using a BACTEC 460 TB instrument (Johnston Laboratories, Townsend, Md.), until the control vial reaches a GI greater than 30. When the final readings in the GI of the candidate containing vials are lower than those of the 1% control, the drug is considered to have inhibited more than 99% of the bacterial population, and this concentration will be defined as the MIC.

Table 1 gives MIC values for some of the compounds of the invention.

TABLE 1

Structures and MIC values

| Compound No. | Structure* | MW | MP (° C.) | MIC (µg/mL) S. aureus | S. pneumo. | E. faecalis | H. flu | E. coli |
|---|---|---|---|---|---|---|---|---|
| 1 | 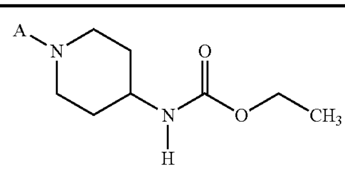 | 971.06 | 226-230 | 0.008 | 0.00025 | 2 | 2 | >8 |
| 2 | 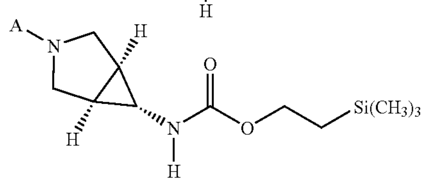 | 1041.23 | 230-231 | 1 | 0.03 | >8 | >8 | >8 |
| 3 | 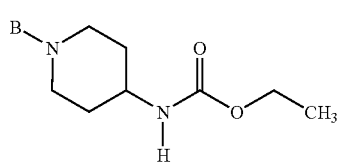 | 929.027 | 206-216 | 0.03 | 0.0005 | 0.12 | 0.25 | 4 |

TABLE 1-continued

Structures and MIC values

| Compound No. | Structure* | MW | MP (° C.) | MIC (µg/mL) ||||||
| | | | | S. aureus | S. pneumo. | E. faecalis | H. flu | E. coli |
| --- | --- | --- | --- | --- | --- | --- | --- | --- |
| 4 | | 896.985 | >300 | 0.03 | 0.00025 | 0.5 | 0.25 | >8 |
| 5 | | 925.039 | >300 | 0.015 | 0.00025 | 0.5 | 2 | 8 |
| 6 | | 1031.16 | 224-228 | 0.015 | 0.00025 | 0.25 | 1 | 4 |
| 7 | | 883.002 | 240-243 | 0.12 | 0.004 | 4 | 4 | >8 |
| 8 | | 989.126 | 214-216 | 0.008 | 0.001 | 0.12 | 0.5 | 8 |
| 9 | | 969.092 | 228-230 | 0.015 | 0.001 | 2 | 2 | 8 |
| 10 | | 911.012 | 210-212 | 0.008 | 0.00012 | 1 | 2 | >8 |
| 11 | | 927.055 | 222-224 | 0.004 | 0.00012 | 0.25 | 1 | 4 |

TABLE 1-continued

Structures and MIC values

| Compound No. | Structure* | MW | MP (° C.) | MIC (µg/mL) | | | | |
|---|---|---|---|---|---|---|---|---|
| | | | | S. aureus | S. pneumo. | E. faecalis | H. flu | E. coli |
| 12 | 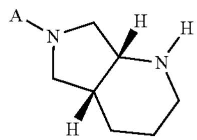 | 925.039 | >320 | 0.004 | 0.00025 | 0.12 | 0.25 | 8 |
| 13 | 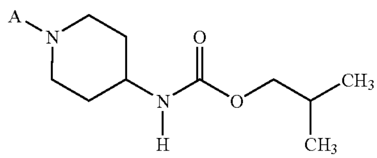 | 999.117 | 184-188 | 0.008 | 0.00012 | 0.5 | 2 | 4 |
| 14 | 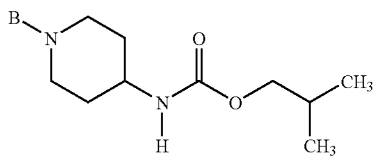 | 957.081 | 173-180 | | | | | |
| 15 | 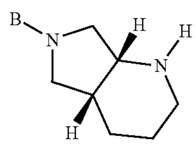 | 883.002 | 216-227 | 0.03 | 0.002 | 0.25 | 1 | >8 |
| 16 | 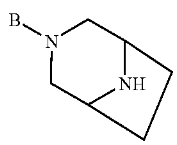 | 868.975 | 208-229 | 0.015 | 0.001 | 0.12 | 0.25 | 4 |
| 17 | 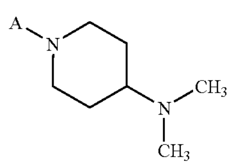 | 927.055 | >400 | 0.008 | 0.00012 | 1 | 1 | 8 |
| 18 | 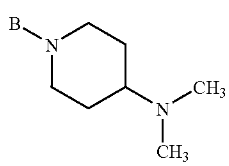 | 885.018 | 214-216 | 0.004 | 0.00012 | 0.12 | 0.5 | 4 |
| 19 | 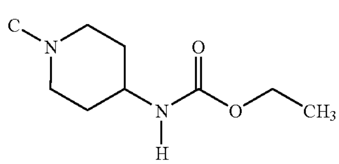 | 968.107 | 220-240 | 0.004 | 0.001 | 0.06 | 0.25 | 4 |
| 20 | 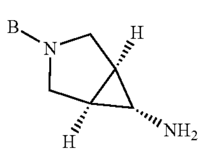 | 854.949 | 211-231 | 2 | 1 | >8 | >8 | >8 |

TABLE 1-continued

Structures and MIC values

| Compound No. | Structure* | MW | MP (° C.) | MIC (μg/mL) | | | | |
|---|---|---|---|---|---|---|---|---|
| | | | | S. aureus | S. pneumo. | E. faecalis | H. flu | E. coli |
| 21 | 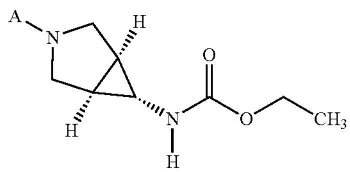 | 969.048 | >350 | 0.004 | 0.001 | 0.12 | 0.5 | 4 |
| 22 | 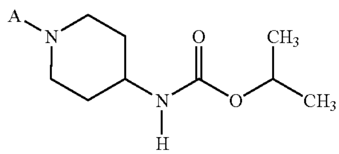 | 985.091 | >300 | 0.015 | 0.00025 | 4 | 2 | >8 |
| 23 | 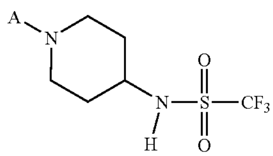 | 1031.06 | 238-240 | 0.015 | 0.00012 | 4 | 2 | >8 |
| 24 | 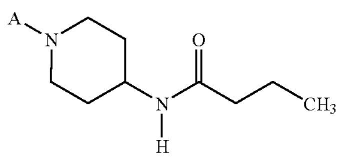 | 969.092 | 222-226 | 0.015 | 0.001 | 2 | 2 | >8 |
| 25 | 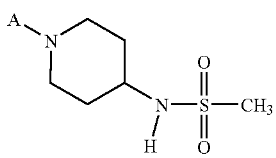 | 977.092 | 256-257 | 0.008 | 0.001 | 2 | 2 | >8 |
| 26 | 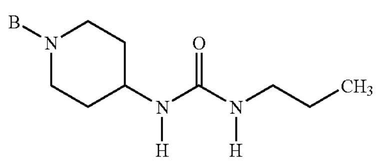 | 942.07 | 265-266 | 0.008 | 0.00012 | 2 | 1 | >8 |
| 27 | 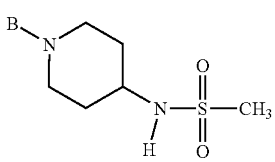 | 935.055 | 270-273 | 0.015 | 0.001 | 1 | 0.12 | >8 |
| 28 | 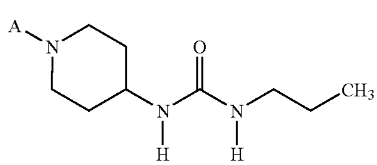 | 984.107 | 260-263 | 0.03 | 0.002 | 1 | 0.25 | >8 |
| 29 | 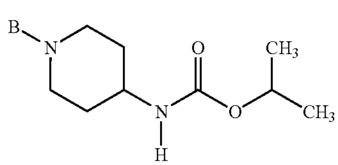 | 943.054 | 222-225 | 0.008 | 0.00012 | 2 | 1 | >8 |

TABLE 1-continued

Structures and MIC values

| Compound No. | Structure* | MW | MP (° C.) | MIC (µg/mL) | | | | |
|---|---|---|---|---|---|---|---|---|
| | | | | S. aureus | S. pneumo. | E. faecalis | H. flu | E. coli |
| 30 | B-N-piperidine-NH-C(O)-O-CH₃ | 915 | 212-225 | 0.015 | 0.002 | 1 | 0.5 | >8 |
| 31 | D-N-piperidine-NH-C(O)-O-CH₂CH₃ | 926.071 | 250-252 | 0.03 | 0.0005 | 0.25 | 0.25 | 8 |
| 32 | A-N-piperidine-NH-C(O)-O-CH₃ | 957.037 | 149-153 | 2 | 4 | >8 | >8 | >8 |
| 33 | A-N-piperidine-NH₂ | 899.001 | 278-279 | 0.008 | 0.00006 | 1 | 1 | >8 |
| 34 | A-N-piperidine-NH-C(O)-NH-CH₂CH₃ | 970.08 | 234-236 | 0.03 | 0.001 | 2 | 0.5 | 8 |
| 35 | A-N-piperidine-NH-SO₂-CH₂CH₂CH₃ | 1005.15 | 220-226 | 0.015 | 0.00025 | 4 | 0.5 | 8 |
| 36 | B-N-piperidine-NH-C(O)-CH₂CH₂CH₃ | 927.055 | 228-230 | 0.004 | 0.00003 | 2 | 0.25 | >8 |
| 37 | B-N-piperidine-NH-C(O)-NH-CH₂CH₃ | 928.043 | 321-322 | 0.03 | 0.004 | 2 | 0.25 | >8 |
| 38 | B-N-piperidine-NH-SO₂-CF₃ | 989.026 | 245-246 | 0.12 | 0.015 | 8 | 0.25 | >8 |

TABLE 1-continued

Structures and MIC values

| Compound No. | Structure* | MW | MP (° C.) | MIC (µg/mL) | | | | |
|---|---|---|---|---|---|---|---|---|
| | | | | S. aureus | S. pneumo. | E. faecalis | H. flu | E. coli |
| 39 | 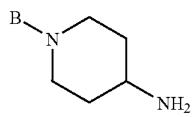 | 856.964 | 265-266 | 0.03 | 0.001 | 2 | 0.25 | >8 |
| 40 | 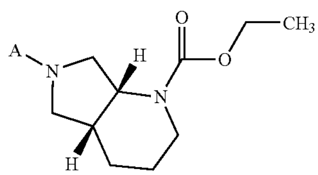 | 997.102 | >300 | 0.06 | 0.008 | 1 | 0.5 | >8 |
| 41 | 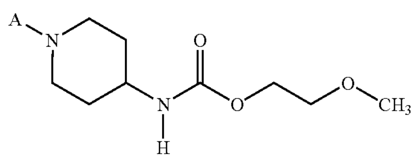 | 1001.09 | 175-183 | 0.25 | 0.0005 | >8 | 2 | >8 |
| 42 | 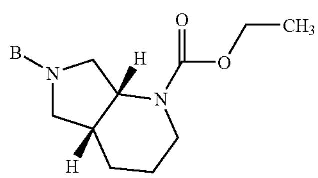 | 955.065 | >300 | 0.008 | 0.00012 | 2 | 0.5 | 8 |
| 43 | 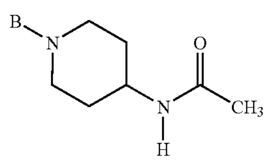 | 899.001 | 232-236 | 0.03 | 0.002 | 2 | 0.5 | >8 |
| 44 | 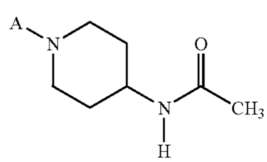 | 941.038 | 232-234 | 0.06 | 0.008 | 2 | 0.25 | >8 |
| 45 | 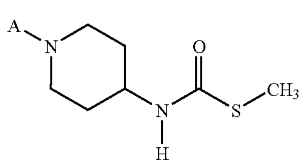 | 973.104 | 150-155 | 0.015 | 0.001 | 4 | 0.5 | 8 |
| 46 | 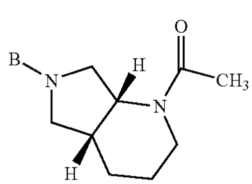 | 925.039 | 148-150 | 0.004 | 0.00006 | 2 | 0.5 | >8 |
| 47 | 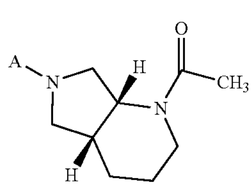 | 967.076 | 148-149 | 0.008 | 0.002 | 1 | 0.25 | >8 |

TABLE 1-continued

Structures and MIC values

| Compound No. | Structure* | MW | MP (° C.) | MIC (µg/mL) | | | | |
| --- | --- | --- | --- | --- | --- | --- | --- | --- |
| | | | | S. aureus | S. pneumo. | E. faecalis | H. flu | E. coli |
| 48 | 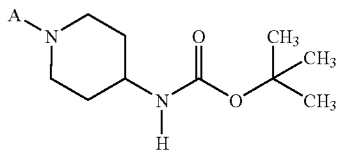 | 999.117 | 218-228 | 0.008 | 0.00025 | 2 | 1 | >8 |
| 49 | 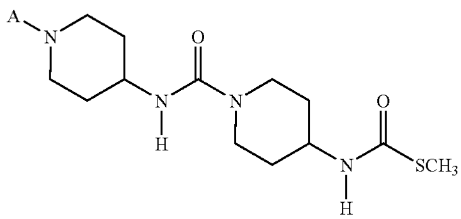 | 1099.2 | >300 | 0.06 | 0.0005 | 8 | 2 | >8 |
| 50 | 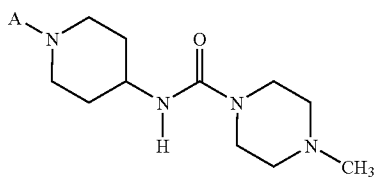 | 1025.16 | >300 | 0.03 | 0.00012 | 4 | 0.5 | >8 |
| 51 | 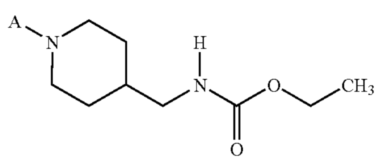 | 985.091 | 175-185 | 0.06 | 0.002 | 8 | 0.25 | 8 |
| 52 | 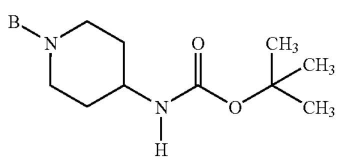 | 957.081 | 230-232 | 0.015 | 0.00025 | 4 | 0.12 | >8 |
| 53 | 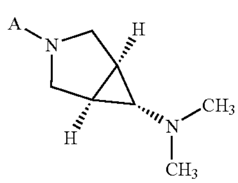 | 925.039 | >370 | 0.06 | 0.008 | 4 | 2 | >8 |
| 54 | 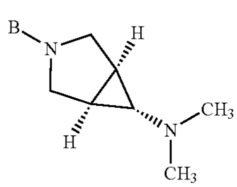 | 883.002 | >330 | 0.008 | 0.0005 | 2 | 0.25 | >8 |
| 55 | 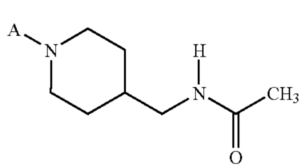 | 955.065 | 214-218 | 0.008 | 0.00025 | 1 | 0.5 | 8 |

TABLE 1-continued

Structures and MIC values

| Compound No. | Structure* | MW | MP (° C.) | MIC (µg/mL) | | | | |
|---|---|---|---|---|---|---|---|---|
| | | | | S. aureus | S. pneumo. | E. faecalis | H. flu | E. coli |
| 56 | B-N-piperidine-CH2-NH-C(=O)-CH3 | 913.028 | 205-213 | 0.004 | 0.001 | 0.12 | 0.25 | 8 |
| 57 | A-N-piperidine-phenyl | 960.084 | 220-222 | 0.008 | 0.0005 | 2 | 0.5 | 8 |
| 58 | A-N-octahydropyrrolopyridine-CH3 | 939.066 | >300 | 0.03 | 0.004 | 1 | 0.25 | >8 |
| 59 | B-N-octahydropyrrolopyridine-CH3 | 897.029 | >300 | 0.004 | 0.001 | 0.06 | 0.12 | 4 |
| 60 | B-N-piperidine-CH2-NH-C(=O)-O-CH2CH3 | 943.054 | 110-195 | 0.008 | 0.0005 | 0.5 | 0.06 | >8 |
| 61 | A-N-piperidine-CH2CH2-OH | 928.039 | 205-212 | 0.004 | 0.00012 | 1 | 0.25 | >8 |
| 62 | B-N-piperidine-phenyl | 918.047 | 228-230 | 0.015 | 0.008 | 8 | 0.5 | >8 |
| 63 | B-N-piperidine-NH-C(=O)-O-CH2CH2-O-CH3 | 959.053 | 210-214 | 0.008 | 0.002 | 1 | 0.25 | 8 |
| 64 | E-N-dimethylpiperazine | 913.096 | >250 | 0.004 | 0.00012 | 0.12 | 0.25 | 4 |

TABLE 1-continued

Structures and MIC values

| Compound No. | Structure* | MW | MP (° C.) | MIC (µg/mL) ||||| 
|---|---|---|---|---|---|---|---|---|
| | | | | S. aureus | S. pneumo. | E. faecalis | H. flu | E. coli |
| 65 | (structure) | 871.059 | >300 | 0.002 | 0.00025 | 0.12 | 0.12 | 2 |
| 66 | (structure) | 886.002 | 115-122 | 0.004 | 0.0005 | 0.12 | 0.12 | 4 |
| 67 | (structure) | 963.109 | | 0.008 | 0.001 | 0.5 | 0.12 | >8 |
| 68 | (structure) | 967.187 | >250 | 0.06 | 0.0005 | 2 | 0.5 | >8 |
| 69 | (structure) | 927.123 | >250 | 0.015 | 0.00025 | 0.5 | 0.5 | 4 |
| 70 | (structure) | 925.151 | >250 | 0.03 | 0.001 | 1 | 1 | >8 |
| 71 | (structure) | 941.082 | 216-220 | 0.008 | 0.00012 | 0.25 | 0.5 | 4 |
| 72 | (structure) | 955.065 | 210-214 | 0.008 | 0.00025 | 2 | 0.5 | >8 |

TABLE 1-continued
Structures and MIC values
| Compound No. | Structure* | MW | MP (° C.) | MIC (μg/mL) S. aureus | S. pneumo. | E. faecalis | H. flu | E. coli |
|---|---|---|---|---|---|---|---|---|
| 73 | B–N(piperidine)-C(CH₃)-N(CH₃)₂ | 899.045 | 215-218 | 0.002 | 0.00025 | 0.03 | 0.12 | 2 |
| 74 | B–N(piperidine)-C(CH₃)-NH-C(O)CH₃ | 913.028 | 220-221 | 0.03 | 0.001 | 0.5 | 0.12 | >8 |
| 75 | A–N(pyrrolidine)-N(CH₃)₂ | 913.028 |  | 0.002 | 0.00012 | 0.12 | 0.25 | 4 |
| 76 | E–N(octahydropyrrolopyrazine) | 925.107 | >250 | 0.008 | 0.00025 | 0.5 | 0.25 | 4 |
| 77 | F–N(octahydropyrrolopyrazine) | 883.07 | >250 | 0.002 | 0.00025 | 0.25 | 0.12 | 2 |
| 78 | A–N(azetidine)-OH | 875.99 |  | 0.002 | 0.00012 | 0.12 | 0.12 | 4 |
| 79 | B–N(azetidine)-OH | 833.95 |  |  |  |  |  |  |
*A, B, C, D, E, and F represent the following moieties:
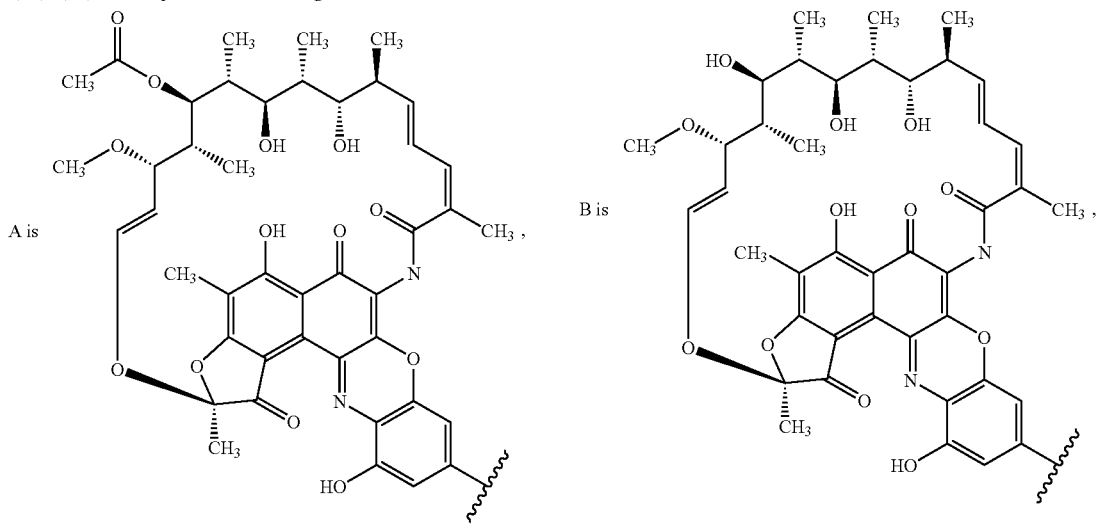

TABLE 1-continued

Structures and MIC values

| Com-pound No. | Structure* | MW | MP (° C.) | MIC (μg/mL) | | | | |
|---|---|---|---|---|---|---|---|---|
| | | | | S. aureus | S. pneumo. | E. faecalis | H. flu | E. coli |

C is [structure], D is [structure], E is [structure], and F is [structure]

Other Embodiments

All publications and patents cited in this specification are herein incorporated by reference as if each individual publication or patent were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

While the invention has been described in connection with specific embodiments, it will be understood that it is capable of further modifications. Therefore, this application is intended to cover any variations, uses, or adaptations of the invention that follow, in general, the principles of the invention, including departures from the present disclosure that come within known or customary practice within the art. Other embodiments are within the claims.

What is claimed is:
1. A compound having the Formula (I):

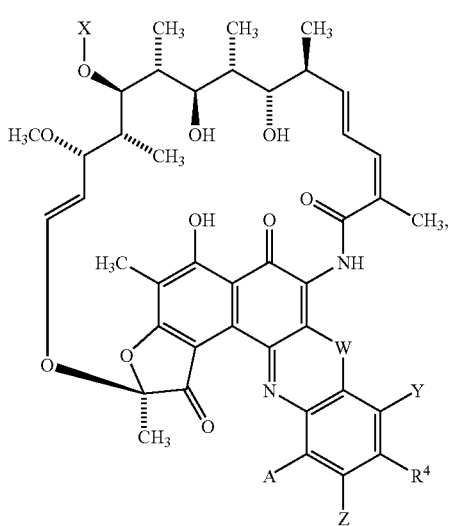

or a pharmaceutically acceptable salt thereof, wherein
A is H, OH, O—($C_1$-$C_6$ alkyl), or O—($C_1$-$C_4$ alkaryl);
W is O, S, or $NR^1$, wherein $R^1$ is H or $C_1$-$C_6$ alkyl;
X is H or $COR^2$, wherein $R^2$ is $C_1$-$C_6$ alkyl, which can be substituted with from 1 to 5 hydroxyl groups, or O—($C_3$-$C_7$ alkyl), which can be substituted with from 1 to 4 hydroxyl groups, wherein each alkyl carbon is bound to no more than one oxygen;
Y is H, $OR^3$, or Hal;
Z is H, $OR^3$, or Hal;
$R^3$ is $C_1$-$C_6$ alkyl; and
$R^4$ has the formula:

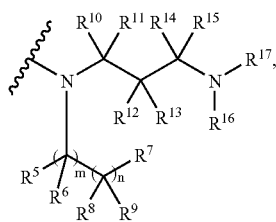

wherein,
each of m and n is independently an integer selected from 0 and 1, wherein,
when each of m and n is 1,
each of $R^5$ and $R^6$ is H, or $R^5$ and $R^6$ together are =O;
$R^7$ and $R^{10}$ together form a single bond or a $C_1$-$C_3$ linkage, which optionally contains a non-vicinal O, S, or $N(R^{23})$, $R^7$ and $R^{12}$ together form a single bond or a $C_1$-$C_2$ linkage, which optionally contains a non-vicinal O, S, or $N(R^{23})$, or $R^7$ and $R^{14}$ together form a single bond or a $C_1$ linkage, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, or $C_1$-$C_4$ alkaryl, $R^8$ is H, $C_1$-$C_6$ alkyl, or $C_1$-$C_4$ alkaryl, or $R^8$ and $R^{12}$ together form a single bond, or $R^8$ and $R^9$ together are =N—O $R^{18}$, wherein $R^{18}$ is H, $C_1$-$C_6$ alkyl, or $C_1$-$C_4$ alkaryl;
$R^9$ is H, $C_1$-$C_6$ alkyl, or $C_1$-$C_4$ alkaryl, or $R^9$ and $R^8$ together are =N—$OR^{18}$;
$R^{10}$ is H, $C_1$-$C_6$ alkyl, or $C_1$-$C_4$ alkaryl, or $R^{10}$ and $R^7$ together form a single bond or a $C_1$-$C_3$ linkage, which optionally contains a non-vicinal O, S, or $N(R^{23})$, or $R^{10}$ and $R^{16}$ together form a $C_1$-$C_2$ alkyl linkage, which optionally contains a non-vicinal O, S, or $N(R^{23})$, or $R^{10}$ and $R^{17}$ together form a $C_1$-$C_3$ alkyl linkage, which optionally contains a non-vicinal O, S, or $N(R^{23})$, or $R^{10}$ and $R^{11}$ together are =O, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, or $C_1$-$C_4$ alkaryl;
$R^{11}$ is H, or $R^{11}$ and $R^{10}$ together are =O;
$R^{12}$ is H, $C_1$-$C_6$ alkyl, or $C_1$-$C_4$ alkaryl, or $R^{12}$ and $R^7$together form a single bond or a $C_1$-$C_2$ linkage, which optionally contains a non-vicinal O, S, or $N(R^{23})$, or $R^{12}$ and $R^8$ together form a single bond, or $R^{12}$ and $R^{16}$ together form a $C_2$-$C_4$ alkyl linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, $C_1$-$C_4$ alkaryl;
each of $R^{13}$ and $R^{15}$ is H, $C_1$-$C_6$ alkyl, or $C_1$-$C_4$ alkaryl;
$R^{14}$ is H, $C_1$-$C_6$ alkyl, or $C_1$-$C_4$ alkaryl, or $R^{14}$ and $R^7$ together form a single bond or a $C_1$ linkage;
$R^{16}$ is H, $C_1$-$C_6$ alkyl, $C_1$-$C_6$ alkoxy, $C_6$-$C_{12}$ aryl, or $C_1$-$C_4$ alkaryl, or $R^{16}$ and $R^{12}$ together form a $C_2$-$C_4$ alkyl linkage, which optionally contains a non-vicinal O, S, or $N(R^{23})$, or $R^{16}$ and $R^{10}$ together form a $C_1$-$C_2$ alkyl linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, or $C_1$-$C_4$ alkaryl; and
$R^{17}$ is H, $C_1$-$C_6$ alkyl, $COR^{19}$, $CO_2R^{19}$, or $CONHR^{19}$, $CSR^{19}$, $COSR^{19}$, $CSOR^{19}$, $CSNHR^{19}$, $SO_2R^{19}$, or $SO_2NHR^{19}$, wherein $R^{19}$ is $C_1$-$C_6$ alkyl, $C_6$-$C_{12}$ aryl, or $C_1$-$C_4$ alkaryl, or $R^{17}$ and $R^{10}$ together form a $C_1$-$C_3$ alkyl linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, or $C_1$-$C_4$ alkaryl;
or
when m is 0 and n is 1,
$R^7$ and $R^{10}$ together form a single bond or a $C_1$-$C_4$ linkage, which optionally contains a non-vicinal O, S, or $N(R^{23})$, $R^7$ and $R^{12}$ together form a single bond or a $C_1$-$C_3$ linkage, which optionally contains a non-vicinal O, S, or $N(R^{23})$, or $R^7$ and $R^{14}$ together form a single bond or a $C_1$-$C_2$ linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, $CSNHR^{24}$, $SO_2R^{24}$, or $SO_2NHR^{24}$, wherein $R^{24}$ is $C_1$-$C_6$ alkyl, $C_6$-$C_{12}$ aryl, or $C_1$-$C_4$ alkaryl;
each of $R^8$, $R^9$, and $R^{11}$ is H;
$R^{15}$ is H, $C_1$-$C_6$ alkyl, or $C_1$-$C_4$ alkaryl;
$R^{10}$ is H or $R^{10}$ and $R^7$ together form a single bond or a $C_1$-$C_4$ linkage, which optionally contains a non-vicinal O, S, or $N(R^{23})$, wherein $R^{23}$ is H, $C_1$-$C_6$ alkyl, $COR^{24}$, $CO_2R^{24}$, or $CONHR^{24}$, $CSR^{24}$, $COSR^{24}$, $CSOR^{24}$, CSNHR$^{24}$, SO$_2$R$^{24}$, or SO$_2$NHR$^{24}$, wherein R$^{24}$ is C$_1$-C$_6$ alkyl, C$_6$-C$_{12}$ aryl, or C$_1$-C$_4$ alkaryl;

R$^{12}$ is H, C$_1$-C$_6$ alkyl, or C$_1$-C$_4$ alkaryl, or R$^{12}$ and R$^7$ together form a single bond or a C$_1$-C$_3$ linkage, which optionally contains a non-vicinal O, S, or N(R$^{23}$), R$^{12}$ and R$^{13}$ together form a —CH$_2$CH$_2$— linkage, or R$^{12}$ and R$^{16}$ together form a C$_2$-C$_4$ alkyl linkage, which optionally contains a non-vicinal O, S, or N(R$^{23}$), wherein R$^{23}$ is H, C$_1$-C$_6$ alkyl, COR$^{24}$, CO$_2$R$^{24}$, or CONHR$^{24}$, CSR$^{24}$, COSR$^{24}$, CSOR$^{24}$, CSNHR$^{24}$, SO$_2$R$^{24}$, or SO$_2$NHR$^{24}$, wherein R$^{24}$ is C$_1$-C$_6$ alkyl, C$_6$-C$_{12}$ aryl, or C$_1$-C$_4$ alkaryl;

R$^{13}$ is H, C$_1$-C$_6$ alkyl, C$_1$-C$_4$ alkaryl, or R$^{13}$ and R$^{12}$ together form a
—CH$_2$CH$_2$— linkage;

R$^{14}$ is H, C$_1$-C$_6$ alkyl, or C$_1$-C$_4$ alkaryl, or R$^{14}$ and R$^7$ together form a single bond or a C$_1$-C$_2$ linkage, which optionally contains a non-vicinal O, S, or N(R$^{23}$), wherein R$^{23}$ is H, C$_1$-C$_6$ alkyl, COR$^{24}$, CO$_2$R$^{24}$, or CONHR$^{24}$, CSR$^{24}$, COSR$^{24}$, CSOR$^{24}$, CSNHR$^{24}$, SO$_2$R$^{24}$, or SO$_2$NHR$^{24}$, wherein R$^{24}$ is C$_1$-C$_6$ alkyl, C$_6$-C$_{12}$ aryl, C$_1$-C$_4$ alkaryl;

R$^{16}$ is H, C$_1$-C$_6$ alkyl, C$_1$-C$_6$ alkoxy, C$_6$-C$_{12}$ aryl, or C$_1$-C$_4$ alkaryl; together form a C$_2$-C$_4$ alkyl linkage, which optionally contains a non-vicinal O, S, or N(R$^{23}$), wherein R$^{23}$ is H, C$_1$-C$_6$ alkyl, COR$^{24}$, CO$_2$R$^{24}$, or CONHR$^{24}$, CSR$^{24}$, COSR$^{24}$, CSOR$^{24}$, CSNHR$^{24}$, SO$_2$R$^{24}$, SO$_2$NHR$^{24}$, wherein R$^{24}$ is C$_1$-C$_6$ alkyl, C$_6$-C$_{12}$ aryl, or C$_1$-C$_4$ alkaryl; and R$^{17}$ is H, C$_1$-C$_6$ alkyl, COR$^{19}$, CO$_2$R$^{19}$, or CONHR$^{19}$, CSR$^{19}$, COSR$^{19}$, CSOR$^{19}$, CSNHR$^{19}$, SO$_2$R$^{19}$, or SO$_2$NHR$^{19}$, wherein R$^{19}$ is C$_1$-C$_6$ alkyl, C$_6$-C$_{12}$ aryl, or C$_1$-C$_4$ alkaryl;

or

A is OH;

X is H;

W, Y, and Z are defined as above; and

R$^4$ is selected from the group consisting of:

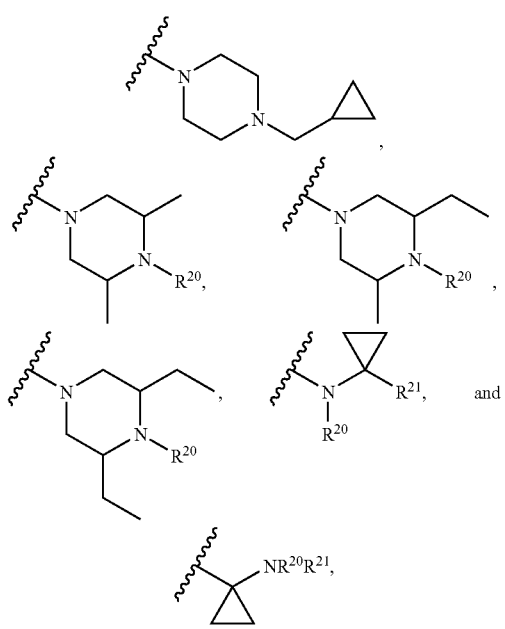

wherein R$^{21}$ is H, C$_1$-C$_6$ alkyl, C$_6$-C$_{12}$ aryl, or C$_1$-C$_4$ alkaryl, R$^{20}$ is H, C$_1$-C$_6$ alkyl, COR$^{19}$, CO$_2$R$^{19}$, or CONHR$^{19}$, CSR$^{19}$, COSR$^{19}$, CSOR$^{19}$, CSNHR$^{19}$, SO$_2$R$^{19}$, or SO$_2$NHR$^{19}$, wherein R$^{19}$ is C$_1$-C$_6$ alkyl, C$_6$-C$_{12}$ aryl, or C$_1$-C$_4$ alkaryl;

or

A is OH;

X is COCH$_3$;

W, Y, and Z are defined as above; and

R$^4$ is selected from the group consisting of:

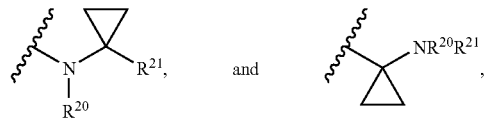

wherein R$^{21}$ is H, C$_1$-C$_6$ alkyl, C$_6$-C$_{12}$ aryl, or C$_1$-C$_4$ alkaryl, R$^{20}$ is H, C$_1$-C$_6$ alkyl, COR$^{19}$, CO$_2$R$^{19}$, or CONHR$^{19}$, CSR$^{19}$, COSR$^{19}$, CSOR$^{19}$, CSNHR$^{19}$, SO$_2$R$^{19}$, or SO$_2$NHR$^{19}$, wherein R$^{19}$ is C$_1$-C$_6$ alkyl, C$_6$-C$_{12}$ aryl, or C$_1$-C$_4$ alkaryl;

or

A is H or OH;

X is H or COCH$_3$;

W, Y, and Z are defined as above; and

R$^4$ is

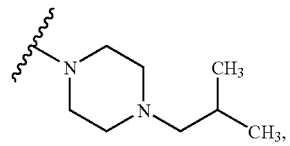

with the proviso that one or both of Y and Z are Hal;

or

A is H or OH;

X is H or COCH$_3$;

W, Y, and Z are defined as above; and

R$^4$ is

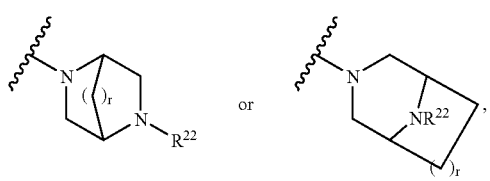

wherein R$^{22}$ is H, C$_1$-C$_6$ alkyl, C$_6$-C$_{12}$ aryl, C$_1$-C$_4$ alkaryl, COR$^{24}$, CO$_2$R$^{24}$, CONHR$^{24}$, CSR$^{24}$, COSR$^{24}$, CSOR$^{24}$, CSNHR$^{24}$, SO$_2$R$^{24}$, or SO$_2$NHR$^{24}$, wherein R$^{24}$ is C$_1$-C$_6$ alkyl, C$_6$-C$_{12}$ aryl, or C$_1$-C$_4$ alkaryl, and r is 1-2;

or

A is H or OH;

X is H or COCH$_3$;

W, Y, and Z are defined as above; and $R^4$ is

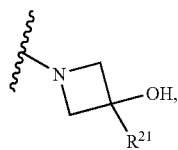

wherein $R^{21}$ is H, $C_1$-$C_6$ alkyl, $C_6$-$C_{12}$ aryl, or $C_1$-$C_4$ alkaryl;
or A is H or OH;
X is H or $COCH_3$;
W, Y, and Z are defined as above; and
$R^4$ is

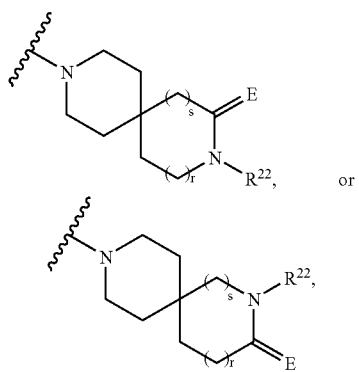

wherein =E is =O or (H,H), $R^{22}$ is H, $C_1$-$C_6$ alkyl, $C_6$-$C_{12}$ aryl, $C_1$-$C_4$ alkaryl, $COR^{24}$, $CO_2R^{24}$, $CONHR^{24}$, $CSR^{24}$, $COSR^{24}$, $CSOR^{24}$, $CSNHR^{24}$, $SO_2R^{24}$ or $SO_2NHR^{24}$, wherein $R^{24}$ is $C_1$-$C_6$ alkyl, $C_6$-$C_{12}$ aryl, or $C_1$-$C_4$ alkaryl, r is 1-2, and s is 0-1;
or A is H or OH;
X is H or $COCH_3$;
W, Y, and Z are defined as above; and
$R^4$ is

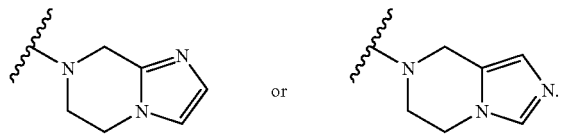

2. The compound of claim 1, wherein W is O.

3. A pharmaceutical composition comprising a pharmaceutically acceptable carrier or diluent and a compound of claim 1.

4. The composition of claim 3, wherein said composition is (i) a compound of claim 1 in an amount between 0.001% and 5% weight/volume (w/v) and (ii) a pharmaceutically acceptable carrier suitable for topical administration to a patient.

5. A method of treating a Gram-positive bacterial infection in an animal, said method comprising administering to said animal a pharmaceutical composition of claim 3 in an amount sufficient to treat said bacterial infection.

6. The method of claim 5, wherein said pharmaceutical composition is administered orally, topically, intravenously, intramusculary, or subcutaneously.

7. The method of claim 5, wherein said animal is a human patient.

8. The method of claim 5, wherein said bacterial infection is Clostridium difficile.

9. The method of claim 5, wherein said infection is Chlamydia trachomatis or N. gonorrhoeae.

10. The method of claim 5, wherein said bacterial infection is H. pylori.

11. The compound of claim 1, wherein said compound is selected from:
   3'-hydroxy-5'-(4-ethylcarbamyl-1-piperdinyl)benzoxazinorifamycin,
   25-O-deacetyl-3'-hydroxy-5'-(4-ethylcarbamyl-1-piperidinyl)benzoxazinorifamycin,
   3'-hydroxy-5'-[6-amino-(1R,5S)-3-azabicyclo[3.1.0]hex-3-yl]benzoxazinorifamycin,
   3'-hydroxy-5'-[(4aS,7aS)-octahydro-6H-pyrrolo[3,4-b]pyridin-6-yl]benzoxazinorifamycin,
   3'-hydroxy-5'-(1-piperidinyl-4-(N-phenyl)propanamide)benzoxazinorifamycin,
   25-O-deacetyl-3'-hydroxy-5'-[(4aS,7aS)-octahydro-6H-pyrrolo[3,4-b]pyridin-6-yl]benzoxazinorifamycin,
   25-O-deacetyl-3'-hydroxy-5'-(1-piperidinyl-4-(N-phenyl)propanamide)benzoxazinorifamycin,
   3'-hydroxy-5'-(3,8-diazabicyclo[3.2.1]octan-3-yl)benzoxazinorifamycin,
   3'-hydroxy-5'-[(4aR,7aR)-octahydro-6H-pyrrolo[3,4-b]pyridin-6-yl]benzoxazinorifamycin,
   3'-hydroxy-5'-(4-(2-methylpropyl)carbamyl-1-piperidinyl)benzoxazinorifamycin,
   25-O-deacetyl-3'-hydroxy-5'-(4-(2-methylpropyl)carbamyl-1-piperidinyl)benzoxazinorifamycin,
   25-O-deacetyl-3'-hydroxy-5'-[(4aR,7aR)-octahydro-6H-pyrrolo[3,4-b]pyridin-6-yl]benzoxazinorifamycin,
   25-O-deacetyl-3'-hydroxy-5'-(3,8-diazabicylo[3.2.1]octan-3-yl)benzoxazinorifamycin,
   3'-hydroxy-5'-(4-N,N-dimethylamino-1-piperidinyl)benzoxazinorifamycin,
   25-O-deacetyl-3'-hydroxy-5'-(4-N,N dimethylamino-1-piperidinyl)benzoxazinorifamycin,
   5'-(4-ethylcarbamyl-1-piperidinyl)-N'-methylbenzodiazinorifamycin,
   25-O-deacetyl-3'-hydroxy-5'-[6-amino-(1R,5S)-3-azabicyclo[3.1.0]hex-3-yl]benzoxazinorifamycin,
   3'-hydroxy-5'-[6-ethylcarbamyl-(1R,5S)-3-azabicyclo[3.1.0]hex-3-yl]benzoxazinorifamycin,
   3'-hydroxy-5'-[4-isopropylcarbamyl-1-piperidinyl]benzoxazinorifamycin,
   3'-hydroxy-5'-[4-trifluoromethylsulfonyl-1-piperidinyl]benzoxazinorifamycin,
   3'-hydroxy-5'-[4-butanamide-1-piperidinyl]benzoxazinorifamycin,
   3'-hydroxy-5'-[4-methylsulfonyl-1-piperidinyl]benzoxazinorifamycin,
   25-O-deacetyl-3'-hydroxy-5'-[4-propyluryl-1-piperidinyl]benzoxazinorifamycin,
   25-O-deacetyl-3'-hydroxy-5'-[4-methylsulfonyl-1-piperidinyl]benzoxazinorifamycin,
   3'-hydroxy-5'-[4-propyluryl-1-piperidinyl]benzoxazinorifamycin,
   25-O-deacetyl-3'-hydroxy-5'-[4-isopropylcarbamyl-1-piperidinyl]benzoxazinorifamycin,
   25-O-deacetyl-3'-hydroxy-5'-[4-methylcarbamyl-1-piperidinyl]benzoxazinorifamycin, 25-O-deacetyl-5'-(4-ethylcarbamyl-1-piperidinyl)-N'-methylbenzdiazinorifamycin, 3'-hydroxy-5'-[4-methylcarbamyl-1-piperidinyl]benzoxazinorifamycin, 3'-hydroxy-5'-[4-amino-1-piperidinyl]benzoxazinorifamycin, 3'-hydroxy-5'-[4-ethyluryl-1-piperidinyl]benzoxazinorifamycin, 3'-hydroxy-5'-[4-propylsulfonyl-1-piperidinyl]benzoxazinorifamycin, 25-O-deacetyl-3'-hydroxy-5'-[4-butanamide-1-piperidinyl]benzoxazinorifamycin, 25-O-deacetyl-3'-hydroxy-5'-[4-ethyluryl-1-piperidinyl]benzoxazinorifamycin, 25-O-deacetyl-3'-hydroxy-5'-[4-amino-1-piperidinyl]benzoxazinorifamycin, 3'-hydroxy-5'-[1-ethylcarbamyl-(4aR,7aR)-octahydro-6H-pyrrolo[3,4-b]pyridin-6-yl ]benzoxazinorifamycin, 3'-hydroxy-5'-[1-ethylcarbamyl-(4aS,7aS)-octahydro-6H-pyrrolo[3,4-b]pyridin-6-yl ]benzoxazinorifamycin, 25-O-deacetyl-3'-hydroxy-5'-[1-ethylcarbamyl-(4aR,7aR)-octahydro-6H-pyrrolo[3,4-b]pyridin-6yl]benzoxazinorifamycin, 25-O-deacetyl-3'-hydroxy-5'-[1-ethylcarbamyl-(4aS,7aS)-octahydro-6H-pyrrolo[3,4-b]pyridin-6-yl]benzoxazinorifamycin, 25-O-deacetyl-3'-hydroxy-5'-[4-acetamide-1-piperidinyl]benzoxazinorifamycin, 3'-hydroxy-5'-[4-acetylamino-1-piperidinyl]benzoxazinorifamycin, 3'-hydroxy-5'-[4-S-methylthiocarbamyl-1-piperidinyl]benzoxazinorifamycin, 25-O-deacetyl-3'-hydroxy-5'-[1-acetyl-(4aR,7aR)-octahydro-6H-pyrrolo[3,4-b]pyridin-6-yl]benzoxazinorifamycin, 25-O-deacetyl-3'-hydroxy-5'-[1-acetyl-(4aS,7aS)-octahydro-6H-pyrrolo[3,4-b]pyridin-6-benzoxazinorifamycin, 3'-hydroxy-5'-[1-acetyl-(4aR,7aR)-octahydro-6H-pyrrolo[3,4-b]pyridin-6-yl]benzoxazinorifamycin, 3'-hydroxy-5'-[1-acetyl-(4aS,7aS)-octahydro-6H-pyrrolo[3,4-b]pyridin-6-yl]benzoxazinorifamycin, 3'-hydroxy-5'-[4-(2,2-dimethylethyl)carbamyl-1-piperidinyl]benzoxazinorifamycin, 3'-hydroxy-5'-[4-(4S-methylthiocarbamyl)-1-pipercarbonyl)amino-1-piperidinyl]benzoxazinorifamycin, 25-O-deacetyl-3'-hydroxy-5'-[4-(2,2-dimethylethyl)carbamyl-1-piperidinyl]benzoxazinorifamycin, 25-O-deacetyl-3'-hydroxy-5'-[6-N,N-dimethylamino-(1R,5S)-3-azabicyclo[3.1.0]hex-3-yl]benzoxazinorifamycin, 3'-hydroxy-5'-[1-methyl-(4aS,7aS)-octahydro-6H-pyrrolo[3,4-b]pyridin-6-yl]benzoxazinorifamycin, 3'-hydroxy-5'-[1-methyl-(4aR,7aR)-octahydro-6H-pyrrolo[3,4-b]pyridin-6-yl]benzoxazinorifamycin, 25-O-deacetyl-3'-hydroxy-5'-[1-methyl-(4aS,7aS)-octahydro-6H-pyrrolo[3,4-b]pyridin-6yl]benzoxazinorifamycin, 25-O-deacetyl-3'-hydroxy-5'-[1-methyl-(4aR,7aR)-octahydro-6H-pyrrolo[3,4-b]pyridin-6-yl]benzoxazinorifamycin, 25-O-deacetyl-3'-hydroxy-5'-[4-ethylcarbamylmethyl-1-piperidinyl]benzoxazinorifamycin, 25-O-deacetyl3'-hydroxy-5'-[4-propylsulfonyl-1-piperidinyl]benzoxazinorifamycin, 5'-[4-N,N-dimethylamino-1-piperidinyl]benzthiazinorifamycin, 3'-hydroxy-5'-[4-methyl-4-N,N-dimethylamino-1-piperidinyl]benzoxazinorifamycin, 3'-hydroxy-5'-[4-acetylamino-1-piperidinyl]benzoxazinorifamycin, 25-O-deacetyl3'-hydroxy-5'-[4-methyl-4-N,N-dimethylamino-1-piperidinyl]benzoxazinorifamycin, 25-O-deacetyl3'-hydroxy-5'-[4-methyl-4-acetylamino-1-piperidinyl]benzoxazinorifamycin, 3'-hydroxy-5'-[(3R)-N,N-dimethylamino-1-piperidinyl]benzoxazinorifamycin, 3'-hydroxy-5'-[(3S)-N,N-dimethylamino-1-piperidinyl]benzoxazinorifamycin, 3'-hydroxy-5'-[3-hydroxy-1-azetidinyl]benzthiazinorifamycin, and 25-O-deacetyl3'-hydroxy-5'-[3-hydroxy-1-azetidinyl-]benzoxazinorifamycin.

12. The compound of claim 1, wherein said compound is selected from:

4'-fluoro-5'-(4-isobutyl-1-piperazinyl)benzoxazinorifamycin,

4'-fluoro-6'-methoxy-5'-[(4aS,7aS)-octahydro-6H-pyrrolo[3,4-b]pyridin-6-yl]benzoxazinorifamycin, 4'-fluoro-5'-[6-amino-3-azabicyclo[3.1.0]benzoxazinorifamycin, 25-O-deacetyl-4'-fluoro-5'-(4-isobutyl-1-piperazinyl)benzoxazinorifamycin, 25-O-deacetyl-4'-fluoro-6'methoxy-5'-[(4aS,7aS)-octahydro-6H-pyrrolo[3,4-b]pyridin-6-yl]benzoxazinorifamycin, 25-O-deacetyl-4'-fluoro-5'-[6-amino-3-azabicyclo[3.1.0]hex-3-yl]benzoxazinorifamycin, 25-O-deacetyl-25-(2'',3''-dihydroxypropylcarbonoxy)-4'-fluoro-6'-methoxy-5'-[(4aS,7aS)-octahydro-6H-pyrrlo[3,4-b]pyridin-6-yl]benzoxazinorifamycin, 25-O-deacetyl-25-(2'',3''-dihydroxypropylcarbonoxy)-4'-fluoro-5'-[6-amino-3-azabicyclo[3.1.0]hex-3-yl]benzoxazinorifamycin, 4'-fluoro-5'-(4-isobutyl-1-piperazinyl)benzthiazinorifamycin, 4'-fluoro-6'methoxy-5'-[(4aS,7aS)-octahydro-6H-pyrrolo[3,4-b]pyridin-6yl]benzthiazinorifamycin, 4'-fluoro-5'-[6-amino-3-azabicyclo[3.1.0]hex-3-yl]benzthiazinorifamycin, 25-O-deacetyl4'-fluoro-5'-(4-isobutyl-1-piperazinyl)benzthiazinorifamycin, 25-O-deacetyl-4'-fluoro-6'-methoxy-5'-[(4aS,7aS)-octahydro-6H-pyrrolo[3,4-b]pyridin-6-yl]benzthiazinorifamycin, 25-O-deacetyl-4'-fluoro-5'-[6-amino-3-azabicyclo[3.1.0]hex-3-yl]benzthiazinorifamycin, 25-O-deacetyl-3'-hydroxy-5'-((3R,5S)-3,5-dimethylpiperazinyl)benzoxazinorifamycin, 25-O-deacetyl-3'-hydroxy-5'-((3R,5S)-3-ethyl-5-methylpiperazinyl)benzoxazinorifamycin, 25-O-deacetyl-3'-hydroxy-5'-((3R,5S)-3,5-diethylpiperazinyl)benzoxazinorifamycin, 3'-hydroxy-5'-((3Z)-4-(aminomethyl)-pyrrolidinyl-3-one O-methyloxime) benzoxazinorifamycin, and 3'-hydroxy-5'-(5-azaspiro[2.4]heptan-7-amino-5-yl) benzoxazinorifamycin.

* * * * *